United States Patent
Sun et al.

(10) Patent No.: US 7,053,114 B2
(45) Date of Patent: *May 30, 2006

(54) PRODRUGS OF A 3-(PYRROL-2-YLMETHYLIDENE)-2-INDOLINONE DERIVATIVES

(75) Inventors: Connie Li Sun, Foster City, CA (US); Chung Chen Wei, Foster City, CA (US); Peng Cho Tang, Moraga, CA (US); Marcel Koenig, Burlingame, CA (US); Yong Zhou, San Francisco, CA (US); Tomas Vojkovsky, San Mateo, CA (US); Asaad S. Nematalla, Orinda, CA (US)

(73) Assignee: Sugen, Inc., South San Francisco, CA (US)

(*) Notice: Subject to any disclaimer, the term of this patent is extended or adjusted under 35 U.S.C. 154(b) by 22 days.

This patent is subject to a terminal disclaimer.

(21) Appl. No.: 10/816,957

(22) Filed: Apr. 5, 2004

(65) Prior Publication Data

US 2004/0186161 A1 Sep. 23, 2004

Related U.S. Application Data

(62) Division of application No. 10/118,321, filed on Apr. 9, 2002, now Pat. No. 6,797,725.

(60) Provisional application No. 60/282,630, filed on Apr. 9, 2001.

(51) Int. Cl.
*A61K 31/403* (2006.01)
*C07D 233/02* (2006.01)
*A61P 35/00* (2006.01)

(52) U.S. Cl. ............... 514/414; 514/399; 548/311.4; 548/465; 548/408

(58) Field of Classification Search .......... 514/414, 514/399; 548/311.4, 465, 468
See application file for complete search history.

(56) References Cited

U.S. PATENT DOCUMENTS

| 5,792,783 A | 8/1998 | Tang et al. |
| 6,395,734 B1 | 5/2002 | Tang et al. |
| 6,482,848 B1 | 11/2002 | Moon et al. |
| 6,797,725 B1 * | 9/2004 | Sun et al. ............ 514/414 |

FOREIGN PATENT DOCUMENTS

| WO | WO 90/08128 A1 | 7/1990 |
| WO | WO 99/61422 A | 12/1999 |
| WO | WO 00/08202 A | 2/2000 |
| WO | WO 01/90103 A | 11/2001 |

OTHER PUBLICATIONS

Monse et al. 2004, CAS:141:38635.*
Bundgaard, "Design of Prodrugs: Bioreversible dervatives for various functional groups and chemical entities," *Design of Prodrugs*, Chapter 1, 1985, pp. 10-27.

* cited by examiner

*Primary Examiner*—Taofiq Solola
*Assistant Examiner*—Robert Shiao
(74) *Attorney, Agent, or Firm*—Bryan C. Zielinski; Stephen D. Prodnuk; Ye Hua

(57) ABSTRACT

The present invention relates to pyrrole substituted 2-indolinone compounds and their pharmaceutically acceptable salts which modulate the activity of protein kinases and therefore are expected to be useful in the prevention and treatment of protein kinase related cellular disorders such as cancer.

8 Claims, No Drawings

PRODRUGS OF A 3-(PYRROL-2-YLMETHYLIDENE)-2-INDOLINONE DERIVATIVES

BACKGROUND OF THE INVENTION

1. Field of Invention

The present invention relates to certain 3-(pyrrol-2-ylmethylidene)-2-indolinone derivatives that are prodrugs of compounds that modulate the activity of protein kinases ("PKs"). Pharmaceutical compositions comprising these compounds, methods of treating diseases related to abnormal PK activity utilizing pharmaceutical compositions comprising these compounds and methods of preparing them are also disclosed.

2. State of the Art

The following is offered as background information only and is not admitted to be prior art to the present invention.

PKs are enzymes that catalyze the phosphorylation of hydroxy groups on tyrosine, serine and threonine residues of proteins. The consequences of this seemingly simple activity are staggering; cell growth, differentiation and proliferation, i.e., virtually all aspects of cell life in one way or another depend on PK activity. Furthermore, abnormal PK activity has been related to a host of disorders, ranging from relatively non life threatening diseases such as psoriasis to extremely virulent diseases such as glioblastoma (brain cancer) (see U.S. Pat. No. 5,792,783 which is incorporated herein by reference in its entirety).

In view of the apparent link between PK-related cellular activities and wide variety of human disorders, it is no surprise that a great deal of effort is being expended in an attempt to identify ways to modulate PK activity. Some of this effort has involved biomimetic approaches using large molecules patterned on those involved in the actual cellular processes (e.g., mutant ligands (U.S. Pat. No. 4,966,849); soluble receptors and antibodies (Published PCT Appl. WO 94/10202, Kendall and Thomas, *Proc. Nat'l Acad. Sci.*, 90:10705–09 (1994), Kim, et al., *Nature*, 362:841–844 (1993)); RNA ligands (Jelinek, et al., *Biochemistry*, 33:10450–56); Takano, et al., *Mol. Bio. Cell* 4:358A (1993); Kinsella, et al., *Exp. Cell Res.* 199:56–62 (1992); Wright, et al., *J. Cellular Phys.*, 152:448–57) and tyrosine kinase inhibitors (Published PCT Appls. WO 94/03427; WO 92/21660; WO 91/15495; WO 94/14808; U.S. Pat. No. 5,330,992; Mariani, et al., *Proc. Am. Assoc. Cancer Res.*, 35:2268 (1994)).

In addition to the above, attempts have been made to identify small molecules which act as PK inhibitors. For example, bis-monocylic, bicyclic and heterocyclic aryl compounds (Published PCT Appl. WO 92/20642), vinyleneazaindole derivatives (Published PCT Appl. WO 94/14808) and 1-cyclopropyl-4-pyridylquinolones (U.S. Pat. No. 5,330,992) have been described as tyrosine kinase inhibitors. Styryl compounds (U.S. Pat. No. 5,217,999), styryl-substituted pyridyl compounds (U.S. Pat. No. 5,302,606), quinazoline derivatives (EP App. No.0 566 266 A1), selenaindoles and selenides (Published PCT Appl. WO 94/03427), tricyclic polyhydroxylic compounds (Published PCT Appl. WO 92/21660), benzylphosphonic acid compounds (Published PCT Appl. WO 91/15495) and indolinone compounds (U.S. Pat. No. 5,792,783) have all been described as PTK inhibitors useful in the treatment of cancer. However these compounds have limited utility because of toxicity or poor bioavailability. Accordingly, there is a need for compounds that overcome these limitations. The compounds of the present invention fulfil this need.

SUMMARY OF THE INVENTION

The present invention is directed to certain 3-(pyrrol-2-ylmethylidene)-2-indolinone derivatives that are prodrugs of compounds that exhibit PK modulating ability and are therefore useful in treating disorders related to abnormal PK activity.

Accordingly, in one aspect, the present invention relates a compound of Formula (I):

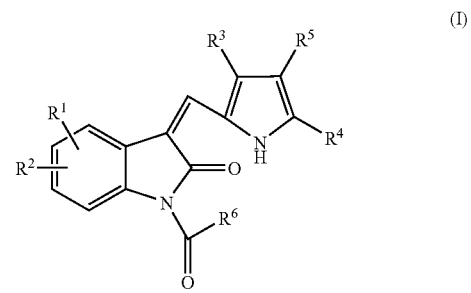

wherein:

$R^1$ and $R^2$ are independently selected from the group consisting of hydrogen, halo, alkyl, alkylthio, nitro, trihalomethyl, hydroxy, hydroxyalkyl, alkoxy, cyano, aryl, heteroaryl, —C(O)$R^7$ (where $R^7$ is selected from the group consisting of alkyl, amino, hydroxy, alkoxy, aryl, heteroaryl, aryloxy, heteroaryloxy, heterocycle, and aminoalkylamino), —NR$^8$R$^9$, —NR$^8$C(O)R$^9$, —SO$_2$R$^8$, and —S(O)$_2$NR$_8$R$^9$ (where $R^8$ and $R^9$ are independently selected from the group consisting of hydrogen, alkyl, aryl and heteroaryl, or $R^8$ and $R^9$ together with the nitrogen to which they are attached form a saturated heterocycloamino);

$R^3$ is selected from the group consisting of hydrogen, alkyl, hydroxyalkyl, aminoalkyl, —C(O)$R^7$ (where $R^7$ is as defined above), aryl, and heteroaryl;

$R^4$ is selected from the group consisting of hydrogen, alkyl, —C(O)$R^7$ (where $R^7$ is as defined above), aryl, and heteroaryl;

$R^5$ is selected from the group consisting of hydrogen and —COR$^{10}$ where $R^{10}$ is alkyl, alkoxy, hydroxy, aryl, aryloxy, heteroaryl, heterocyle, alkylamino, dialkylamino, or —NR$^{11}$R$^{12}$ where $R^{11}$ is hydrogen or alkyl, and $R^{12}$ is aminoalkyl, hydroxyalkyl, acetylalkyl, cyanoalkyl, carboxyalkyl, alkoxycarbonylalkyl, heteroaralkyl, or heterocyclylalkyl; wherein the alkyl chain in aminoalkyl, heteroaralkyl, heteroaralkyl, or heterocyclylalkyl is optionally substituted with one or two hydroxy group(s); or $R^4$ and $R^5$ together form —(CH$_2$)$_4$— or —(CH$_2$)$_m$CO(CH$_2$)$_n$— wherein n is 0 to 3, n is 0 to 3 provided that n+m is 3;

$R^6$ is:

(a) —OR$^{13}$ wherein $R^{13}$ is alkyl, trifluoromethyl, carboxyalkyl, aminoalkyl, phosphonooxyalkyl, sulfooxyalkyl, hydroxyalkyl, alkoxyalkyl, aryl, heteroaryl, heteroaralkyl, heterocyclyl, monosaccharides and heterocyclylalkyl; wherein the alkyl chain in carboxyalkyl, aminoalkyl, phosphonooxyalkyl, sulfooxyalkyl, heteroaralkyl, heterocyclylalkyl, hydroxyalkyl, or alkoxyalkyl is optionally substituted with one or two hydroxy group(s) and further wherein one or two carbon atoms in said alkyl chain are optionally replaced by oxygen, —NR$^{14}$— (where $R^{14}$ is hydrogen or alkyl), —S—, or —SO$_2$—; or (b) —NR$^{15}$R$^{16}$ where are $R^{15}$ and $R^{16}$ are independently selected from the group consisting of hydrogen, alkyl, carboxyalkyl, alkoxyalkyl, aminoalkyl, phosphonooxyalkyl, sulfooxyalkyl, hydroxyalkyl, aryl, heteroaryl, heteroaralkyl, and heterocyclylalkyl wherein the alkyl chain in carboxyalkyl, aminoalkyl, phosphonooxyalkyl, sulfooxyalkyl, heteroaralkyl, heterocyclylalkyl, hydroxyalkyl, or alkoxyalkyl is optionally substituted with one or two hydroxy group(s) and further wherein one or two carbon atoms in the alkyl chain are optionally replaced by oxygen, —NR$^{17}$— (where R$^{17}$ is hydrogen or alkyl), —S—, or —SO$_2$—; or R$^{15}$ and R$^{16}$ together with the nitrogen atom to which they are attached form saturated or unsaturated heterocycloamino;

or a pharmaceutically acceptable salt thereof.

Specifically, the compounds of the present invention convert in vivo to compounds of Formula (II):

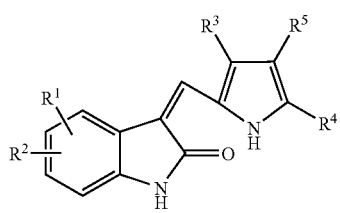

that exhibit PK modulating ability, in particular PK inhibiting ability, and are therefore useful in treating disorders related to abnormal PK activity. The active compounds (II) formed from the compounds of the present invention are described in U.S. Pat. No. 5,792,783, and U.S. patent application Ser. No. 09/---,---, filed on Feb. 15, 2001, and titled "PYRROLE SUBSTITUTED 2-INDOLINONE PROTEIN KINASE INHIBITORS" which are hereby incorporated by reference.

The compounds of the present invention have advantages over compounds of Formula (II) by virtue of improved solubility and formulability. For example, it has been discovered that prodrugs of compound (II) where R$^1$, R$^2$, and R$^5$ are hydrogen and R$^3$ and R$^4$ are methyl provide improved aqueous solubility over the parent compound. It is contemplated that similar enhanced bioavailability will be observed with other compounds within the scope of the present invention.

A general description of the advantages and uses of prodrugs as pharmaceutically useful compounds is given in an article by Waller and George in *Br. J. Clin. Pharmac.*, Vol. 28, pp. 497–507, 1989.

By way of illustration, the following compounds of the present invention are converted to the indicated PK inhibitors of Formula (II).

| Example No. | Prodrug | Active Compound | Reference |
|---|---|---|---|
| 1 | | | U.S. Pat. No. 5,792,783 |
| 2 | | | same |

-continued

| Example No. | Prodrug | Active Compound | Reference |
|---|---|---|---|
| 3 | 3-[(3,5-dimethyl-1H-pyrrol-2-yl)methylene]-2-oxo-indoline-1-carboxylic acid 2-(2-methoxyethoxy)ethyl ester | same | |
| 4 | 3-[(3,5-dimethyl-1H-pyrrol-2-yl)methylene]-2-oxo-indoline-1-carboxylic acid 2-(2-hydroxyethoxy)ethyl ester | same | |
| 5 | 3-[(3,5-dimethyl-1H-pyrrol-2-yl)methylene]-2-oxo-indoline-1-carboxylic acid 2-hydroxyethyl ester | same | |
| 6 | 3-[(3,5-dimethyl-1H-pyrrol-2-yl)methylene]-2-oxo-indoline-1-carboxylic acid 2,3-dihydroxypropyl ester | same | |

-continued

| Example No. | Prodrug | Active Compound | Reference |
|---|---|---|---|
| 7 | (structure) | same | |
| 8 | (structure) | same | |
| 9 | (structure) | same | |
| 10 | (structure) | same | |

-continued
| Example No. | Prodrug | Active Compound | Reference |
|---|---|---|---|
| 11 | 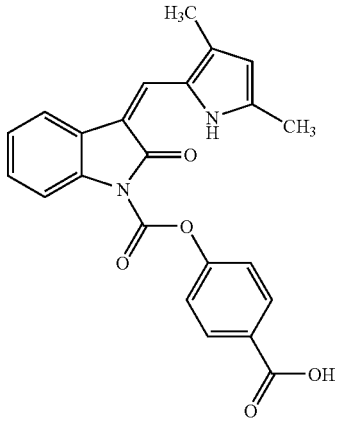 | same | |
| 12 | 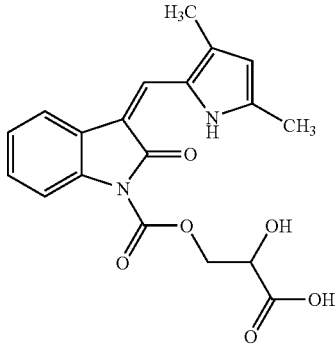 | same | |
| 13 | 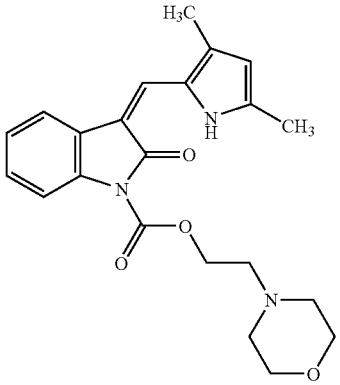 | same | |
| 14 | 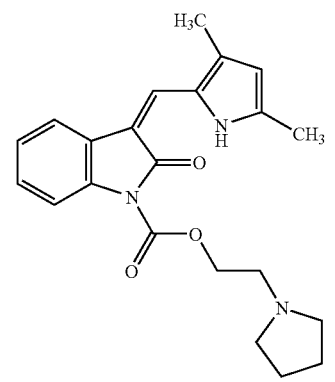 | same | |

-continued
| Example No. | Prodrug | Active Compound | Reference |
|---|---|---|---|
| 15 | 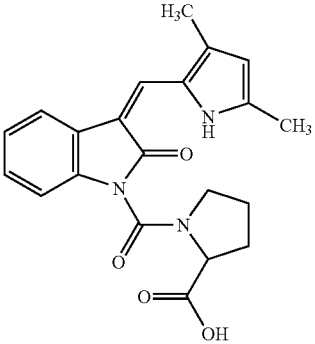 | same | |
| 16 | 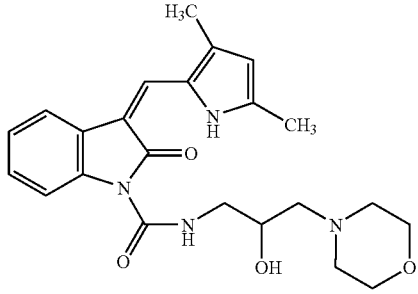 | same | |
| 17 | 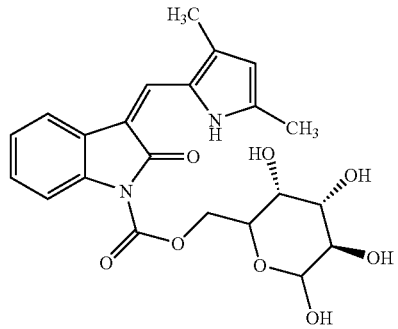 | same | |
| 18 | 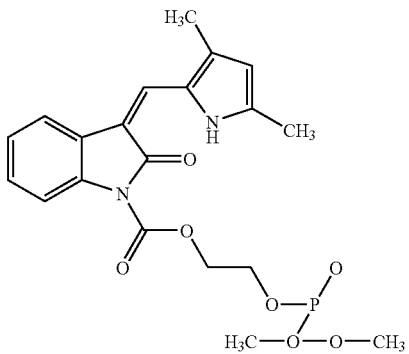 | same | |

-continued

| Example No. | Prodrug | Active Compound | Reference |
|---|---|---|---|
| 19 | [chemical structure: 3-[(3,5-dimethyl-1H-pyrrol-2-yl)methylene]-2-oxoindoline-1-carboxylic acid 2-(phosphonooxy)ethyl ester] | same | |
| 20 | [chemical structure: 3-[(3,5-dimethyl-1H-pyrrol-2-yl)methylene]-2-oxoindoline-1-carboxylic acid 2-(diethylamino)ethyl ester] | same | |
| 21 | [chemical structure: 3-[(3,5-dimethyl-1H-pyrrol-2-yl)methylene]-2-oxoindoline-1-carboxylic acid 3-hydroxypropyl ester] | same | |
| 22 | [chemical structure: 3-[(3,5-dimethyl-1H-pyrrol-2-yl)methylene]-2-oxoindoline-1-carboxylic acid 2-hydroxy-3-(pyrrolidin-1-yl)propyl ester] | same | |

-continued

| Example No. | Prodrug | Active Compound | Reference |
|---|---|---|---|
| 23 | | same | |
| 24 | | same | |
| 25 | | same | |
| 26 | | same | |

-continued

| Example No. | Prodrug | Active Compound | Reference |
|---|---|---|---|
| 27 | *[structure: 3-((3,5-dimethyl-1H-pyrrol-2-yl)methylene)-2-oxoindoline-1-carboxylic acid 3-(dimethoxyphosphoryloxy)propyl ester]* | same | |
| 28 | *[structure: 3-((3,5-dimethyl-1H-pyrrol-2-yl)methylene)-1-(2,5-dihydro-1H-pyrrole-3-carbonyl)indolin-2-one]* | same | |
| 29 | *[structure: 3-((3,5-dimethyl-1H-pyrrol-2-yl)methylene)-2-oxoindoline-1-carboxylic acid 2-hydroxy-3-(sodium sulfonatooxy)propyl ester]* | same | |

In a second aspect this invention is directed to a pharmaceutical composition comprising one or more compound(s) of Formula (I) or a pharmaceutically acceptable salt thereof and a pharmaceutically acceptable excipient.

In a third aspect, this invention is directed to a method of treating diseases mediated by abnormal protein kinase activity, in particular, receptor tyrosine kinases (RTKs), non-receptor protein tyrosine kinases (CTKs) and serine/threonine protein kinases (STKs), in an organism, in particular humans, which method comprises administering to said organism a pharmaceutical composition comprising a compound of Formula (I) and a pharmaceutically acceptable excipient. Such diseases include by way of example and not limitation, cancer, diabetes, hepatic cirrhosis, cardiovascular disease such as atherosclerosis, angiogenesis, immunological disease such as autoimmune disease and renal disease. Specifically, the diseases mediated by EGF, HER2, HER3, HER4, IR, IGF-LR, IRR, PDGFRα, PDGFRβ, CSFIR, C-Kit, C-fms, Flk-1R, Flk4, KDR/Flk-1, Flt-1, FGFR-1R, FGFR-2R, FGFR-3R, FGFR-4R, Src, Frk, Btk, Csk, Abl, ZAP70, Fes/Fps, Fak, Jak, Ack, Yes, Fyn, Lyn, Lck, Blk, Hck, Fgr, Yrk, CDK2 and Raf.

In a fourth aspect, this invention is directed to a method of modulating the catalytic activity (e.g., inhibiting the catalytic activity) of PKs, in particular receptor tyrosine kinases (RTKs), non-receptor protein tyrosine kinases (CTKs) and serine/threonine protein kinases (STKs), using a compound of this invention or a pharmaceutical composition comprising a compound of this invention and a pharmaceutically acceptable excipient. The method may be carried out in vitro or in vivo. In particular, the receptor protein kinase whose catalytic activity is modulated by a compound of this invention is selected from the group consisting of EGF, HER2, HER3, HER4, IR, IGF-1R, IRR, PDGFRα, PDGFRβ, CSFIR, C-Kit, C-fms, Flk-1R, Flk4, KDR/Flk-1, Flt-1, FGFR-1R, FGFR-2R, FGFR-3R and FGFR-4R. The cellular tyrosine kinase whose catalytic activity is modulated by a compound of this invention is selected from the group consisting of Src, Frk, Btk, Csk, Abl, ZAP70, Fes/Fps, Fak, Jak, Ack, Yes, Fyn, Lyn, Lck, Blk, Hck, Fgr and Yrk. The serine-threonine protein kinase whose catalytic activity is modulated by a compound of this invention is selected from the group consisting of CDK2 and Raf.

In a fifth aspect, this invention is directed to the use of a compound of Formula (I) in the preparation of a medicament which is useful in the treatment of a disease mediated by abnormal PK activity.

In a sixth aspect, this invention is directed to intermediates of Formula (III) useful for preparing the compounds of Formula (I):

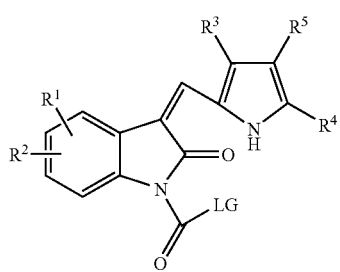

(III)

where $R^1$–$R^5$ are as defined in compounds of Formula (I) above and LG is a leaving group, under acylating reaction conditions. Preferably LG is imidazol-1-yl or halo such as chloro, bromo or iodo.

In a seventh aspect, this invention is directed to a method of preparing a compound of Formula (I) which method comprises reacting a compound of Formula (III):

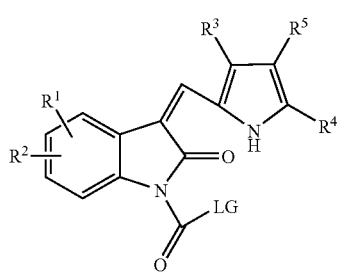

(III)

where LG is a leaving group, under acylating reaction conditions:

(i) with an alcohol of formula $R^{13}OH$ where $R^{13}$ is defined in Formula (I), optionally in the presence of an acid or base to provide a compound of Formula (I); or (ii) with an amine of formula —$NR^{15}R^{16}$ where $R^{15}$ and $R^{16}$ are as defined in Formula (I) to provide a compound of Formula (I);

(iii) optionally preparing an acid addition salt; and (iv) optionally modifying any of the $R^1$–$R^5$ groups.

Preferably, LG is chloro or imidazol-1-yl.

Lastly, this invention is directed to a method of identifying a chemical compound that modulates the catalytic activity of a protein kinase which method comprises by contacting cells expressing said protein kinase with said compound and then monitoring said cells for an effect.

DETAILED DESCRIPTION OF THE INVENTION

Definitions

Unless otherwise stated the following terms used in the specification and claims have the meanings discussed below:

"Alkyl" refers to a saturated straight or branched hydrocarbon radical of 1 to 20 carbon atoms. More preferably, it is a medium size alkyl radical having 1 to 10 carbon atoms e.g., methyl, ethyl, propyl, 2-propyl, n-butyl, iso-butyl, tert-butyl, pentyl, and the like. Most preferably, it is lower alkyl having 1 to 4 carbon atoms e.g., methyl, ethyl, propyl, 2-propyl, n-butyl, iso-butyl, or tert-butyl, and the like.

"Hydroxyalkyl" means a saturated straight or branched monovalent hydrocarbon radical of one to six carbon atoms substituted with one or two hydroxy groups, provided that if two hydroxy groups are present they are not both on the same carbon atom. Representative examples include, but are not limited to, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Alkoxyalkyl" means a saturated straight or branched monovalent hydrocarbon radical of one to six carbon atoms substituted with one or two alkoxy groups as defined above, e.g., methoxymethyl, 2-methoxyethyl, 2-methoxypropyl, 3-methoxypropyl, and the like.

"Aminoalkyl" means a saturated straight or branched monovalent hydrocarbon radical of one to six carbon atoms substituted with one or two —NRR' where R and R' are independently selected from hydrogen, alkyl, or acyl, e.g., 2-aminoethyl, 2-N-ethylaminoethyl, 2-N,N-diethylaminoethyl, 2-N,N-diethylaminopropyl, 2-N-acetylaminoethyl, and the like.

"Aminoalkylamino" means an —NHR group wherein R is an aminoalkyl group as defined above, e.g., 2-aminoethylamino, 2-N-ethylaminoethylamino, 2-N,N-diethylaminoethylamino, 2-N,N-diethylaminopropylamino, 2-N-acetylaminoethylamino, and the like.

"Acyl" means a radical —C(O)R where R is hydrogen, lower alkyl, or haloalkyl as defined herein, e.g., formyl, acetyl, trifluoroacetyl, butanoyl, and the like.

"Carboxyalkyl" means a saturated straight or branched monovalent hydrocarbon radical of one to six carbon atoms substituted with one or two —COOH group e.g., carboxymethyl, 2-carboxyethyl, 3-carboxypropyl, and the like.

"Phosphonooxyalkyl" means a saturated straight or branched monovalent hydrocarbon radical of one to six carbon atoms substituted with a —$OPO_3H$ group, or —OPO($OMe_2$) group e.g., phosphonooxymethyl, 2-phosphonooxyethyl, 3-phosphonooxypropyl, and the like.

"Sulfooxyalkyl" means a saturated straight or branched monovalent hydrocarbon radical of one to six carbon atoms substituted with a —$OSO_3H$ group, or —OSO($OMe_2$) group e.g., sulfooxymethyl, 2-sulfoxyethyl, 2-dimethoxysulfoxyethyl, 3-sulfooxypropyl, and the like.

"Alkylthio" means a radical —SR where R is alkyl as defined above, e.g., methylthio, ethylthio, butylthio, and the like.

"Alkenyl" refers to a lower alkyl group, as defined herein, consisting of at least two carbon atoms and at least one carbon-carbon double bond. Representative examples include, but are not limited to, ethenyl, 1-propenyl, 2-propenyl, 1-, 2-, or 3-butenyl, and the like.

"Substituted alkenyl" refers to an alkenyl group as defined above which is substituted with one, two or three groups selected from halo, carboxy, —C(O)OR where R is alkyl, amino, or nitro.

"Aryl" refers to an all-carbon monocyclic or fused-ring polycyclic (i.e., rings which share adjacent pairs of carbon atoms) groups of 6 to 12 carbon atoms having a completely conjugated pi-electron system. Examples, without limitation, of aryl groups are phenyl, naphthalenyl and anthracenyl. The aryl group may be substituted or unsubstituted. When substituted, the aryl group is substituted with one or more, more preferably one, two or three, even more preferably one or two substituents independently selected from the group consisting of lower alkyl, alkenyl, substituted alkenyl, trihaloalkyl, halo, hydroxy, alkoxy, mercapto, alkylthio, cyano, acyl, thioacyl, O-carbamyl, N-carbamyl, O-thiocarbamyl, N-thiocarbamyl, C-amido, N-amido, nitro, N-sulfonamido, S-sulfonamido, $R^{18}S(O)$—, $R^{18}S(O)_2$—, —C(O)OR$^{18}$, $R^{18}C(O)O$—, and —NR$^{18}R^{19}$, with $R^{18}$ and $R^{19}$ are independently selected from hydrogen, lower alkyl, aryl substituted with halo, hydroxy, alkoxy, amino, carboxy, nitro or cyano, heteroaryl substituted with halo, hydroxy, alkoxy, amino, carboxy, nitro or cyano, aralkyl wherein the aryl ring is substituted with halo, hydroxy, alkoxy, amino, carboxy, nitro or cyano, or heteroaralkyl wherein the heteroaryl ring is substituted with halo, hydroxy, alkoxy, amino, carboxy, nitro or cyano. Preferably, the aryl group is optionally substituted with one or two substituents independently selected from halo, lower alkyl, trihaloalkyl, hydroxy, cyano, N-amido, mono- or dialkylamino, carboxy, or N-sulfonamido.

"Heteroaryl" refers to a monocyclic or fused ring (i.e., rings which share an adjacent pair of atoms) group of 5 to 12 ring atoms containing one, two, three or four ring heteroatoms selected from N, O, or S, the remaining ring atoms being C, and, in addition, having a completely conjugated pi-electron system. Examples, without limitation, of unsubstituted heteroaryl groups are pyrrole, furan, thiophene, imidazole, oxazole, thiazole, pyrazole, pyridine, pyrimidine, quinoline, isoquinoline, purine, triazole, tetrazole, triazine, and carbazole. The heteroaryl group may be substituted or unsubstituted. When substituted, the the heteroaryl ring is substituted with one or more, more preferably one, two, or three, even more preferably one or two substituents, independently selected from the group consisting of lower alkyl, trihaloalkyl, halo, nitro, amino, hydroxy, alkoxy, mercapto, alkylthio, cyano, acyl, thioacyl, O-carbamyl, N-carbamyl, O-thiocarbamyl, N-thiocarbamyl, C-amido, N-amido, nitro, N-sulfonamido, S-sulfonamido, $R^{18}S(O)$—, $R^{18}O)_2$—, —C(O)OR$^{18}$, $R^{18}C(O)O$—, and —NR$^{18}R^{19}$, with $R^{18}$ and $R^{19}$ as defined above. Preferably, the heteroaryl group is optionally substituted with one or two substituents independently selected from halo, lower alkyl, trihaloalkyl, hydroxy, mercapto, cyano, N-amido, mono or dialkylamino, carboxy, or N-sulfonamido.

"Heterocycle" means a saturated cyclic radical of 3 to 8 ring atoms in which one, two or three ring atoms are heteroatoms selected from N, O, or $S(O)_n$ (where n is an integer from 0 to 2), the remaining ring atoms being C, where one or two C atoms may optionally be replaced by a carbonyl group. The heterocyclyl ring may be optionally substituted independently with one or more, preferably one, two, or three substituents selected from lower alkyl (wherein the lower alkyl may be optionally substituted with one or two substituents independently selected from carboxy or ester group), haloalkyl, cyanoalkyl, halo, nitro, cyano, hydroxy, alkoxy, amino, monoalkylamino, dialkylamino, aralkyl, heteroaralkyl, and —COR (where R is alkyl). More specifically the term heterocyclyl includes, but is not limited to, tetrahydropyranyl, 2,2-dimethyl-1,3-dioxolane, piperidino, N-methylpiperidin-3-yl, piperazino, N-methylpyrrolidin-3-yl, pyrrolidino, morpholino, thiomorpholino, thiomorpholino-1-oxide, thiomorpholino-1,1-dioxide, 4-ethyloxycarbonylpiperazino, 3-oxopiperazino, 2-imidazolidone, 2-pyrrolidinone, 2-oxohomopiperazino, tetrahydropyrimidin-2-one, and the derivatives thereof. Preferably, the heterocycle group is optionally substituted with one or two substituents independently selected from halo, lower alkyl, lower alkyl substituted with carboxy, ester, hydroxy, or mono or dialkylamino.

"Saturated heterocycloamino" means a saturated cyclic radical of 3 to 8 ring atoms in which at least one of the ring atoms is nitrogen and optionally where one or two additionally ring atoms are heteroatoms selected from NR$^a$ (where R$^a$ is alkyl, substituted alkyl acyl, aryl, or heteroaryl), O, or $S(O)_n$ (where n is an integer from 0 to 2), the remaining ring atoms being C, where one or two C atoms may optionally be replaced by a carbonyl group. The heterocycloamino ring may be optionally substituted independently with one, two, or three substituents selected from alkyl (optionally substituted with one or two substituents independently selected from carboxy or ester group), haloalkyl, cyanoalkyl, halo, nitro, cyano, hydroxy, alkoxy, amino, monoalkylamino, dialkylamino, aralkyl, heteroaralkyl, and —COR (where R is alkyl). More specifically the term heterocycloamino includes, but is not limited to, piperidyn-1-yl, piperazin-1-yl, pyrrolidin-1-yl, 2-oxo-pyrrolidin-1-yl, 2,5-dioxo-pyrrolidin-1-yl, morpholin-4-yl, thiomorpholin-4-yl, thiomorpholino-1-oxide, thiomorpholino-1,1-dioxide, 4-ethyloxycarbonylpiperazin-1-yl, 3-oxopiperazin-1-yl, 2-imidazolidon-1-yl, 2-pyrrolidinon-1-yl, 2-oxohomopiperazino, tetrahydropyrimidin-2-one, and the derivatives thereof. The heterocycloamino group is a subset of the heterocycle group defined above.

"Unsaturated heterocycloamino" means a non-aromatic cyclic radical of 4 to 8 ring atoms containing one or two double bonds within the ring provided that the ring is not aromatic, and in which at least one of the ring atoms is nitrogen and optionally where one or two additionally ring atoms are heteroatoms independently selected from NR$^a$ (where R$^a$ is alkyl, substituted alkyl acyl, aryl, or heteroaryl), O, or $S(O)_n$ (where n is an integer from 0 to 2), the remaining ring atoms being C where one or two C atoms may optionally be replaced by a carbonyl group. The heterocycloamino ring may be optionally substituted independently with one, two, or three substituents selected from alkyl (wherein the alkyl group can be optionally substituted one or two substituents independently selected from carboxy or ester group), haloalkyl, cyanoalkyl, halo, nitro, cyano, hydroxy, alkoxy, amino, monoalkylamino, dialkylamino, aralkyl, heteroaralkyl, and —COR (where R is alkyl).

"Hydroxy" refers to an —OH group.

"Alkoxy" refers to an —OR group where R is lower alkyl as defined above. Representative examples include, but are not limited to, e.g., methoxy, ethoxy, propoxy, butoxy, and the like.

"Aryloxy" refers to both an —OR where R is an aryl group, as defined herein. Representative examples include, but are not limited to, phenoxy, anthryloxy and the like, and derivatives thereof.

"Heteroaryloxy" refers to both an —OR where R is a heteroaryl group, as defined herein. Representative examples include, but are not limited to, pyridinyloxy, furanyloxy, thienyloxy, pyrimidinyloxy, pyrazinyloxy, and the like, and derivatives thereof.

"Acetylalkyl" means a lower alkyl group as defined above carrying a —C(O)CH$_3$ group, e.g., acetylmethyl, acetylethyl, acetylpropyl, and the like.

"Cyanoalkyl" means a lower alkyl group as defined above carrying a —CN group e.g., cyanomethyl, 2-cyanoethyl, 3-cyanopropyl, 2-cyanopropyl, and the like.

"Alkoxycarbonylalkyl" means a lower alkyl group as defined above carrying a —COOR group where R is lower alkyl e.g., methoxycarbonylmethyl, 2-methoxycarbonylethyl, 2-ethoxycarbonylethyl, 3-methoxycarbonyl or ethoxycarbonylpropyl, 2-methoxycarbonyl or ethoxycarbonylpropyl, and the like.

"Halo" group refers to fluorine, chlorine, bromine or iodine, preferably fluorine or chlorine.

"Trihalomethyl" group refers to a —CX$_3$ group wherein X is a halo group as defined herein.

"Cyano" refers to a —C≡N group.

"S-sulfonamido" refers to a —S(O)$_2$NR$^{18}$R$^{19}$ group, with R$^{18}$ and R$^{19}$ as defined herein.

"N-sulfonamido" refers to a —NR$^{18}$(O)$_2$R$^{19}$ group, with R$^{18}$ and R$^{19}$ as defined herein.

"O-carbamyl" group refers to a —OC(O)NR$^{18}$R$^{19}$ group with R$^{18}$ and R$^{19}$ as defined herein.

"N-carbamyl" refers to an R$^{18}$OC(O)NR$^{19}$— group, with R$^{18}$ and R$^{19}$ as defined herein.

"O-thiocarbamyl" refers to a —OC(S)NR$^{18}$R$^{19}$ group with R$^{18}$ and R$^{19}$ as defined herein.

"N-thiocarbamyl" refers to a R$^{18}$OC(S)NR$^{19}$— group, with R$^{18}$ and R$^{19}$ as defined herein.

"Amino" refers to an —NR$^{18}$R$^{19}$ group, wherein R$^{18}$ and R$^{19}$ are both hydrogen.

"C-amido" refers to a —C(O)NR$^{18}$R$^{19}$ group with R$^{18}$ and R$^{19}$ as defined herein.

"N-amido" refers to a R$^{18}$C(O)NR$^{19}$— group, with R$^{18}$ and R$^{19}$ as defined herein.

"Nitro" refers to a —NO$_2$ group.

"Haloalkyl" means an alkyl as defined above that is substituted with one or more same or different halo atoms, e.g., —CH$_2$Cl, —CF$_3$, —CH$_2$CF$_3$, —CH$_2$CCl$_3$, and the like.

"Aralkyl" means alkyl as defined above which is substituted with an aryl group as defined above, e.g., —CH$_2$phenyl, —(CH$_2$)$_2$phenyl, —(CH$_2$)$_3$phenyl, —CH$_2$CH(CH$_3$)CH$_2$phenyl, and the like and derivatives thereof.

"Heteroaralkyl" group means alkyl as defined above which is substituted with a heteroaryl group, e.g., —CH$_2$pyridinyl, —(CH$_2$)$_2$pyrimidinyl, —(CH$_2$)$_3$imidazolyl, and the like, and derivatives thereof.

"Heterocyclylalkyl" group means alkyl as defined above which is substituted with a heterocycle group, e.g., —CH$_2$pyrrolidin-1-yl, —(CH$_2$)$_2$piperidin-1-yl, and the like, and derivatives thereof.

"Alkylamino" means a radical —NHR where R is alkyl, e.g., methylamino, (1-methylethyl)amino, and the like.

"Dialkylamino" means a radical —NRR' where R and R' are independently alkyl e.g., dimethylamino, methylethylamino, di(1-methylethyl)amino, and the like.

"Monosaccharides" means sugars that are not hydrolyzable into smaller units e.g., glucose, galactose, and the like.

"Optional" or "optionally" means that the subsequently described event or circumstance may, but need not occur, and that the description includes instances where the event or circumstance occurs and instances in which it does not.

For example, "heterocycle group optionally substituted with an alkyl group" means that the alkyl may but need not be present, and the description includes situations where the heterocycle group is substituted with an alkyl group and situations where the heterocyclo group is not substituted with the alkyl group.

The terms "2-indolinone", "indolin-2-one" and "2-oxindole" are used interchangeably herein to refer to a molecule having the chemical structure:

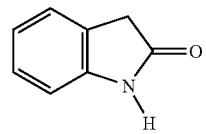

The term "pyrrole" refers to a molecule having the chemical structure:

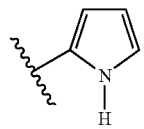

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. For example, if the R$^6$ substituent in a compound of formula (I) is 2-hydroxyethyl, then the carbon to which the hydroxy group is attached is an asymmetric center and therefore the compound of Formula (I) can exist as an (R)- or (S)-stereoisomer. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

The compounds of Formula (I) may exhibit the phenomena of tautomerism and structural isomerism. For example, the compounds described herein may adopt an E or a Z configuration about the double bond connecting the 2-indolinone moiety to the pyrrole moiety or they may be a mixture of E and Z. This invention encompasses any tautomeric or structural isomeric form and mixtures thereof which possess the ability to modulate RTK, CTK and/or STK activity and is not limited to any one tautomeric or structural isomeric form.

A "pharmaceutical composition" refers to a mixture of one or more of the compounds described herein, or physiologically/pharmaceutically acceptable salts or prodrugs thereof, with other chemical components, such as physiologically/pharmaceutically acceptable carriers and excipients. The purpose of a pharmaceutical composition is to facilitate administration of a compound to an organism.

It is contemplated that a compound of Formula (I) would be metabolized by enzymes in the body of the organism such as human being to generate a metabolite that can modulate the activity of the protein kinases. Such metabolites are within the scope of the present invention.

As used herein, a "pharmaceutically acceptable carrier" refers to a carrier or diluent that does not cause significant irritation to an organism and does not abrogate the biological activity and properties of the administered compound.

An "pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

As used herein, the term "pharmaceutically acceptable salt" refers to those salts which retain the biological effectiveness and properties of the parent compound. Such salts include:

(1) acid addition salt which is obtained by reaction of the free base of the parent compound with inorganic acids such as hydrochloric acid, hydrobromic acid, nitric acid, phosphoric acid, sulfuric acid, and perhcloric acid and the like, or with organic acids such as acetic acid, oxalic acid, (D) or (L) malic acid, maleic acid, methanesulfonic acid, ethanesulfonic acid, p-toluenesulfonic acid, salicylic acid, tartaric acid, citric acid, succinic acid or malonic acid and the like, preferably hydrochloric acid or (L)-malic acid; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"PK" refers to receptor protein tyrosine kinase (RTKs), non-receptor or "cellular" tyrosine kinase (CTKs) and serine-threonine kinases (STKs).

"Method" refers to manners, means, techniques and procedures for accomplishing a given task including, but not limited to, those manners, means, techniques and procedures either known to, or readily developed from known manners, means, techniques and procedures by, practitioners of the chemical, pharmaceutical, biological, biochemical and medical arts.

"Modulation" or "modulating" refers to the alteration of the catalytic activity of RTKs, CTKs and STKs. In particular, modulating refers to the activation of the catalytic activity of RTKS, CTKs and STKs, preferably the activation or inhibition of the catalytic activity of RTKs, CTKs and STKs, depending on the concentration of the compound or salt to which the RTK, CTK or STK is exposed or, more preferably, the inhibition of the catalytic activity of RTKs, CTKs and STKs.

"Catalytic activity" refers to the rate of phosphorylation of tyrosine under the influence, direct or indirect, of RTKs and/or CTKs or the phosphorylation of serine and threonine under the influence, direct or indirect, of STKs.

"Contacting" refers to bringing a compound of this invention and a target PK together in such a manner that the compound can affect the catalytic activity of the PK, either directly, i.e., by interacting with the kinase itself, or indirectly, i.e., by interacting with another molecule on which the catalytic activity of the kinase is dependent. Such "contacting" can be accomplished in vitro, i.e., in a test tube, a petri dish or the like. In a test tube, contacting may involve only a compound and a PK of interest or it may involve whole cells. Cells may also be maintained or grown in cell culture dishes and contacted with a compound in that environment. In this context, the ability of a particular compound to affect a PK related disorder, i.e., the $IC_{50}$ of the compound, defined below, can be determined before use of the compounds in vivo with more complex living organisms is attempted. For cells outside the organism, multiple methods exist, and are well-known to those skilled in the art, to get the PKs in contact with the compounds including, but not limited to, direct cell microinjection and numerous transmembrane carrier techniques.

"In vitro" refers to procedures performed in an artificial environment such as, e.g., without limitation, in a test tube or culture medium.

"In vivo" refers to procedures performed within a living organism such as, without limitation, a mouse, rat or rabbit.

"PK related disorder," "PK driven disorder," and "abnormal PK activity" all refer to a condition characterized by inappropriate, i.e., decreased or, more commonly, increased, PK catalytic activity, where the particular PK can be an RTK, a CTK or an STK. Inappropriate catalytic activity can arise as the result of either: (1) PK expression in cells which normally do not express PKs, (2) increased PK expression leading to unwanted cell proliferation, differentiation and/or growth, or, (3) decreased PK expression leading to unwanted reductions in cell proliferation, differentiation and/or growth. Increased activity of a PK refers to either amplification of the gene encoding a particular PK or production of a level of PK activity which can correlate with a cell proliferation, differentiation and/or growth disorder (that is, as the level of the PK increases, the severity of one or more of the symptoms of the cellular disorder increases). Decreased activity is, of course, the converse, wherein the severity of one or more symptoms of a cellular disorder increase as the level of the PK activity decreases.

"Treat", "treating" and "treatment" refer to a method of alleviating or abrogating a PK mediated cellular disorder and/or its attendant symptoms. With regard particularly to cancer, these terms simply mean that the life expectancy of an individual affected with a cancer will be increased or that one or more of the symptoms of the disease will be reduced.

"Organism" refers to any living entity comprised of at least one cell. A living organism can be as simple as, for example, a single eukaryotic cell or as complex as a mammal, including a human being.

"Therapeutically effective amount" refers to that amount of the compound being administered which will relieve to some extent one or more of the symptoms of the disorder being treated. In reference to the treatment of cancer, a therapeutically effective amount refers to that amount which has the effect of:

(1) reducing the size of a tumor;
(2) inhibiting (that is, slowing to some extent, preferably stopping) tumor metastasis;

(3) inhibiting to some extent (that is, slowing to some extent, preferably stopping) tumor growth, and/or, (4) relieving to some extent (or, preferably, eliminating) one or more symptoms associated with the cancer.

"Monitoring" means observing or detecting the effect of contacting a compound with a cell expressing a particular PK. The observed or detected effect can be a change in cell phenotype, in the catalytic activity of a PK or a change in the interaction of a PK with a natural binding partner. Techniques for observing or detecting such effects are well-known in the art.

The above-referenced effect is selected from a change or an absence of change in a cell phenotype, a change or absence of change in the catalytic activity of said protein kinase or a change or absence of change in the interaction of said protein kinase with a natural binding partner in a final aspect of this invention.

"Cell phenotype" refers to the outward appearance of a cell or tissue or the biological function of the cell or tissue. Examples, without limitation, of a cell phenotype are cell size, cell growth, cell proliferation, cell differentiation, cell survival, apoptosis, and nutrient uptake and use. Such phenotypic characteristics are measurable by techniques well-known in the art.

"Natural binding partner" refers to a polypeptide that binds to a particular PK in a cell. Natural binding partners can play a role in propagating a signal in a PK-mediated signal transduction process. A change in the interaction of the natural binding partner with the PK can manifest itself as an increased or decreased concentration of the PK/natural binding partner complex and, as a result, in an observable change in the ability of the PK to mediate signal transduction.

"Pro-drugs" means a compound which releases an active parent drug in vivo when administered to a mammalian subject.

Preferred Embodiments

While the broadest definition is set forth in the Summary of the Invention, certain compounds of Formula (I) set forth below are preferred.

(1) A preferred group of compounds of Formula (I) is that wherein $R^1$ and $R^2$ are hydrogen or $R^1$ is hydrogen and $R^2$ is halo, preferably $R^2$ is chloro or fluoro, most preferably fluoro and is located at the 5-position of the indolinone ring.

(2) Another preferred group of compounds is that wherein $R^1$ is hydrogen and $R^2$ is alkoxy, cyano, aryl, —$SO_2R^8$ where $R^8$ is lower alkyl, aryl or heteroaryl, or —$S(O)_2$ $NR^8R^9$ wherein $R^8$ is hydrogen and $R^9$ is hydrogen, aryl, heteroaryl, or lower alkyl, preferably $R^2$ is hydrogen, methoxy, ethoxy, phenyl, phenylsulfonyl, 3-chlorophenylaminosulfonyl, aminosulfonyl, methylaminosulfonyl, dimethylaminosulfonyl, phenylaminosulfonyl, pyridin-3-yl-aminosulfonyl, or isopropylaminosulfonyl and is located at the 5-position of the indolinone ring.

(3) A third preferred group of compounds is that wherein:
$R^3$ is selected from the group consisting of hydrogen, alkyl, aminoalkyl, hydroxyalkyl, aryl, heteroaryl, and —C(O)$R^7$ (wherein $R^7$ is hydroxy, amino, lower alkyl, aminoalkylamino or aryl), more preferably hydrogen, methyl, ethyl, isopropyl, n-, iso- or tert-butyl, phenyl, even more preferably methyl or phenyl, most preferably methyl; and $R^4$ is selected from the group consisting of hydrogen and alkyl, preferably hydrogen, methyl, ethyl, iso-propyl, tert-butyl, iso-butyl, or n-butyl, more preferably methyl.

(4) A fourth more preferred group of compounds is that wherein $R^5$ is:

(i) hydrogen; or (ii) —$COR^{10}$ where $R^{10}$ is —$NR^{11}R^{12}$ where $R^{11}$ is hydrogen or lower alkyl and $R^{12}$ is aminoalkyl wherein the alkyl chain is optionally substituted with hydroxy, more preferably $R^5$ is 3-amino-2-hydroxypropylaminocarbonyl, N-(2-dimethylaminoethyl)aminocarbonyl, N-(2-diethylaminoethyl)-N-methylaminocarbonyl, N-(3-dimethylaminopropyl)aminocarbonyl, N-(2-diethylaminoethyl)aminocarbonyl, N-(3-ethylaminopropyl)aminocarbonyl, N-(3-ethylamino-2-hydroxypropyl)aminocarbonyl, N-(3-diethylaminopropyl)aminocarbonyl, 3-amino-2-hydroxypropylaminocarbonyl, 3-dimethylamino-2-hydroxypropylaminocarbonyl, 3-diethylamino-2-hydroxypropylaminocarbonyl, or N-(3-diethylamino-2-hydroxypropyl)aminocarbonyl, more preferably, N-(2-diethylaminoethyl)aminocarbonyl or N-(ethylaminoethyl) aminocarbonyl; or (iii) —$COR^{10}$ where $R^{10}$ is —$NR^{11}R^{12}$ where $R^{11}$ is hydrogen or lower alkyl and $R^{12}$ is heterocyclylalkyl wherein the alkyl group is optionally substituted with hydroxy, preferably $R^5$ is 3-pyrrolidin-1-yl-propylaminocarbonyl, 3-morpholin-4-ylpropylaminocarbonyl, 2-pyrrolidin-1-ylethylaminocarbonyl, 2-morpholin-4-ylethylaminocarbonyl, 2-(4-methylpiperazin-1-yl)ethyl-aminocarbonyl, 2-(3,5-dimethylpiperazin-1-yl)ethylaminocarbonyl, 2-(3-ethoxycarbonylpiperazin-1-yl)ethylaminocarbonyl, 2-(3-oxopiperazin-1-yl)ethylaminocarbonyl, 2-(imidazolidin-1-yl-2-one)ethylaminocarbonyl, 2-(tetrahydropyrimidin-1-yl-2-one)ethylaminocarbonyl, 2-(2-oxopyrrolidin-1-yl) ethylaminocarbonyl, 3-(4-methyl-piperazin-1-yl) propylaminocarbonyl, 3-(3-ethoxy-carbonylpiperazin-1-yl) propylaminocarbonyl, 3-(3-oxopiperazin-1-yl) propylaminocarbonyl, 3-(imidazolidin-1-yl-2-one)propyl-aminocarbonyl, 3-(tetrahydro-pyrimidin-1-yl-2-one) propylaminocarbonyl, 3-(2-oxopyrrolidin-1-yl) propylaminocarbonyl, 2-(2-oxohomopiperidin-1-yl) ethylamino-carbonyl, 3-(2-oxohomopiperidin-1-yl) propylaminocarbonyl, 3-morpholin-2-hydroxypropylaminocarbonyl, 3-pyrrolidin-1-yl-2-hydroxypropylaminocarbonyl, or 3-(4-methylpiperazin-1-yl)-2-hydroxypropylaminocarbonyl, even more preferably 2-pyrrolidin-1-ylethylaminocarbonyl; or (iv) —$COR^{10}$ where $R^{10}$ is —$NR^{11}R^{12}$ where $R^{11}$ is hydrogen or alkyl and $R^{12}$ is hydroxyalkyl or heteroaralkyl wherein the alkyl group in heteroaralkyl is optionally substituted with one or two hydroxy groups, preferably $R^5$ is 3-hydroxypropylamino-carbonyl, 2-hydroxyethylaminocarbonyl, triazin-1-ylpropyl-aminocarbonyl, triazin-1-ylethyl-aminocarbonyl, 3-imidazol-1-ylpropyl-aminocarbonyl, pyridin-4-ylmethylamino-carbonyl, 3-[1,2,3]-triazol-1-yl-2-hydroxypropyl-aminocarbonyl, 3-[1,2,3]-triazol-2-yl-2-hydroxypropyl-aminocarbonyl, or 2-pyridin-2-ylethylaminocarbonyl; —$COR^{10}$ where $R^{10}$ is heterocycle, preferably a heterocycle of 4 or 6 ring atoms containing one or two nitrogen and optionally an oxygen, more preferably $R^5$ is pyrrolidin-1-ylcarbonyl, piperidin-1-ylcarbonyl, or piperazin-1-ylcarbonyl.

(5) A fifth preferred group of compounds is that wherein $R^6$ is —$OR^{13}$ wherein $R^{13}$ is lower alkyl, trifluoromethyl, carboxyalkyl, aminoalkyl, phosphonooxyalkyl, sulfooxyalkyl, hydroxyalkyl, alkoxyalkyl, aryl, heteroaryl, heteroaralkyl, heterocyclyl, monosaccharides or heterocyclylalkyl wherein the alkyl chain in carboxyalkyl, aminoalkyl, phosphonooxyalkyl, sulfooxyalkyl, heterocyclylalkyl, heteroaralkyl, or alkoxyalkyl is optionally substituted with one or two hydroxy group(s) and further wherein one or two carbon atoms in said alkyl chain are optionally replaced by oxygen, or —NR$^{14}$— (where R$^{14}$ is hydrogen or alkyl), preferably R$^{13}$ is alkyl, aminoalkyl, carboxyalkyl, phosphonooxyalkyl, sulfooxyalkyl, monosaccharides, hydroxyalkyl, alkoxyalkyl and heterocyclylalkyl (wherein the alkyl chain is optionally substituted with one or two hydroxy group(s) and further wherein one or two carbon atoms in said alkyl chain are optionally replaced by oxygen), more preferably methyl, 2-methoxyethyl, 2-(2-methoxyethoxy)ethyl, 2-(2-hydroxyethoxy)ethyl, 2-hydroxyethyl, 3,4,5,6-tetrahydroxy-tetrahydropyran-2-ylmethyl, —(CH$_2$)$_2$OP(O)(OCH$_3$)$_2$, —(CH$_2$)(CHOH)(CH$_2$)OP(O)(OH)$_2$, —(CH$_2$)$_2$OP(O)(OH)$_2$, 2,3-dihydroxypropyl, 2-(diethoxyphosphonooxy)-ethyl, 3-(dimethoxyphosphonooxy)propyl, 3-(diethoxy-phosphono-oxy)-propyl, 3-phosphonooxypropyl, 2-hydroxy-3-(dimethoxy-phosphonooxy)-propyl, 2-hydroxy-3-(diethoxyphosphonooxy)propyl, —(CH$_2$)$_2$OSO$_3$H, —(CH$_2$)$_2$OSO$_3$Na$^+$, —(CH$_2$)$_3$OSO$_3$H, —(CH$_2$)$_3$ OSO$_3$Na$^+$, 2-diethylaminoethyl, carboxymethyl, 2-(2-oxopyrrolidin-1-yl)ethyl, 2-(2,5-dioxopyrrolidin-1-yl)ethyl, 2-carboxy-2-hydroxyethyl, 3-hydroxypropyl, 2-morpholin-4-ylethyl, pyrrolidin-1-ylethyl, pyrrolin-1-yl, 2-hydroxy-3-morpholin-4-ylpropyl, 4-(2-carboxyvinylidene)phenyl, 4-carboxyphenyl, or 2-hydroxy-3-pyrrolidin-1-ylpropyl. Even more preferably R$^{13}$ is 2-dimethoxyphosphonooxy)ethyl, 2-(diethoxyphosphonooxy)ethyl, 2-phosphonooxyethyl, 3-(dimethoxyphosphonooxy)propyl, 3-(diethoxyphosphonooxy)propyl, 3-phosphonooxypropyl, 3-sulfooxypropyl, 2-hydroxy-3-(dimethoxyphosphonooxy)propyl, 2-hydroxy-3-(diethoxyphosphonooxy)propyl, 2-hydroxy-3-phosphonooxypropyl, —(CH$_2$)$_2$OSO$_3$Na$^+$, —(CH$_2$)$_3$OSO$_3$Na$^+$, 2,3-dihydroxypropyl, 2-hydroxyethyl or 3-hydroxypropyl.

(6) A sixth more preferred group of compounds is that wherein R$^6$ is —NR$^{15}$R$^{16}$ where R$^{15}$ and R$^{16}$ are independently selected from the group consisting of hydrogen, alkyl, carboxyalkyl, alkoxyalkyl, aminoalkyl, phosphonooxyalkyl, sulfooxyalkyl, hydroxyalkyl, aryl, heteroaryl, heteroaralkyl, and heterocyclylalkyl; wherein the alkyl chain in carboxyalkyl, aminoalkyl, phosphonooxyalkyl, sulfooxyalkyl, heterocyclylalkyl, heteroaralkyl, hydroxyalkyl, or alkoxyalkyl is optionally substituted with one or two hydroxy group(s) and further wherein one or two carbon atoms in the alkyl chain are optionally replaced by oxygen, —NR$^{17}$— (where R$^{17}$ is hydrogen or alkyl), —S—, or —SO$_2$—; or R$^{15}$ and R$^{16}$ together with the nitrogen atom to which they are attached form saturated or unsaturated heterocycloamino. More preferably, R$^{15}$ is hydrogen, and R$^{16}$ is alkyl, aminoalkyl, carboxyalkyl, phosphonooxyalkyl, sulfooxyalkyl, monosaccharides, hydroxyalkyl, alkoxyalkyl and heterocyclylalkyl (wherein the alkyl chain is optionally substituted with one or two hydroxy group(s) and further wherein one or two carbon atoms in said alkyl chain are optionally replaced by oxygen), even more preferably 2-hydroxy-3-morpholin-4-ylpropyl, pyrolin-1-yl, 5-fluoro-2,4-dioxo-pyrimidin-1-yl, 2-hydroxy-3-pyrrolidin-1-yl-propyl, 2-carboxy-pyrrolidin-1-yl, 2-hydroxy-3-dimethylaminopropyl, 2-hydroxy-3-diethylaminopropyl, 2-hydroxy-3-(4-methylpiperazin-1-yl)propyl, 3-[1,2,3]-triazol-1-yl-2-hydroxypropyl, or 2-hydroxy-3-[1,2,3]-triazol-2-ylpropyl.

(7) Yet another preferred group of compound of represent by Formula (Ia):

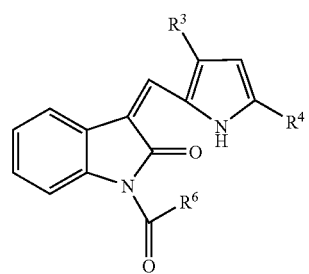

wherein:

R$^3$ is selected from the group consisting of hydrogen, alkyl, —C(O)R$^7$ (where R$^7$ is selected from the group consisting of lower alkyl, amino, hydroxy, alkoxy, aryl, heteroaryl, aryloxy, and heteroaryloxy), or aryl;

R$^4$ is selected from the group consisting of hydrogen, alkyl, or —C(O)R$^7$ (where R$^7$ is as defined above);

R$^6$ is:

(i) —OR$^{13}$ wherein R$^{13}$ is alkyl, trifluoromethyl, carboxyalkyl, aminoalkyl, phosphonooxyalkyl, sulfooxyalkyl, hydroxyalkyl, alkoxyalkyl, aryl, heteroaryl, heteroaralkyl, heterocyclyl, monosaccharides and heterocyclylalkyl wherein the alkyl chain in carboxyalkyl, aminoalkyl, phosphonooxyalkyl, sulfooxyalkyl, heterocyclylalkyl, hydroxyalkyl or alkoxyalkyl is optionally substituted with one or two hydroxy group(s) and further wherein one or two carbon atoms in said alkyl chain are optionally replaced by oxygen, —NR$^4$— (where R$^{14}$ is hydrogen or alkyl), —S—, or —SO$_2$—; or (ii) —NR$^{15}$R$^{16}$ where are R$^{15}$ and R$^{16}$ are independently selected from the group consisting of hydrogen, alkyl, carboxyalkyl, alkoxyalkyl, aminoalkyl, phosphonooxyalkyl, sulfooxyalkyl, hydroxyalkyl, aryl, heteroaryl, heteroaralkyl, and heterocyclylalkyl; wherein the alkyl chain in carboxyalkyl, aminoalkyl, phosphonooxyalkyl, sulfooxyalkyl, hydroxyalkyl, heterocyclylalkyl, or alkoxyalkyl is optionally substituted with one or two hydroxy group(s) and further wherein one or two carbon atoms in the alkyl chain are optionally replaced by oxygen, —NR$^{17}$— (where R$^{17}$ is hydrogen or alkyl), —S—, or —SO$_2$—; or R$^{15}$ and R$^{16}$ together with the nitrogen atom to which they are attached form saturated or unsaturated heterocycloamino; or a pharmaceutically acceptable salt thereof.

Preferably, R$^3$ and R$^4$ are alkyl, more preferably methyl.

Within this group, a more preferred group of compounds is that wherein R$^6$ is —OR$^{13}$ wherein R$^{13}$ is lower alkyl, trifluoromethyl, carboxyalkyl, aminoalkyl, phosphonooxyalkyl, sulfooxyalkyl, hydroxyalkyl, alkoxyalkyl, aryl, heteroaryl, heteroaralkyl, heterocyclyl, monosaccharides or heterocyclylalkyl; wherein the alkyl chain in carboxyalkyl, aminoalkyl, phosphonooxyalkyl, sulfooxyalkyl, heterocyclylalkyl, hydroxyalkyl, heteroaralkyl, or alkoxyalkyl is optionally substituted with one or two hydroxy group(s) and further wherein one or two carbon atoms in said alkyl chain are optionally replaced by oxygen, or —NR$^{14}$— (where R$^{14}$ is hydrogen or alkyl), preferably R$^{13}$ is alkyl, aminoalkyl, carboxyalkyl, phosphonooxyalkyl, sulfooxyalkyl, monosaccharides, hydroxyalkyl, alkoxyalkyl and heterocyclylalkyl (wherein the alkyl chain is optionally substituted with one or two hydroxy group(s) and further wherein one or two carbon atoms in said alkyl chain are optionally replaced by oxygen), more preferably methyl, 2-methoxyethyl, 2-(2-methoxyethoxy)ethyl, 2-(2-hydroxyethoxy)ethyl, 2-hydroxyethyl, 3,4,5,6-tetrahydroxytetrahydropyran-2-ylmethyl, —(CH$_2$)$_2$OP(O)(OCH$_3$)$_2$, —(CH$_2$)(CHOH)(CH$_2$)OP(O)(OH)$_2$, —(CH$_2$)$_2$OP(O)(OH)$_2$, —(CH$_2$)$_2$OSO$_3$H, —(CH$_2$)$_2$OSO$_3$Na$^+$, —(CH$_2$)$_3$OSO$_3$H, —(CH$_2$)$_3$OSO$_3$Na$^+$, 2,3-dihydroxypropyl, 2-(diethoxyphosphonooxy)ethyl, 3-(dimethoxy-phosphonooxy)propyl, 3-(diethoxy-phosphonooxy)-propyl, 3-phosphorylnyloxypropyl, 2-hydroxy-3-(dimethoxy-phosphonooxy)-propyl, 2-hydroxy-3-(diethoxy-phosphonooxy)-propyl, 2-diethylaminoethyl, carboxymethyl, 2-(2-oxopyrrolidin-1-yl)ethyl, 2-(2,5-dioxopyrrolidin-1-yl)ethyl, 2-carboxy-2-hydroxyethyl, 3-hydroxypropyl, 2-morpholin-4-ylethyl, pyrrolidin-1-ylethyl, pyrolin-1-yl, 2-hydroxy-3-morpholin-4-ylpropyl, 4-(2-carboxyvinylidene)phenyl, 4-carboxyphenyl, or 2-hydroxy-3-pyrrolidin-1-ylpropyl. Even more preferably R$^{13}$ is 2-dimethoxyphosphonooxy)ethyl, 2-(diethoxyphosphonooxy)ethyl, 2-phosphonooxyethyl, 3-(dimethoxy-phosphonooxy)propyl, 3-(diethoxyphosphonooxy)propyl, 3-phosphonooxypropyl, —(CH$_2$)$_3$OSO$_3$Na$^+$, 2-hydroxy-3-(dimethoxyphosphonooxy)propyl, 2-hydroxy-3-(diethoxyphosphonooxy)propyl, 2-hydroxy-3-phosphonooxypropyl, 2,3-dihydroxypropyl, 2-hydroxyethyl or 3-hydroxypropyl, most preferably —(CH$_2$)$_3$OSO$_3$Na$^+$.

Within this group, another more preferred group of compounds is that wherein R$^6$ is —NR$^{15}$R$^{16}$ where R$^{15}$ and R$^{16}$ are independently selected from the group consisting of hydrogen, alkyl, carboxyalkyl, alkoxyalkyl, aminoalkyl, phosphonooxyalkyl, sulfooxyalkyl, hydroxyalkyl, aryl, heteroaryl, heteroaralkyl, and heterocyclylalkyl wherein the alkyl chain in carboxyalkyl, aminoalkyl, phosphonooxyalkyl, sulfooxyalkyl, heteroaralkyl, hydroxyalkyl, heterocyclylalkyl or alkoxyalkyl is optionally substituted with one or two hydroxy group(s) and further wherein one or two carbon atoms in the alkyl chain are optionally replaced by oxygen, —NR$^{17}$— (where R$^{17}$ is hydrogen or alkyl), —S—, or —SO$_2$—; or R$^{15}$ and R$^{16}$ together with the nitrogen atom to which they are attached form saturated or unsaturated heterocycloamino. More preferably, R$^{15}$ is hydrogen, and R$^{16}$ is alkyl, aminoalkyl, carboxyalkyl, phosphonooxyalkyl, sulfooxyalkyl, monosaccharides, hydroxyalkyl, alkoxyalkyl, heteroaralkyl, and heterocyclylalkyl (wherein the alkyl chain is optionally substituted with one or two hydroxy group(s) and further wherein one or two carbon atoms in said alkyl chain are optionally replaced by oxygen) or R$^{15}$ and R$^{16}$ together with the nitrogen atom to which they are attached form an unsaturated heterocycloamino, more preferably 2-hydroxy-3-morpholin-4-ylpropyl, pyrolin-1-yl, 5-fluoro-2,4-dioxo-pyrimidin-1-yl, 2-hydroxy-3-pyrrolidin-1-ylpropyl, 2-carboxypyrrolidin-1-yl, 2-hydroxy-3-dimethyl-aminopropyl, 2-hydroxy-3-diethylaminopropyl, 2-hydroxy-3-(4-methylpiperazin-1-yl)propyl, 3-[1,2,3]-triazol-1-yl-2-hydroxypropyl, or 2-hydroxy-3-[1,2,3]-triazol-2-ylpropyl.

Another preferred group of compounds within the group represented by Formula (I) is represented by Formula (Ib):

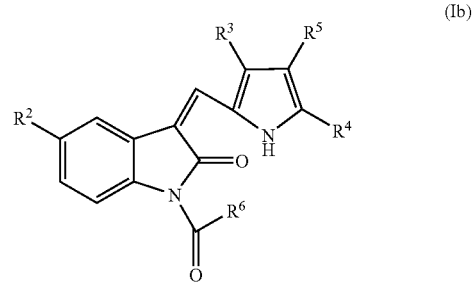

wherein:

R$^2$ is selected from the group consisting of hydrogen, halo, alkyl, alkylthio, nitro, trihalomethyl, hydroxy, alkoxy, cyano, aryl, heteroaryl, —C(O)R$^7$ (where R$^7$ is selected from the group consisting of alkyl, amino, hydroxy, alkoxy, aryl, heteroaryl, aryloxy, and heteroaryloxy), —NR$^8$R$^9$, —NR$^8$C(O)R$^9$, —SO$_2$R$^8$, and —S(O)$_2$NR$^8$R$^9$ (where R$^8$ and R$^9$ are independently selected from the group consisting of hydrogen, alkyl, aryl and heteroaryl);

R$^3$ is selected from the group consisting of hydrogen, alkyl, —C(O)R$^7$ where R$^7$ is selected from the group consisting of alkyl, amino, hydroxy, alkoxy, aryl, heteroaryl, aryloxy, and heteroaryloxy, aryl, and heteroaryl;

R$^4$ is selected from the group consisting of hydrogen, alkyl and —C(O)R$^7$ where R$^7$ is as defined above;

R$^5$ is —COR$^{10}$ where R$^{10}$ is alkyl, alkoxy, hydroxy, aryl, aryloxy, heteroaryl, heterocyle, alkylamino, dialkylamino, or —NR$^{11}$R$^{12}$ where R$^{11}$ is hydrogen or alkyl, and R$^{12}$ is aminoalkyl, dialkylaminoalkyl, heteroarylalkyl, hydroxyalkyl, heteroaralkyl, or heterocyclylalkyl wherein the alkyl chain in alkylamino, heteroaralkyl or heterocylylalkyl is optionally substituted with one or two hydroxy group(s);

R$^6$ is:

(i) —OR$^{13}$ wherein R$^{13}$ is alkyl, trifluoromethyl, carboxyalkyl, aminoalkyl, phosphonooxyalkyl, sulfooxyalkyl, hydroxyalkyl, alkoxyalkyl, aryl, heteroaryl, heteroaralkyl, heterocyclyl, monosaccharides and heterocyclylalkyl wherein the alkyl chain in carboxyalkyl, aminoalkyl, phosphonooxyalkyl, sulfooxyalkyl, heteroaralkyl, hydroxyalkyl or alkoxyalkyl is optionally substituted with one or two hydroxy group(s) and further wherein one or two carbon atoms in said alkyl chain are optionally replaced by oxygen, —NR$^{14}$— (where R$^{14}$ is hydrogen or alkyl), —S—, or —SO$_2$—; or (ii) —NR$^{15}$R$^{16}$ where are R$^{15}$ and R$^{16}$ are independently selected from the group consisting of hydrogen, alkyl, carboxyalkyl, alkoxyalkyl, aminoalkyl, phosphonooxyalkyl, sulfooxyalkyl, hydroxyalkyl, aryl, heteroaryl, heteroaralkyl, and heterocyclylalkyl; wherein the alkyl chain in carboxyalkyl, aminoalkyl, phosphonooxyalkyl, sulfooxyalkyl, hydroxyalkyl, heteroaralkyl or alkoxyalkyl is optionally substituted with one or two hydroxy group(s) and further wherein one or two carbon atoms in the alkyl chain are optionally replaced by oxygen, —NR$^{17}$— (where R$^{17}$ is hydrogen or alkyl), —S—, or —SO$_2$—; or R$^{15}$ and R$^{16}$ together with the nitrogen atom to which they are attached form saturated or unsaturated heterocycloamino; or a pharmaceutically acceptable salt thereof.

With this group a more preferred group of compounds is that wherein:

$R^2$ is halo, preferably fluoro, chloro, or bromo, more preferably fluoro;

$R^3$ is selected from the group consisting of hydrogen, alkyl, —C(O)$R^7$, and aryl, preferably methyl, ethyl, propyl, butyl or phenyl, more preferably methyl;

$R^4$ is selected from the group consisting of hydrogen and alkyl, preferably methyl, ethyl, propyl or butyl, more preferably methyl;

$R^5$ is selected from the group consisting of hydrogen and —COR$^{10}$ where $R^{10}$ is alkyl, alkoxy, hydroxy, aryl, aryloxy, heteroaryl, heterocyle, alkylamino, dialkylamino, or —NR$^{11}$R$^{12}$ where $R^{11}$ is hydrogen or alkyl, and $R^{12}$ is alkylaminoalkyl, dialkylaminoalkyl, heteroarylalkyl, hydroxyalkyl, or heterocyclylalkyl, preferably $R^5$ is:

(i) —COR$^{10}$ where $R^{10}$ is —NR$^{11}$R$^{12}$ where $R^{11}$ is hydrogen or alkyl and $R^{12}$ is aminoalkyl, more preferably $R^5$ is 3-amino-2-hydroxypropylaminocarbonyl, N-(2-dimethylaminoethyl)aminocarbonyl, N-(2-diethylaminoethyl)-N-methylaminocarbonyl, N-(3-dimethylamino-propyl)aminocarbonyl, N-(2-diethylaminoethyl)-aminocarbonyl, N-(3-ethylaminopropyl)aminocarbonyl, N-(3-ethylamino-2-hydroxypropyl)aminocarbonyl, N-(3-diethylamino-propyl) aminocarbonyl, N-(3-diethylamino-2-hydroxypropyl) aminocarbonyl, more preferably , N-(2-diethylaminoethyl) aminocarbonyl; or (ii) —COR$^{10}$ where $R^{10}$ is —NR$^{11}$R$^{12}$ where $R^{11}$ is hydrogen or alkyl and $R^{12}$ is heterocyclylalkyl wherein the alkyl group is optionally substituted with hydroxy, preferably $R^5$ is 3-pyrrolidin-1-yl-propylaminocarbonyl, 3-morpholin-4-ylpropylamino-carbonyl, 2-pyrrolidin-1-ylethylaminocarbonyl, 2-morpholin-4-ylethylaminocarbonyl, 2-(4-methylpiperazin-1-yl)ethyl-aminocarbonyl, 2-(3,5-dimethylpiperazin-1-yl)ethylamino-carbonyl, 2-(3-ethoxycarbonylpiperazin-1-yl)ethylamino-carbonyl, 2-(3-oxopiperazin-1-yl)ethylaminocarbonyl, 2-(imidazolidin-1-yl-2-one)ethylaminocarbonyl, 2-(tetrahydropyrimidin-1-yl-2-one)ethylaminocarbonyl, 2-(2-oxopyrrolidin-1-yl) ethylamino-carbonyl, 3-(4-methyl-piperazin-1-yl) propylaminocarbonyl, 3-(3-ethoxycarbonyl-piperazin-1-yl) propylaminocarbonyl, 3-(3-oxopiperazin-1-yl) propylaminocarbonyl, 3-(imidazolidin-1-yl-2-one) propylaminocarbonyl, 3-(tetrahydropyrimidin-1-yl-2-one) propylaminocarbonyl, 3-(2-oxopyrrolidin-1-yl)propyl-aminocarbonyl, 2-(2-oxohomopiperidin-1-yl)ethylamino-carbonyl, 3-(2-oxohomopiperidin-1-yl) propylaminocarbonyl, 3-amino-2-hydroxypropylaminocarbonyl, 3-morpholin-2-hydroxypropyl-aminocarbonyl, 3-pyrrolidin-2-hydroxypropylaminocarbonyl, 3-dimethylamino-2-hydroxypropylaminocarbonyl, 3-diethylamino-2-hydroxypropylaminocarbonyl, or 3-(4-methylpiperazin-1-yl)-2-hydroxypropylaminocarbonyl, even more preferably 2-pyrrolidin-1-ylethylaminocarbonyl; or (iii) —COR$^{10}$ where $R^{10}$ is —NR$^{11}$R$^{12}$ where $R^{11}$ is hydrogen or alkyl and $R^{12}$ is hydroxyalkyl or heteroarylalkyl wherein the alkyl group in heteroaralky is optionally substituted with one or two hydroxy groups, preferably $R^5$ is 3-hydroxypropylaminocarbonyl, 2-hydroxyethylaminocarbonyl, triazin-1-ylpropyl-aminocarbonyl, triazin-1-ylethyl-aminocarbonyl, 3-imidazol-1-ylpropylaminocarbony, pyridin-4-ylmethylamino-carbonyl, 3-[1,2,3]-triazol-1-yl-2-hydroxypropyl-aminocarbonyl, 3-[1,2,3]-triazol-2-yl-2-hydroxypropyl-aminocarbonyl, or 2-pyridin-2-ylethylamino-carbonyl; or (iv) —COR$^{10}$ where R$^{10}$ is heterocycle, preferably a heterocycle of 4 or 6 ring atoms containing one or two nitrogen and optionally an oxygen, more preferably $R^5$ is pyrrolidin-1-yl, piperidin-1-yl, piperazin-1-yl; and $R^6$ is:

(i) —OR$^{13}$ wherein R$^{13}$ is lower alkyl, trifluoromethyl, carboxyalkyl, aminoalkyl, phosphonooxyalkyl, sulfooxyalkyl, hydroxyalkyl, alkoxyalkyl, aryl, heteroaryl, heteroaralkyl, heterocyclyl, monosaccharides or heterocyclylalkyl wherein the alkyl chain in carboxyalkyl, aminoalkyl, phosphonooxyalkyl, sulfooxyalkyl, heterocyclylalkyl, hydroxyalkyl, heteroaralkyl, or alkoxyalkyl is optionally substituted with one or two hydroxy group(s) and further wherein one or two carbon atoms in said alkyl chain are optionally replaced by oxygen, or —NR$^{14}$— (where R$^{14}$ is hydrogen or alkyl), preferably R$^{13}$ is alkyl, aminoalkyl, carboxyalkyl, phosphonooxyalkyl, sulfooxyalkyl, monosaccharides, hydroxyalkyl, alkoxyalkyl and heterocyclylalkyl (wherein the alkyl chain is optionally substituted with one or two hydroxy group(s) and further wherein one or two carbon atoms in said alkyl chain are optionally replaced by oxygen), more preferably methyl, 2-methoxyethyl, 2-(2-methoxyethoxy)ethyl, 2-(2-hydroxyethoxy)ethyl, 2-hydroxyethyl, 3,4,5,6-tetrahydroxytetrahydropyran-2-ylmethyl, —(CH$_2$)$_2$ OP(O)(OCH$_3$)$_2$, —(CH$_2$)(CHOH)(CH$_2$)OP(O)(OH)$_2$, —(CH$_2$)$_2$OP(O)(OH)$_2$, —(CH$_2$)$_2$OSO$_3$H, —(CH$_2$)$_2$ OSO$_3$Na$^+$, —(CH$_2$)$_3$OSO$_3$H, —(CH$_2$)$_3$OSO$_3$Na$^+$, 2,3-dihydroxypropyl, 2-(diethoxyphosphonooxy)ethyl, 3-(dimethoxy-phosphonooxy)propyl, 3-(diethoxy-phosphonooxy)-propyl, 3-phosphorylnyloxypropyl, 2-hydroxy-3-(dimethoxy-phosphonooxy)-propyl, 2-hydroxy-3-(diethoxy-phosphonooxy)-propyl, 2-diethylaminoethyl, carboxymethyl, 2-(2-oxopyrrolidin-1-yl)ethyl, 2-(2,5-dioxopyrrolidin-1-yl)ethyl, 2-carboxy-2-hydroxyethyl, 3-hydroxypropyl, 2-morpholin-4-ylethyl, pyrrolidin-1-ylethyl, pyrolin-1-yl, 2-hydroxy-3-morpholin-4-ylpropyl, 4-(2-carboxyvinylidene)phenyl, 4-carboxyphenyl, or 2-hydroxy-3-pyrrolidin-1-ylpropyl. Even more preferably R$^{13}$ is 2-dimethoxyphosphonooxy)ethyl, 2-(diethoxyphosphonooxy)ethyl, 2-phosphonooxyethyl, 3-(dimethoxy-phosphonooxy)propyl, 3-(diethoxyphosphonooxy)propyl, 3-phosphonooxypropyl, 2-hydroxy-3-(dimethoxyphosphonooxy)propyl, 2-hydroxy-3-(diethoxyphosphonooxy)propyl, 2-hydroxy-3-phosphonooxypropyl, —(CH$_2$)$_3$ OSO$_3$Na$^+$, 2,3-dihydroxypropyl, 2-hydroxyethyl or 3-hydroxypropyl, most preferably —(CH$_2$)$_3$OSO$_3$Na$^+$; or (ii) —NR$^{15}$R$^{16}$ where are R$^{15}$ and R$^{16}$ R$^{15}$ and R$^{16}$ are independently selected from the group consisting of hydrogen, alkyl, carboxyalkyl, alkoxyalkyl, aminoalkyl, phosphonooxyalkyl, sulfooxyalkyl, hydroxyalkyl, aryl, heteroaryl, heteroaralkyl, and heterocyclylalkyl wherein the alkyl chain in carboxyalkyl, aminoalkyl, phosphonooxyalkyl, sulfooxyalkyl, heteroaralkyl, hydroxyalkyl, heterocyclylalkyl or alkoxyalkyl is optionally substituted with one or two hydroxy group(s) and further wherein one or two carbon atoms in the alkyl chain are optionally replaced by oxygen, —NR$^{17}$— (where R$^{17}$ is hydrogen or alkyl), —S—, or —SO$_2$—; or R$^{15}$ and R$^{16}$ together with the nitrogen atom to which they are attached form saturated or unsaturated heterocycloamino. More preferably, R$^{15}$ is hydrogen, and R$^{16}$ is alkyl, aminoalkyl, carboxyalkyl, phosphonooxyalkyl, sulfooxyalkyl, monosaccharides, hydroxyalkyl, alkoxyalkyl, heteroaralkyl, and heterocyclylalkyl wherein the alkyl chain is optionally substituted with one or two hydroxy group(s) and further wherein one or two carbon atoms in said alkyl chain are optionally replaced by oxygen or R$^{15}$ and R$^{16}$ together with the nitrogen atom to which they are attached form an unsaturated heterocycloamino, more preferably 2-hydroxy-3-morpholin-4-ylpropyl, pyrolin-1-yl, 5-fluoro-2,4-dioxo-pyrimidin-1-yl, 2-hydroxy-3-pyrrolidin-1-ylpropyl, 2-carboxypyrrolidin-1-yl, 2-hydroxy-3-dimethylaminopropyl, 2-hydroxy-3-diethylaminopropyl, 2-hydroxy-3-(4-methylpiperazin-1-yl)propyl, 3-[1,2,3]-triazol-1-yl-2-hydroxypropyl, or 2-hydroxy-3-[1,2,3]-triazol-2-ylpropyl.

Listed below are a representative number of compounds of the present invention:

3-[1-(3,5-Dimethyl-1H-pyrrol-2-yl)-meth-(Z)-ylidene]-2-oxo-2,3-dihydro-indole-1-carboxylic acid 2-morpholin-4-yl-ethyl ester;

3-[1-(3,5-Dimethyl-1H-pyrrol-2-yl)-meth-(Z)-ylidene]-2-oxo-2,3-dihydro-indole-1-carboxylic acid 2-pyrrolidin-1-yl-ethyl ester;

1-{3-[1-(3,5-Dimethyl-1H-pyrrol-2-yl)-meth-(Z)-ylidene]-2-oxo-2,3-dihydro-indole-1-carbonyl}-pyrrolidine-2-carboxylic acid;

3-[1-(3,5-Dimethyl-1H-pyrrol-2-yl)-meth-(Z)-ylidene]-2-oxo-2,3-dihydro-indole-1-carboxylic acid (2-hydroxy-3-morpholin-4-yl-propyl)-amide;

3-[1-(3,5-Dimethyl-1H-pyrrol-2-yl)-meth-(Z)-ylidene]-2-oxo-2,3-dihydro-indole-1-carboxylic acid 2-(2-oxo-pyrrolidin-1-yl)-ethyl ester;

3-[1-(3,5-Dimethyl-1H-pyrrol-2-yl)-meth-(Z)-ylidene]-2-oxo-2,3-dihydro-indole-1-carboxylic acid carboxymethyl ester;

3-[1-(3,5-Dimethyl-1H-pyrrol-2-yl)-meth-(Z)-ylidene]-2-oxo-2,3-dihydro-indole-1-carboxylic acid 2,3-dihydroxypropyl ester;

3-[1-(3,5-Dimethyl-1H-pyrrol-2-yl)-meth-(Z)-ylidene]-2-oxo-2,3-dihydro-indole-1-carboxylic acid 2-hydroxyethyl ester;

3-[1-(3,5-Dimethyl-1H-pyrrol-2-yl)-meth-(Z)-ylidene]-2-oxo-2,3-dihydro-indole-1-carboxylic acid 2-(2-hydroxyethoxy)-ethyl ester;

3-[1-(3,5-Dimethyl-1H-pyrrol-2-yl)-meth-(Z)-ylidene]-2-oxo-2,3-dihydro-indole-1-carboxylic acid 2-(2-methoxyethoxy)-ethyl ester;

3-[1-(3,5-Dimethyl-1H-pyrrol-2-yl)-meth-(Z)-ylidene]-2-oxo-2,3-dihydro-indole-1-carboxylic acid 2-methoxyethyl ester;

3-[1-(3,5-Dimethyl-1H-pyrrol-2-yl)-meth-(Z)-ylidene]-2-oxo-2,3-dihydro-indole-1-carboxylic acid methyl ester;

3-[1-(3,5-Dimethyl-1H-pyrrol-2-yl)-meth-(Z)-ylidene]-1-(imidazole-1-carbonyl)-1,3-dihydro-indol-2-one;

3-[1-(3,5-Dimethyl-1H-pyrrol-2-yl)-meth-(Z)-ylidene]-2-oxo-2,3-dihydro-indole-1-carboxylic acid 2-hydroxy-3-phosphonooxy-propyl ester;

3-[1-(3,5-Dimethyl-1H-pyrrol-2-yl)-meth-(Z)-ylidene]-2-oxo-2,3-dihydro-indole-1-carboxylic acid 3-(dimethoxyphosphonooxy)-propyl ester;

3-[1-(3,5-Dimethyl-1H-pyrrol-2-yl)-meth-(Z)-ylidene]-2-oxo-2,3-dihydro-indole-1-carboxylic acid 3-phosphonooxy-propyl ester;

3-[1-(3,5-Dimethyl-1H-pyrrol-2-yl)-meth-(Z)-ylidene]-2-oxo-2,3-dihydro-indole-1-carboxylic acid 2-(2,5-dioxopyrrolidin-1-yl)ethyl ester;

3-[1-(3,5-Dimethyl-1H-pyrrol-2-yl)-meth-(Z)-ylidene]-2-oxo-2,3-dihydro-indole-1-carboxylic acid 4-carboxyphenyl ester;

3-[1-(3,5-Dimethyl-1H-pyrrol-2-yl)-meth-(Z)-ylidene]-2-oxo-2,3-dihydro-indole-1-carboxylic acid 4-(2-carboxyvinylidene)-phenyl ester;

3-[1-(3,5-Dimethyl-1H-pyrrol-2-yl)-meth-(Z)-ylidene]-2-oxo-2,3-dihydro-indole-1-carboxylic acid 2-hydroxy-2-carboxyethyl ester;

3-[1-(3,5-Dimethyl-1H-pyrrol-2-yl)-meth-(Z)-ylidene]-2-oxo-2,3-dihydro-indole-1-carboxylic acid 2,3,4,5-tetrahydroxypyran-6-ylmethyl ester;

3-[1-(3,5-Dimethyl-1H-pyrrol-2-yl)-meth-(Z)-ylidene]-2-oxo-2,3-dihydro-indole-1-carboxylic acid 2-phosphonooxyethyl ester;

3-[1-(3,5-Dimethyl-1H-pyrrol-2-yl)-meth-(Z)-ylidene]-2-oxo-2,3-dihydro-indole-1-carboxylic acid 2-N,N-diethylaminoethyl ester;

3-[1-(3,5-Dimethyl-1H-pyrrol-2-yl)-meth-(Z)-ylidene]-2-oxo-2,3-dihydro-indole-1-carboxylic acid 3-hydroxypropyl ester;

3-[1-(3,5-Dimethyl-1H-pyrrol-2-yl)-meth-(Z)-ylidene]-2-oxo-2,3-dihydro-indole-1-carboxylic acid 2-(dimethoxyphosphoryloxy)-ethyl ester;

3-[1-(3,5-Dimethyl-1H-pyrrol-2-yl)-meth-(Z)-ylidene]-2-oxo-2,3-dihydro-indole-1-carboxylic acid 3-morpholin-4-yl-2-hydroxypropyl ester;

3-[1-(3,5-Dimethyl-1H-pyrrol-2-yl)-meth-(Z)-ylidene]-2-oxo-2,3-dihydro-indole-1-carboxylic acid 3-pyrrolidin-1-yl-2-hydroxypropyl ester;

3-[1-(3,5-Dimethyl-1H-pyrrol-2-yl)-meth-(Z)-ylidene]-1-(5-fluoro-2,4-dioxopyrimidin-1-ylcarbonyl)-1,3-dihydroindol-2-one; and 3-[1-(3,5-Dimethyl-1H-pyrrol-2-yl)-meth-(Z)-ylidene]-2-oxo-2,3-dihydro-indole-1-carboxylic acid 2-hydroxy-2-sulfooxypropyl ester sodium salt.

General Synthesis

Compounds of this invention can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1–17 (John Wiley and Sons, 1991); Rodd's Chemistry of Carbon Compounds, Volumes 1–5 and Supplementals (Elsevier Science Publishers, 1989); Organic Reactions, Volumes 1–40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

Compounds of Formula (I) can be prepared by following the procedures described below.

Scheme A

Compounds of Formula (I) can be prepared from a compound of Formula (II) as shown in Scheme A below.

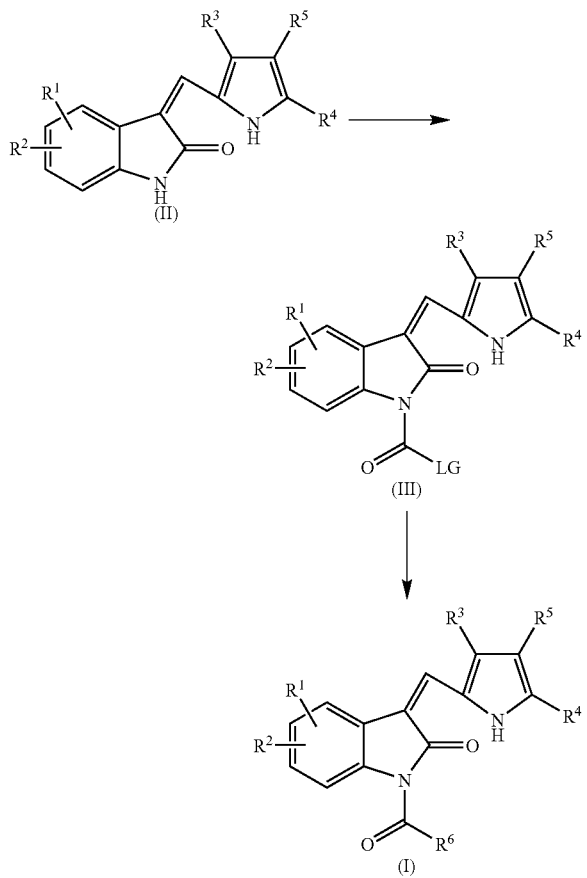

A compound of Formula (I) can be prepared from a 3-(pyrrol-2-ylmethylidene)-2-indolinone of Formula (II) in two steps, as illustrated in Scheme A above.

In step 1, 3-(pyrrol-2-ylmethylidene)-2-indolinone (II) is converted to a compound of formula (III) where LG is a suitable leaving group such halo, imidazol-1-yl, and the like by methods well known in the art. For example, a compound of formula (III) where LG is chloro can be prepared by treatment of (II) with a triphosgene in the presence of an organic amine such as triethylamine, pyridine and the like. A compound of formula (III) where LG is imidazol-1-yl can be prepared by treatment of (II) with carbonyl diimidazole under conditions well known in the art.

Compounds of formula (II) can be prepared by following the procedures described below and in U.S. Pat. No. 5,792,783 and Applicants co-pending application Ser. No., 09/---,---, filed on Feb. 15, 2001, and titled "PYRROLE SUBSTITUTED 2-INDOLINONE PROTEIN KINASE INHIBITORS" the disclose of which is incorporated herein by reference in its entirety.

In step 2, compound (III) is converted to a compound of Formula (I) where $R^6$ is as defined in the Summary of the Invention by methods well known in the art. For example, a compound of Formula (I) where $R^6$ is —$OR^{13}$ or —$NR^{15}R^{16}$ can be prepared by reacting (III) with an alcohol of formula $R^{13}OH$ (where $R^{13}$ is as defined in the Summary of the invention) under esterfication reaction conditions or an amine of formula —$NR^{15}R^{16}$ (where $R^{15}$ and $R^{16}$ are as defined in the Summary of the Invention) under amination reaction conditions respectively. These reaction conditions are well known in the art. For example, the esterfication of (III) is carried out either in neat alcohol or in a suitable organic solvent such as a chlorinated hydrocarbon e.g., methylene chloride, chloroform and the like, ethereal solution such as tetrahydrofuran, ether, and the like, and dimethylformamide and optionally in the presence of an acid such as hydrochloric acid, acetic acid, trifluoroacetic acid, and the like or a base such as pyridine, triethylamine, and the like. The amination is carried out in any of the above solvent. Here the reaction may optionally be carried out in the presence of other non-nucleophilic base such as pyridine, triethylamine and the like especially if the leaving group is a halo. It will be recognized by a person skilled in the art that other suitable solvents can also be used.

Compounds of formula $R^{13}OH$ and —$NR^{15}R^{16}$ are commercially available or they can be prepared by methods well known in the art. For example, 2-methoxyethanol, di-(ethylene glycol) methyl ether, 2-(2-hydroxyethoxy)ethyl, diethylene glycol, diethylene glycolamine, di(ethylene glycol) butylether, glycol, glycerol, 2-amino-1-hexanol, 6-aminohexanol, 2-(tert-butylamino)ethanol, N,N-diethanolamine, glycolic acid, 2-(2-oxopyrrolidin-1-yl)ethanol, 2-(2,5-dioxopyrrolidin-1-yl)ethanol, 4-hydroxycinnamic acid, 4-hydroxybenzoic acid, L- and R-glyceric acid, 1,2,3,4-di-O-isopropylidene-D-glactopyranose, 4-(2-hydroxyethyl)morpholine, 2-pyrrolidin-1-ylethanol, proline, 1-amino-4-morpholin-4-propanol, 3-pyrrolidin-1-ylpropane-1,2-diol, 3-pyrrolidino-1,2-propanediol, 3-(dimethylamino)-1,2-propanediol, 3-(n-benzyl-n-methylamino)-1,2-propanediol, 3-(diethylamino)-1,2-propanediol, 3-phenoxy-1,2-propanediol, mephenesin, 3-methoxy-1,2-propanediol, 3-methoxy-1,2-propanediol, glycerol, 3-morpholino-1,2-propanediol, 3-piperidino-1,2-propanediol, 3-amino-1,2-propanediol, 3-(diisopropylamino)-1,2-propanediol, 3-ethoxy-1,2-propanediol, propranolol hydrochloride, propranolol hydrochloride, propranolol hydrochloride, 1-o-benzyl-rac-glycerol, guaifenesin, glyceryl-p-aminobenzoate, glyceryl-p-aminobenzoate, 3-(4-chlorophenoxy)-1,2-propanediol, 3-(2-methoxybenzyloxy)-1,2-propanediol, 3-(2-methylbenzyloxy)-1,2-propanediol, 1,3-diisopropoxy-2-propanol, n-4-(2,3-dihydroxypropyl)sulfanilamide, 3-(2-ethylphenoxy)-1,2-propanediol, 2,3-diacetin, 1-monobutyrin, calcium glycerophosphate, 3-(4-methoxyphenoxy)-1,2-propanediol, 1,3-dihydroxyacetone dimer, 1,3-dihydroxyacetone dimer, oxprenolol hydrochloride, 1-alpha-phosphatidic acid sodium salt, (S)-(−)-1-benzylglycerol, 2,3-dihydroxypropyl acrylate, 3-methylamino-1,2-propanediol, glycerine carbonate, 2,2-bis-(hydroxymethyl)tetrahydropyran, 6,8-dioxa-1-(hydroxymethyl)bicyclo(3.2.1)octane, 3-mesityloxy-1,2-propanediol, 3-(2-nitroanilino)-1,2-propanediol, 3-benzylamino-propane-1,2-diol, N-ethyl-3-amino-1,2-propanediol, 1-O-propyl-rac-glycerol, monobutyrin, 7,7,9,9-tetramethyl-1,4-dioxa-8-azaspiro[4.5]decane-2-methanol, 1-O-hexyl-rac-glycerol, (S)-(−)-3-tert-butylamino-1,2-propanediol, (2R)-glycerol-O-beta-D-galactopyranoside, galactosyl diglyceride, galactosyl diglyceride, 1-amino-3-phenoxy-2-propanol, 1-phenoxy-3-piperazinopropan-2-ol, (R)-3-t-butylamino-1,2-propanediol, (R)-3-isopropylamino-1,2-propanediol, (S)-3-isopropylamino-1,2-propanediol, 3-(tert-butyl)-5-(hydroxymethyl)-1,3-oxazolan-2-one, (2R)-(−)-1-amino-3-phenoxy-2-propanol, (2S)-(+)-1-amino-3-phenoxy-2-propanol, N-amidino-N-(2,3-dihydroxypropyl)glycine, (S)-

3-amino-1,2-propanediol, (R)-3-amino-1,2-propanediol, 4-hydroxytetrahydroisoxazol-2-ium chloride, tolylaldehyde glyceryl acetal, 2-(aminomethyl)-2-furanmethanol, 2,2-dimethyl-1,3-dioxolane-4-methanamine, 15,16-dihydroxy-4,7,10,13-tetraoxa-hexadecylamine hydrochloride, S-N-3-glycerophospho-ethanolamine, (R)-4-aminomethyl-2,2-dimethyl-1,3-dioxolane, (R)-4-aminomethyl-2,2-dimethyl-1,3-dioxolane, choline, 2-anilinoethanol, N-acetylethanolamine, 2-(tert-butylamino)ethanol, N-allyl-N'-2-hydroxyethylthiourea, N-phenyldiethanolamine, 2-dimethylaminoethanol, N-benzyl-N-methylethanolamine, N-methyldiethanolamine, N-ethyl-N-(2-hydroxyethyl)-m-toluidine, 2-diethylaminoethanol, N-ethyldiethanolamine, N,N-bis(2-hydroxyethyl)-m-chloroaniline, 2-ethoxyethanol, diethylene glycol monomethyl ether, diethylene glycol monomethyl ether, 1-(2-hydroxyethyl)pyrrolidine, N-(2-hydroxyethyl)iminodiacetic acid, 1-aziridineethanol, N-(2-hydroxyethyl)phthalimide, N-(2-hydroxyethyl)piperazine, 1-amino-4-(2-hydroxyethyl)piperazine, 1,4-bis(2-hydroxyethyl)piperazine, HEPES, HEPPS, N-(2-hydroxyethyl)morpholine, 1-piperidineethanol, 2-nitroethanol, 2-hydroxyethylhydrazine, ethanolamine, 2-(diisopropylamino)ethanol, 2-[[2-(dimethylamino)ethyl]methylamino]ethanol, 2-(dibutylamino)ethanol, N-nitrosodiethanolamine, 2-(N-methylanilino)ethanol, 2-(N-methylanilino)ethanol, 2-(N-ethylanilino)ethanol, N-tert-butyldiethanolamine, isopropyldiethanolamine, diethyl bis(2-hydroxyethyl)amino methyl phosphonate, 2-(hexamethyleneimino)ethanol, N-cyclohexylethanolamine, 1-(2-hydroxyethyl)imidazolidine-2-thione, 2-(N-benzyl-N-(2-hydroxyethyl)aminomethyl)-3-hydroxypyridine, 2-(4-sulfanilylanilino)ethanol, 1-(2-hydroxyethyl)-3-(2-methoxy-5-methylphenyl)urea, 2-hydroxyethyl carbazate, 1-(2-hydroxyethyl)-3,4,5,6-tetrahydropyrimidine-2(1h)-thione, DMAE bitartrate, N,N-diethylethanolammonium chloride, N,N-diethylethanolammonium chloride, HEPES sodium salt, N-(2-hydroxyethyl) lactamide, 1-(2-hydroxyethyl)-2-imidazolidinone, N-(2-hydroxyethyl)-2-phenylacetamide, N-(2-hydroxyethyl)-4-cyclohexene-1,2-dicarboximide, N-(2-hydroxyethyl) oxazolidine, 2-(N-methyl-N-isopropylamino)ethanol, 2-(N-methylethylamino)ethanol, N-(β-hydroxyethyl)pyrazole, 2-hydroxyethyl 3-mercaptopropionate, 3-(2-hydroxyethyl)-quinazoline-2,4-dione, ethylene glycol mono-tert-butyl ether, 2-hydroxyethylurea, N-(2-hydroxyethyl)propionamide, 2-isobutoxyethanol, 2-[2-(dimethylamino)ethoxy]ethanol, N-(hydroxyethyl)acetoacetamide, HEPPS sodium salt, 3-(2-hydroxyethylamino)-5,5-dimethyl-2-cyclohexen-1-one, N-(2-hydroxyethyl)succinimide, ethyl N-(2-hydroxyethyl)-carbamate, 2-(dimethylaminomethyl)-3-hydroxy-1-(2-hydroxyethyl)piperidine, 2,6-dimethyl-4-morpholineethanol, 1-(2-hydroxyethyl)-3-(2,4-xylyl)-2-thiourea, 1-ethyl-1-(2-hydroxyethyl)-3-phenylurea, 5-chloro-N-(2-hydroxyethyl)phthalimide, 1-(4-chloro-2-(trifluoromethyl)phenyl)-3-(2-hydroxyethyl)urea, N-methyl-1-phenyl-2,2'-iminodiethanol, 4-(2-hydroxyethyl)-1-lambda-6-,4-thiazinane-1,1-dione, N-cyclohexyl-N'-(2-hydroxyethyl)thiourea, N-cyclopropyl-N'-(2-hydroxyethyl)thiourea, N-benzyl-N'-(2-hydroxyethyl)thiourea, MENAI E627, N-(2'-hydroxyethyl)-3,5-dihydroxybenzamide, N-hydroxyethyl-3-nitrobenzenesulfonamide, 4-nitrotoluenehydroxyethylsulfamide, HEPES sodium salt hydrate, 4-(2-hydroxyethyl)piperazine-1-(2-hydroxypropanesulfonic acid) monohydrate, 2-(1,2,3,4-tetrahydro-2,2,4,7-tetramethyl-1-quinolyl)-1-ethanol, etanidazole, 2-(5-nitro-1-imidazolyl)-1-ethanol, 4-(2-hydroxyethyl)-piperazine-1-carboxylic acid-ethylester, 1-(4-fluorobenzyl)-4-(2-hydroxyethyl)piperazine, 2-[4-(6-chloro-1,3-benzothiazol-2-yl)piperazino]ethan-1-ol, 1-(2-hydroxyethyl)-2-methylimidazole, 2(2-isobutoxyethoxy)ethanol, N-cycloheptyl-N'-(2-hydroxyethyl)thiourea, N-(2-hydroxyethyl)-maleimide, 2-[4-(2-fluorobenzyl)piperazino]ethan-1-ol, 1-(2-hydroxyethyl)piperidine-4-carboxamide, maltitol, D-(+)-turanose, alpha-D-glucoheptose, 3-O-methylglucose, methyl-alpha-D-glucopyranoside, alpha-D-glucose-6-phosphate, monosodium salt, alpha-D-glucose 1-phosphate dipotassium salt dihydrate, and alpha-D-melibiose $H_2O$.

Utility

The compounds of Formula (I) are prodrugs of compounds of Formula (II) that inhibit PKs such as receptor tyrosine kinases (RTKs) and cellular tyrosine kinases (CTKs), and serine-threonine kinases (STKs). The compounds of the present invention are thereofore useful in the treatment of diseases mediated by abnormal PK activity. The PKs whose catalytic activity is modulated by the compounds of this invention include protein tyrosine kinases of which there are two types, receptor tyrosine kinases (RTKs) and cellular tyrosine kinases (CTKs), and serine-threonine kinases (STKs). RTK mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic effects on the extracellular microenvironment, etc.). See, Schlessinger and Ullrich, 1992, *Neuron* 9:303–391.

It has been shown that tyrosine phosphorylation sites on growth factor receptors function as high-affinity binding sites for SH2 (src homology) domains of signaling molecules. Fantl et al., 1992, *Cell* 69:413–423, Songyang et al., 1994, *Mol. Cell. Biol*. 14:2777–2785), Songyang et al., 1993, *Cell* 72:767–778, and Koch et al., 1991, *Science* 252:668–678. Several intracellular substrate proteins that associate with RTKs have been identified. They may be divided into two principal groups: (1) substrates that have a catalytic domain, and (2) substrates which lack such domain but which serve as adapters and associate with catalytically active molecules. Songyang et al., 1993, *Cell* 72:767–778. The specificity of the interactions between receptors and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. Songyang et al., 1993, *Cell* 72:767–778. These observations suggest that the function of each RTK is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

STKs, being primarily cytosolic, affect the internal biochemistry of the cell, often as a down-line response to a PTK event. STKs have been implicated in the signaling process which initiates DNA synthesis and subsequent mitosis leading to cell proliferation.

Thus, PK signal transduction results in, among other responses, cell proliferation, differentiation, growth and metabolism. Abnormal cell proliferation may result in a wide array of disorders and diseases, including the development of neoplasia such as carcinoma, sarcoma, glioblastoma and hemangioma, disorders such as leukemia, psoriasis, arteriosclerosis, arthritis and diabetic retinopathy and other disorders related to uncontrolled angiogenesis and/or vasculogenesis.

A precise understanding of the mechanism by which the compounds of this invention inhibit PKs is not required in order to practice the present invention. However, while not hereby being bound to any particular mechanism or theory, it is believed that the compounds interact with the amino acids in the catalytic region of PKs. PKs typically possess a bilobate structure wherein ATP appears to bind in the cleft between the two lobes in a region where the amino acids are conserved among PKs. Inhibitors of PKs are believed to bind by non-covalent interactions such as hydrogen bonding, van der Waals forces and ionic interactions in the same general region where the aforesaid ATP binds to the PKs. More specifically, it is thought that the 2-indolinone component of the compounds of this invention binds in the general space normally occupied by the adenine ring of ATP. Specificity of a particular molecule for a particular PK may then arise as the result of additional interactions between the various substituents on the 2-indolinone core and the amino acid domains specific to particular PKs. Thus, different indolinone substituents may contribute to preferential binding to particular PKs. The ability to select compounds active at different ATP (or other nucleotide) binding sites makes the compounds of this invention useful for targeting any protein with such a site. The compounds disclosed herein thus have utility in in vitro assays for such proteins as well as exhibiting in vivo therapeutic effects through interaction with such proteins.

Additionally, the compounds of the present invention provide a therapeutic approach to the treatment of many kinds of solid tumors, including but not limited to carcinomas, sarcomas including Kaposi's sarcoma, erythroblastoma, glioblastoma, meningioma, astrocytoma, melanoma and myoblastoma. Treatment or prevention of non-solid tumor cancers such as leukemia are also contemplated by this invention. Indications may include, but are not limited to brain cancers, bladder cancers, ovarian cancers, gastric cancers, pancreas cancers, colon cancers, blood cancers, lung cancers and bone cancers.

Further examples, without limitation, of the types of disorders related to inappropriate PK activity that the compounds described herein may be useful in preventing, treating and studying, are cell proliferative disorders, fibrotic disorders and metabolic disorders.

Cell proliferative disorders, which may be prevented, treated or further studied by the present invention include cancer, blood vessel proliferative disorders and mesangial cell proliferative disorders.

Blood vessel proliferative disorders refer to disorders related to abnormal vasculogenesis (blood vessel formation) and angiogenesis (spreading of blood vessels). While vasculogenesis and angiogenesis play important roles in a variety of normal physiological processes such as embryonic development, corpus luteum formation, wound healing and organ regeneration, they also play a pivotal role in cancer development where they result in the formation of new capillaries needed to keep a tumor alive. Other examples of blood vessel proliferation disorders include arthritis, where new capillary blood vessels invade the joint and destroy cartilage, and ocular diseases, like diabetic retinopathy, where new capillaries in the retina invade the vitreous, bleed and cause blindness.

Two structurally related RTKs have been identified to bind VEGF with high affinity: the fms-like tyrosine 1 (flt-1) receptor (Shibuya et al., 1990, *Oncogene*, 5:519–524; De Vries et al., 1992, *Science*, 255:989–991) and the KDR/FLK-1 receptor, also known as VEGF-R2. Vascular endothelial growth factor (VEGF) has been reported to be an endothelial cell specific mitogen with in vitro endothelial cell growth promoting activity. Ferrara & Henzel, 1989, *Biochein. Biophys. Res. Comm.*, 161:851–858; Vaisman et al., 1990, *J. Biol. Chem.*, 265:19461–19566. Information set forth in U.S. application Ser. Nos. 08/193,829, 08/038,596 and 07/975,750, strongly suggest that VEGF is not only responsible for endothelial cell proliferation, but also is the prime regulator of normal and pathological angiogenesis. See generally, Klagsburn & Soker, 1993, *Current Biology*, 3(10)699–702; Houck, et al., 1992, *J. Biol. Chem.*, 267: 26031–26037.

Normal vasculogenesis and angiogenesis play important roles in a variety of physiological processes such as embryonic development, wound healing, organ regeneration and female reproductive processes such as follicle development in the corpus luteum during ovulation and placental growth after pregnancy. Folkman & Shing, 1992, *J. Biological Chem.*, 267(16):10931–34. Uncontrolled vasculogenesis and/or angiogenesis has been associated with diseases such as diabetes as well as with malignant solid tumors that rely on vascularization for growth. Klagsburn & Soker, 1993, *Current Biology*, 3(10):699–702; Folkham, 1991, *J. Natl. Cancer Inst.*, 82:4–6; Weidner, et al., 1991, *New Engl. J. Med.*, 324:1–5.

The surmised role of VEGF in endothelial cell proliferation and migration during angiogenesis and vasculogenesis indicates an important role for the KDR/FLK-1 receptor in these processes. Diseases such as diabetes mellitus (Folkman, 198, in $XI^{th}$ *Congress of Thrombosis and Haemostasis* (Verstraeta, et al., eds.), pp. 583–596, Leuven University Press, Leuven) and arthritis, as well as malignant tumor growth may result from uncontrolled angiogenesis. See e.g., Folkman, 1971, *N. Engl. J. Med.*, 285:1182–1186. The receptors to which VEGF specifically binds are an important and powerful therapeutic target for the regulation and modulation of vasculogenesis and/or angiogenesis and a variety of severe diseases which involve abnormal cellular growth caused by such processes. Plowman, et al., 1994, *DN&P*, 7(6):334–339. More particularly, the KDR/FLK-1 receptor's highly specific role in neovascularization make it a choice target for therapeutic approaches to the treatment of cancer and other diseases which involve the uncontrolled formation of blood vessels.

Thus, the present invention provides compounds capable of regulating and/or modulating tyrosine kinase signal transduction including KDR/FLK-1 receptor signal transduction in order to inhibit or promote angiogenesis and/or vasculogenesis, that is, compounds that inhibit, prevent, or interfere with the signal transduced by KDR/FLK-1 when activated by ligands such as VEGF. Although it is believed that the compounds of the present invention act on a receptor or other component along the tyrosine kinase signal transduction pathway, they may also act directly on the tumor cells that result from uncontrolled angiogenesis.

Although the nomenclature of the human and murine counterparts of the generic "flk-I" receptor differ, they are, in many respects, interchangeable. The murine receptor, Flk-1, and its human counterpart, KDR, share a sequence homology of 93.4% within the intracellular domain. Likewise, murine FLK-I binds human VEGF with the same affinity as mouse VEGF, and accordingly, is activated by the ligand derived from either species. Millauer et al., 1993, *Cell*, 72:835–846; Quinn et al., 1993, *Proc. Natl. Acad. Sci. USA*, 90:7533–7537. FLK-1 also associates with and subsequently tyrosine phosphorylates human RTK substrates (e.g., PLC-γ or p85) when co-expressed in 293 cells (human embryonal kidney fibroblasts).

Models which rely upon the FLK-1 receptor therefore are directly applicable to understanding the KDR receptor. For example, use of the murine FLK-1 receptor in methods which identify compounds that regulate the murine signal transduction pathway are directly applicable to the identification of compounds which may be used to regulate the human signal transduction pathway, that is, which regulate activity related to the KDR receptor. Thus, chemical compounds identified as inhibitors of KDR/FLK-1 in vitro, can be confirmed in suitable in vivo models. Both in vivo mouse and rat animal models have been demonstrated to be of excellent value for the examination of the clinical potential of agents acting on the KDR/FLK-1 induced signal transduction pathway.

Thus, the present invention provides compounds that regulate, modulate and/or inhibit vasculogenesis and/or angiogenesis by affecting the enzymatic activity of the KDR/FLK-1 receptor and interfering with the signal transduced by KDR/FLK-1. Thus the present invention provides a therapeutic approach to the treatment of many kinds of solid tumors including, but not limited to, glioblastoma, melanoma and Kaposi's sarcoma, and ovarian, lung, mammary, prostate, pancreatic, colon and epidermoid carcinoma. In addition, data suggests the administration of compounds which inhibit the KDR/Flk-1 mediated signal transduction pathway may also be used in the treatment of hemangioma, restenois and diabetic retinopathy.

Furthermore, this invention relates to the inhibition of vasculogenesis and angiogenesis by other receptor-mediated pathways, including the pathway comprising the flt-1 receptor.

Receptor tyrosine kinase mediated signal transduction is initiated by extracellular interaction with a specific growth factor (ligand), followed by receptor dimerization, transient stimulation of the intrinsic protein tyrosine kinase activity and autophosphorylation. Binding sites are thereby created for intracellular signal transduction molecules which leads to the formation of complexes with a spectrum of cytoplasmic signalling molecules that facilitate the appropriate cellular response, e.g., cell division and metabolic effects to the extracellular microenvironment. See, Schlessinger and Ullrich, 1992, *Neuron*, 9:1–20.

The close homology of the intracellular regions of KDR/FLK-1 with that of the PDGF-β receptor (50.3% homology) and/or the related flt-1 receptor indicates the induction of overlapping signal transduction pathways. For example, for the PDGF-β receptor, members of the src family (Twamley et al., 1993, *Proc. Natl. Acad. Sci. USA*, 90:7696–7700), phosphatidylinositol-3'-kinase (Hu et al., 1992, *Mol. Cell. Biol.*, 12:981–990), phospholipase cγ (Kashishian & Cooper, 1993, *Mol. Cell. Biol.*, 4:49–51), ras-GTPase-activating protein, (Kashishian et al., 1992, *EMBO J.*, 11:1373–1382), PTP-ID/syp (Kazlauskas et al., 1993, *Proc. Natl. Acad. Sci. USA*, 10 90:6939–6943), Grb2 (Arvidsson et al., 1994, *Mol. Cell. Biol.*, 14:6715–6726), and the adapter molecules Shc and Nck (Nishimura et al., 1993, *Mol. Cell. Biol.*, 13:6889–6896), have been shown to bind to regions involving different autophosphorylation sites. See generally, Claesson-Welsh, 1994, *Prog. Growth Factor Res.*, 5:37–54. Thus, it is likely that signal transduction pathways activated by KDR/FLK-1 include the ras pathway (Rozakis et al., 1992, *Nature*, 360:689–692), the PI-3'-kinase, the src-mediated and the plcγ-mediated pathways. Each of these pathways may play a critical role in the angiogenic and/or vasculogenic effect of KDR/FLK-1 in endothelial cells. Consequently, a still further aspect of this invention relates to the use of the organic compounds described herein to modulate angiogenesis and vasculogenesis as such processes are controlled by these pathways.

Conversely, disorders related to the shrinkage, contraction or closing of blood vessels, such as restenosis, are also implicated and may be treated or prevented by the methods of this invention.

Fibrotic disorders refer to the abnormal formation of extracellular matrices. Examples of fibrotic disorders include hepatic cirrhosis and mesangial cell proliferative disorders. Hepatic cirrhosis is characterized by the increase in extracellular matrix constituents resulting in the formation of a hepatic scar. An increased extracellular matrix resulting in a hepatic scar can also be caused by a viral infection such as hepatitis. Lipocytes appear to play a major role in hepatic cirrhosis. Other fibrotic disorders implicated include atherosclerosis.

Mesangial cell proliferative disorders refer to disorders brought about by abnormal proliferation of mesangial cells. Mesangial proliferative disorders include various human renal diseases such as glomerulonephritis, diabetic nephropathy and malignant nephrosclerosis as well as such disorders as thrombotic microangiopathy syndromes, transplant rejection, and glomerulopathies. The RTK PDGFR has been implicated in the maintenance of mesangial cell proliferation. Floege et al., 1993, *Kidney International* 43:47S–54S.

Many cancers are cell proliferative disorders and, as noted previously, PKs have been associated with cell proliferative disorders. Thus, it is not surprising that PKs such as, for example, members of the RTK family have been associated with the development of cancer. Some of these receptors, like EGFR (Tuzi et al., 1991, *Br. J. Cancer* 63:227–233, Torp et al., 1992, *APMIS* 100:713–719) HER2/neu (Slamon et al., 1989, *Science* 244:707–712) and PDGF-R (Kumabe et al., 1992, *Oncogene*, 7:627–633) are over-expressed in many tumors and/or persistently activated by autocrine loops. In fact, in the most common and severe cancers these receptor over-expressions (Akbasak and Suner-Akbasak et al., 1992, *J. Neurol. Sci.*, 111:119–133, Dickson et al., 1992, *Cancer Treatment Res.* 61:249–273, Korc et al., 1992, *J. Clin. Invest.* 90:1352–1360) and autocrine loops (Lee and Donoghue, 1992, *J. Cell. Biol.*, 118:1057–1070, Korc et al., supra, Akbasak and Suner-Akbasak et al., supra) have been demonstrated. For example, EGFR has been associated with squamous cell carcinoma, astrocytoma, glioblastoma, head and neck cancer, lung cancer and bladder cancer. HER2 has been associated with breast, ovarian, gastric, lung, pancreas and bladder cancer. PDGFR has been associated with glioblastoma and melanoma as well as lung, ovarian and prostate cancer. The RTK c-met has also been associated with malignant tumor formation. For example, c-met has been associated with, among other cancers, colorectal, thyroid, pancreatic, gastric and hepatocellular carcinomas and lymphomas. Additionally c-met has been linked to leukemia. Over-expression of the c-met gene has also been detected in patients with Hodgkins disease and Burkitts disease.

IGF-IR, in addition to being implicated in nutritional support and in type-II diabetes, has also been associated with several types of cancers. For example, IGF-I has been implicated as an autocrine growth stimulator for several tumor types, e.g. human breast cancer carcinoma cells (Arteaga et al., 1989, *J. Clin. Invest.* 84:1418–1423) and small lung tumor cells (Macauley et al., 1990, *Cancer Res.*, 50:2511–2517). In addition, IGF-I, while integrally involved in the normal growth and differentiation of the nervous system, also appears to be an autocrine stimulator of human gliomas. Sandberg-Nordqvist et al., 1993, *Cancer Res.* 53:2475–2478. The importance of IGF-IR and its ligands in cell proliferation is further supported by the fact that many cell types in culture (fibroblasts, epithelial cells, smooth muscle cells, T-lymphocytes, myeloid cells, chondrocytes and osteoblasts (the stem cells of the bone marrow)) are stimulated to grow by IGF-I. Goldring and Goldring, 1991, *Eukaryotic Gene Expression*, 1:301–326. Baserga and Coppola suggest that IGF-IR plays a central role in the mechanism of transformation and, as such, could be a preferred target for therapeutic interventions for a broad spectrum of human malignancies. Baserga, 1995, *Cancer Res.*, 55:249–252, Baserga, 1994, *Cell* 79:927–930, Coppola et al., 1994, *Mol. Cell. Biol.*, 14:4588–4595.

STKs have been implicated in many types of cancer including, notably, breast cancer (Cance, et al., *Int. J. Cancer*, 54:571–77 (1993)).

The association between abnormal PK activity and disease is not restricted to cancer. For example, RTKs have been associated with diseases such as psoriasis, diabetes mellitus, endometriosis, angiogenesis, atheromatous plaque development, Alzheimer's disease, restenosis, von Hippel-Lindau disease, epidermal hyperproliferation, neurodegenerative diseases, age-related macular degeneration and hemangiomas. For example, EGFR has been indicated in corneal and dermal wound healing. Defects in Insulin-R and IGF-1R are indicated in type-II diabetes mellitus. A more complete correlation between specific RTKs and their therapeutic indications is set forth in Plowman et al., 1994, *DN&P* 7:334–339.

As noted previously, not only RTKs but CTKs including, but not limited to, src, abl, fps, yes, fyn, lyn, lck, blk, hck, fgr and yrk (reviewed by Bolen et al., 1992, *FASEB J.*, 6:3403–3409) are involved in the proliferative and metabolic signal transduction pathway and thus could be expected, and have been shown, to be involved in many PTK-mediated disorders to which the present invention is directed. For example, mutated src (v-src) has been shown to be an oncoprotein ($pp60^{v-src}$) in chicken. Moreover, its cellular homolog, the proto-oncogene $pp60^{c-src}$ transmits oncogenic signals of many receptors. Over-expression of EGFR or HER2/neu in tumors leads to the constitutive activation of $pp60^{c-src}$, which is characteristic of malignant cells but absent in normal cells. On the other hand, mice deficient in the expression of c-src exhibit an osteopetrotic phenotype, indicating a key participation of c-src in osteoclast function and a possible involvement in related disorders.

Similarly, Zap70 has been implicated in T-cell signaling which may relate to autoimmune disorders.

STKs have been associated with inflammation, autoimmune disease, immunoresponses, and hyperproliferation disorders such as restenosis, fibrosis, psoriasis, osteoarthritis and rheumatoid arthritis.

PKs have also been implicated in embryo implantation. Thus, the compounds of this invention may provide an effective method of preventing such embryo implantation and thereby be useful as birth control agents. Additional disorders which may be treated or prevented using the compounds of this invention are immunological disorders such as autoimmune disease, AIDS and cardiovasular disorders such as atherosclerosis.

Finally, both RTKs and CTKs are currently suspected as being involved in hyperimmune disorders.

Administration and Pharmaceutical Composition

A compound of the present invention or a pharmaceutically acceptable salt thereof, can be administered as such to a human patient or can be administered in pharmaceutical compositions in which the foregoing materials are mixed with suitable carriers or excipient(s). Techniques for formulation and administration of drugs may be found in "Remington's Pharmacological Sciences," Mack Publishing Co., Easton, Pa., latest edition.

As used herein, "administer" or "administration" refers to the delivery of a compound of Formula (I) or a pharmaceutically acceptable salt thereof or of a pharmaceutical composition containing a compound of Formula (I) or a pharmaceutically acceptable salt thereof of this invention to an organism for the purpose of prevention or treatment of a PK-related disorder.

Suitable routes of administration may include, without limitation, oral, rectal, transmucosal or intestinal administration or intramuscular, subcutaneous, intramedullary, intrathecal, direct intraventricular, intravenous, intravitreal, intraperitoneal, intranasal, or intraocular injections. The preferred routes of administration are oral and intravenous.

Alternatively, one may administer the compound in a local rather than systemic manner, for example, via injection of the compound directly into a solid tumor, often in a depot or sustained release formulation.

Furthermore, one may administer the drug in a targeted drug delivery system, for example, in a liposome coated with tumor-specific antibody. The liposomes will be targeted to and taken up selectively by the tumor.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the compounds of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylmethyl-cellulose, sodium carboxymethylcellulose, and/or polyvinyl-pyrrolidone (PVP). If desired, disintegrating agents may be added, such as cross-linked polyvinyl pyrrolidone, agar, or alginic acid. A salt such as sodium alginate may also be used.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, or liquid polyethylene glycols. Stabilizers may be added in these formulations, also.

Pharmaceutical compositions which may also be used include hard gelatin capsules. As a non-limiting example, the active compound capsule oral drug product formulation may be as 50 and 200 mg dose strengths (formulation codes J-011248-AA-00 and J-011248-AA-01, respectively). The two dose strengths are made from the same granules by filling into different size hard gelatin capsules, size 3 for the 50 mg capsule and size 0 for the 200 mg capsule. The composition of the formulation may be, for example, as indicated in Table 1.

TABLE 1

| Ingredient Name/Grade | Concentration in Granulation (% w/w) | Amount in 50 mg Capsule (mg) | Amount in 200 mg Capsule (mg) |
|---|---|---|---|
| Formulation Code | J-011248-AA | J-011248-AA-00 | J-011248-AA-01 |
| Active Compound NF | 65.0 | 50.0 | 200.0 |
| Mannitol NF | 23.5 | 18.1 | 72.4 |
| Croscarmellose sodium NF | 6.0 | 4.6 | 18.4 |
| Povidone K 30 NF | 5.0 | 3.8 | 15.2 |
| Magnesium stearate NF | 0.5 | 0.38 | 1.52 |
| Capsule, Swedish yellow NF | | Size 3 | Size 0 |

The capsules may be packaged into brown glass or plastic bottles to protect the active compound from light. The containers containing the active compound capsule formulation must be stored at controlled room temperature (15–30° C.).

For administration by inhalation, the compounds for use according to the present invention are conveniently delivered in the form of an aerosol spray using a pressurized pack or a nebulizer and a suitable propellant, e.g., without limitation, dichlorodifluoromethane, trichlorofluoromethane, dichlorotetra-fluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds may also be formulated for parenteral administration, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

Pharmaceutical compositions for parenteral administration include aqueous solutions of a water soluble form, such as, without limitation, a salt, of the active compound.

Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use.

The compounds may also be formulated in rectal compositions such as suppositories or retention enemas, using, e.g., conventional suppository bases such as cocoa butter or other glycerides.

In addition to the fomulations described previously, the compounds may also be formulated as depot preparations. Such long acting formulations may be administered by implantation (for example, subcutaneously or intramuscularly) or by intramuscular injection. A compound of this invention may be formulated for this route of administration with suitable polymeric or hydrophobic materials (for instance, in an emulsion with a pharamcologically acceptable oil), with ion exchange resins, or as a sparingly soluble derivative such as, without limitation, a sparingly soluble salt.

A non-limiting example of a pharmaceutical carrier for the hydrophobic compounds of the invention is a cosolvent system comprising benzyl alcohol, a nonpolar surfactant, a water-miscible organic polymer and an aqueous phase such as the VPD co-solvent system. VPD is a solution of 3% w/v benzyl alcohol, 8% w/v of the nonpolar surfactant Polysorbate 80, and 65% w/v polyethylene glycol 300, made up to volume in absolute ethanol. The VPD co-solvent system (VPD:D5W) consists of VPD diluted 1:1 with a 5% dextrose in water solution. This co-solvent system dissolves hydrophobic compounds well, and itself produces low toxicity upon systemic administration. Naturally, the proportions of such a co-solvent system may be varied considerably without destroying its solubility and toxicity characteristics. Furthermore, the identity of the co-solvent components may be varied: for example, other low-toxicity nonpolar surfactants may be used instead of Polysorbate 80, the fraction size of polyethylene glycol may be varied, other biocompatible polymers may replace polyethylene glycol, e.g., polyvinyl pyrrolidone, and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. In addition, certain organic solvents such as dimethylsulfoxide also may be employed, although often at the cost of greater toxicity.

Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions herein also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Many of the PK modulating compounds of the invention may be provided as physiologically acceptable salts wherein the claimed compound may form the negatively or the positively charged species. Examples of salts in which the compound forms the positively charged moiety include, without limitation, quaternary ammonium (defined elsewhere herein), salts such as the hydrochloride, sulfate, carbonate, lactate, tartrate, malate, maleate, succinate wherein the nitrogen atom of the quaternary ammonium group is a nitrogen of the selected compound of this invention which has reacted with the appropriate acid. Salts in which a compound of this invention forms the negatively charged species include, without limitation, the sodium, potassium, calcium and magnesium salts formed by the reaction of a carboxylic acid group in the compound with an appropriate base (e.g. sodium hydroxide (NaOH), potassium hydroxide (KOH), calcium hydroxide ($Ca(OH)_2$), etc.).

Pharmaceutical compositions suitable for use in the present invention include compositions wherein the active ingredients are contained in an amount sufficient to achieve the intended purpose, e.g., the modulation of PK activity or the treatment or prevention of a PK-related disorder.

More specifically, a therapeutically effective amount means an amount of compound effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any compound used in the methods of the invention, the therapeutically effective amount or dose can be estimated initially from cell culture assays. Then, the dosage can be formulated for use in animal models so as to achieve a circulating concentration range that includes the $IC_{50}$ as determined in cell culture (i.e., the concentration of the test compound which achieves a half-maximal inhibition of the PK activity). Such information can then be used to more accurately determine useful doses in humans.

Toxicity and therapeutic efficacy of the compounds described herein can be determined by standard pharmaceutical procedures in cell cultures or experimental animals, e.g., by determining the $IC_{50}$ and the $LD_{50}$ (both of which are discussed elsewhere herein) for a subject compound. The data obtained from these cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to provide plasma levels of the active species which are sufficient to maintain the kinase modulating effects. These plasma levels are referred to as minimal effective concentrations (MECs). The MEC will vary for each compound but can be estimated from in vitro data, e.g., the concentration necessary to achieve 50–90% inhibition of a kinase may be ascertained using the assays described herein. Dosages necessary to achieve the MEC will depend on individual characteristics and route of administration. HPLC assays or bioassays can be used to determine plasma concentrations.

Dosage intervals can also be determined using MEC value. Compounds should be administered using a regimen that maintains plasma levels above the MEC for 10–90% of the time, preferably between 30–90% and most preferably between 50–90%.

At present, the therapeutically effective amounts of compounds of Formula (I) may range from approximately 25 mg/m$^2$ to 1500 mg/m$^2$ per day; preferably about 3 mg/m$^2$/day. Even more preferably 50 mg/qm qd to 400 mg/qd.

In cases of local administration or selective uptake, the effective local concentration of the drug may not be related to plasma concentration and other procedures known in the art may be employed to determine the correct dosage amount and interval.

The amount of a composition administered will, of course, be dependent on the subject being treated, the severity of the affliction, the manner of administration, the judgment of the prescribing physician, etc.

The compositions may, if desired, be presented in a pack or dispenser device, such as an FDA approved kit, which may contain one or more unit dosage forms containing the active ingredient. The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes, and the like.

It is also an aspect of this invention that a compound described herein might be combined with other chemotherapeutic agents for the treatment of the diseases and disorders discussed above. For instance, a compound, salt or prodrug of this invention might be combined with alkylating agents such as fluorouracil (5-FU) alone or in further combination with leukovorin; or other alkylating agents such as, without limitation, other pyrimidine analogs such as UFT, capecitabine, gemcitabine and cytarabine, the alkyl sulfonates, e.g., busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethiophosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilm's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma).

A compound of this invention can also be used in combination with other antimetabolite chemotherapeutic agents such as, without limitation, folic acid analogs, e.g. methotrexate (used in the treatment of acute lymphocytic leukemia, choriocarcinoma, mycosis fungiodes breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias.

It is contemplated that a compound of this invention can also be used in combination with natural product based chemotherapeutic agents such as, without limitation, the vinca alkaloids, e.g., vinblastin (used in the treatment of breast and testicuiar cancer), vincristine and vindesine; the epipodophylotoxins, e.g., etoposide and teniposide, both of which are useful in the treatment of testicular cancer and Kaposi's sarcoma; the antibiotic chemotherapeutic agents, e.g., daunorubicin, doxorubicin, epirubicin, mitomycin (used to treat stomach, cervix, colon, breast, bladder and pancreatic cancer), dactinomycin, temozolomide, plicamycin, bleomycin (used in the treatment of skin, esophagus and genitourinary tract cancer); and the enzymatic chemotherapeutic agents such as L-asparaginase.

In addition to the above, a compound of this invention could also be used in combination with the platinum coordination complexes (cisplatin, etc.); substituted ureas such as hydroxyurea; methylhydrazine derivatives, e.g., procarbazine; adrenocortical suppressants, e.g., mitotane, aminoglutethimide; and hormone and hormone antagonists such as the adrenocorticosteriods (e.g., prednisone), progestins (e.g., hydroxyprogesterone caproate); estrogens (e.g., diethylstilbesterol); antiestrogens such as tamoxifen; androgens, e.g., testosterone propionate; and aromatase inhibitors such as anastrozole.

Finally, it is also contemplated that the combination of a compound of this invention will be effective in combination with mitoxantrone or paclitaxel for the treatment of solid tumor cancers or leukemias such as, without limitation, acute myelogenous (non-lymphocytic) leukemia. The compounds of this invention can also be used with a COX-2 inhibitor.

EXAMPLES

The following preparations and examples are given to enable those skilled in the art to more clearly understand and to practice the present invention. They should not be considered as limiting the scope of the invention, but merely as being illustrative and representative thereof.

Synthetic Examples

Example 1

Synthesis of 3-[1-(3,5-dimethyl-1H-pyrrol-2-yl)-meth-(Z)-ylidene]-2-oxo-2,3-dihydro-indole-1-carbonyl chloride To the solution of triphosgene (7.2 gram, 24.2 mmol) in 500 mL of anhydrous THF was added 56 mL of thiethylamine in one portion and the resulting mixture was stirred at room temperature for 10 minutes. Solid 3-[1-(3,5-dimethyl-1H-pyrro-2-yl)-meth-(Z)-ylidene]-2-oxo-2,3-dihydro-indole (5.768 gram, 24.2 mmol) was added in one portion to the above mixture. The reaction mixture was stirred at room temperature for 1 h and then cooled on ice bath to 0–4° C. Ice-cold 4M HCl aq. (1.5 L) was added in one portion upon vigorous stirring. The resulting suspension was further stirred for 10 min., and filtered. The solid was washed with ice-cold 4M HCl aq. and dried on the high vacuum oven overnight. The crude product was recrystallized from anhydrous benzene and filtered. The solid was then washed with cyclohexane and dried in a vacuum oven overnight to yield 3-[1-(3,5-dimethyl-1H-pyrrol-2-yl)-meth-(Z)-ylidene]-2-oxo-2,3-dihydro-indole-1-carbonyl chloride (5.531 gram, 76%). $^1$HNMR (400 MHz, DMSO-d6) δ 12.41 (s, br, 1H), 7.98 (m, 1H), 7.52 (m, 1H), 7.43 (s, 1H), 7.25 (m, 1H), 6.08 (d, br, J=2 Hz, 1H), 2.43 (s, 3H), 2.36 (s, 3H).

Example 2

Synthesis of 3-[1-(3,5-dimethyl-1H-pyrrol-2-yl)-meth-(Z)-ylidene]-1-(imidazol-1-ylcarbonyl)-1,3-dihydro-indol-2-one A reaction mixture of 3-[1-(3,5-dimethyl-1H-pyrrol-2-yl)-meth-(Z)-ylidene]-2-oxo-2,3-dihydro-indole (1.0 gram, 4.2 mmol) and CDI (1.36 gram 8.4 mmol) in DMF was stirred at room temperature for 2 h and filtered. The precipitate was washed with DMF and dried in a high vacuum oven to give 1.25 gram (89%) of 3-[1-(3,5-dimethyl-1H-pyrrol-2-yl)-meth-(Z)-ylidene]-1-(imidazol-1-ylcarbonyl)-1,3-dihydro-indol-2-one as an orange solid. $^1$HNMR (400 MHz, DMSO-d6) δ 12.23 (s, 1H, NH-1'), 8.45 (s, 1H), 7.94 (m, 1H), 7.79 (m, 1H), 7.73 (s, 1H, H-vinyl), 7.46 (m, 1H), 7.25 (m, 2H), 7.13 (m, 1H), 6.14 (d, J=1.95 Hz, 1H, H-4'), 2.36 (s, 3H, CH3), and 2.32 (s, 3H, CH3). MS m/z (relative intensity, %) 332 (100, M$^+$.)

Example 3

Synthesis of 3-[1-(3,5-dimethyl-1H-pyrrol-2-yl)-meth-(Z)-ylidene]-2-oxo-2,3-dihydro-indole-1-carboxylic acid methyl ester A reaction mixture of 3-[1-(3,5-dimethyl-1H-pyrrol-2-yl)-meth-(Z)-ylidene]-1-(imidazole-1-ylcarbonyl)-1,3-dihydro-indol-2-one (5.3 mg, 0.016 mmol) in 1.0 mL of methanol was stirred at room temperature for 64 h and filtered. The red solid was washed with methanol and dried in a vacuum oven overnight to afford 3-[1-(3,5-dimethyl-1H-pyrrol-2-yl)-meth-(Z)-ylidene]-2-oxo-2,3-dihydro-indole-1-carboxylic acid methyl ester (3.0 mg, 63%) as a red solid. $^1$H NMR (400 MHz, DMSO-d6) d 12.63 (s, 1H, NH-1'), 7.84–7.86 (m, 1H), 7.69 (s, 1H, H-vinyl), 7.56–7.68 (m, 1H), 7.19–7.22 (m, 2H), 6.06 (d, J=2.34 Hz, 1H, H-4'), 4.08 (s, 3H, OCH$_3$), 2.40 (s, 3H, CH$_3$), and 2.36 (s, 3H, CH$_3$). MS m/z (relative intensity, %) 297 (100, [M+1]$^+$.)

Example 4

Synthesis of 3-[1-(3,5-dimethyl-1H-pyrrol-2-yl)-meth-(Z)-ylidene]-2-oxo-2,3-dihydro-indole-1-carboxylic acid 2-methoxy-ethyl ester A reaction mixture of 3-[1-(3,5-dimethyl-1H-pyrrol-2-yl)-meth-(Z)-ylidene]-1-(imidazol-1-ylcarbonyl)-1,3-dihydro-indol-2-one (200 mg, 0.6 mmol) in 6 mL of 2-methoxy-ethanol was stirred at room temperature for 20 h and partitioned between water and dichloromethane. The organic layer was dried over anhydrous magnesium sulfate and concentrated. The residue was purified on a silica gel column eluting with ethyl acetate-hexane (1:3) to give 3-[1-(3,5-dimethyl-1H-pyrrol-2-yl)-meth-(Z)-ylidene]-2-oxo-2,3-dihydro-indole-1-carboxylic acid 2-methoxy-ethyl ester (63 mg, 31%) as an red solid. $^1$H NMR (400 MHz, CDCl$_3$) δ 12.71 (s, 1H, NH-1'), 7.85 (d, J=7.05 Hz, 1H), 7.50 (d, J=7.05 Hz, 1H), 7.40 (s, 1H, H-vinyl), 7.16–7.23 (m, 2H), 6.03 (s, br, 1H, H-4'), 4.62 (t, J=4.70 Hz, 2H, CH$_2$), 3.81 (t, J=4.70 Hz, 2H, CH$_2$), 2.38 (s, 3H, CH$_3$), and 2.34 (s, 3H, CH$_3$). MS m/z (relative intensity, %) 341 (100, [M+1]$^+$.).

Example 5

Synthesis of 3-[1-(3,5-dimethyl-1H-pyrrol-2-yl)-meth-(Z)-ylidene]-2-oxo-2,3-dihydro-indole-1-carboxylic acid 2-(2-methoxy-ethoxy)-ethyl ester A reaction mixture of 3-[1-(3,5-dimethyl-1H-pyrrol-2-yl)-meth-(Z)-ylidene]-1-(imidazol-1-ylcarbonyl)-1,3-dihydro-indol-2-one (50 mg, 0.15 mmol) and 1.0 mL of di(ethylene glycol) methyl ether in 1.0 mL of dichloromethane was stirred at 38 C for 20 h and concentrated. The residue was purified on a silica gel column eluting with ethyl acetate-hexane to afford (27 mg, 47%) of 3-[1-(3,5-dimethyl-1H-pyrrol-2-yl)-meth-(Z)-ylidene]-2-oxo-2,3-dihydro-indole-1-carboxylic acid 2-(2-methoxy-ethoxy)-ethyl ester. $^1$H NMR (400 MHz, CDCl$_3$) δ 12.72 (s, 1H, NH-1'), 7.86 (d, J=7.62 Hz, 1H), 7.50 (d, J=7.62 Hz, 1H), 7.40 (s, 1H, H-vinyl), 7.19–7.26 (m, 2H), 6.03 (s, br, 1H, H-4'), 4.63 (t, J=4.69 Hz, 2H, CH$_2$), 3.92 (t, J=4.69 Hz, 2H, CH$_2$), 3.75 (t, J=4.62 Hz, 2H, CH$_2$), 3.60 (t, J=4.62 Hz, 2H, CH$_2$), 2.38 (s, 3H, CH$_3$), and 2.34 (s, 3H, CH$_3$). MS m/z (relative intensity, %) 385 (100, [M+1]$^+$.).

Example 6

Synthesis of 3-[1-(3,5-dimethyl-1H-pyrrol-2-yl)-meth-(Z)-ylidene]-2-oxo-2,3-dihydro-indole-1-carboxylic acid 2-(2-hydroxy-ethoxy)-ethyl ester 3-[1-(3,5-Dimethyl-1H-pyrrol-2-yl)-meth-(Z)-ylidene]-2-oxo-2,3-dihydro-indole-1-carboxylic acid 2-(2-hydroxy-ethoxy)-ethyl ester was prepared using the same procedure described in Example 5 above except substituting di(ethylene glycol) methyl ether with 2-(2-hydroxyethoxy)ethanol a yield of 36%. $^1$H NMR (400 MHz, CDCl$_3$) δ 12.64 (s, 1H, NH-1'), 7.90 (d, J=7.43 Hz, 1H), 7.50 (d, J=7.43 Hz, 1H), 7.41 (s, 1H, H-vinyl), 7.19–7.26 (m, 2H), 6.03 (s, br, 1H, H-4'), 4.62 (t, J=4.50 Hz, 2H, CH$_2$), 3.93 (t, J=4.50 Hz, 2H, CH$_2$), 3.71–3.80 (m, 4H, 2×CH$_2$), 2.79 (t, J=6.25 Hz, 1H, OH), 2.40 (s, 3H, CH$_3$), and 2.34 (s, 3H, CH$_3$). MS m/z (relative intensity, %) 371 (100, [M+1]$^+$.).

Example 7

Synthesis of 3-[1-(3,5-dimethyl-1H-pyrrol-2-yl)-meth-(Z)-ylidene]-2-oxo-2,3-dihydro-indole-1-carboxylic acid 2-hydroxy-ethyl ester A reaction mixture of 3-[1-(3,5-dimethyl-1h-pyrrol-2-yl)-meth-(z)-ylidene]-1-(imidazol-1-ylcarboxnyl)-1,3-dihydro-indole-2-one (116 mg, 0.5 mmol), ethylene glycol (124 mg, 2 mmol), and acetic acid (120 mg, 2 mmol) in THF was stirred at room temperature for 60 h. The precipitate was filtered and washed with ethyl acetate and dried in a vacuum oven to afford 41 mg (25%) of 3-[1-(3,5-dimethyl-1H-pyrrol-2-yl)-meth-(Z)-ylidene]-2-oxo-2,3-dihydro-indole-1-carboxylic acid 2-hydroxy-ethyl ester $^1$H NMR (400 MHz, CDCl$_3$) δ 12.59 (s, 1H, NH-1'), 7.84–7.86 (m, 1H), 7.48–7.50 (m, 1H), 7.39 (s, 1H, H-vinyl), 7.17–7.20 (m, 2H), 6.04 (d, J=2.35 Hz, 1H, H-4'), 4.60 (t, J=4.50 Hz, 2H, CH$_2$CH$_2$OH), 2.91–2.94 (m, 2H, CH$_2$CH$_2$OH), 2.92 (t, J=6.26 Hz, 1H, CH$_2$CH$_2$OH), 2.40 (s, 3H, CH$_3$), and 2.34 (s, 3H, CH$_3$). MS m/z (relative intensity, %) 327 (100, [M+1]$^+$.).

Example 8

Synthesis of 3-[1-(3,5-dimethyl-1H-pyrrol-2-yl)-meth-(Z)-ylidene]-2-oxo-2,3-dihydro-indole-1-carboxylic acid 2-phosphonooxyethyl ester To a suspension of 3-[1-(3,5-dimethyl-1H-pyrrol-2-yl)-meth-(Z)-ylidene]-2-oxo-2,3-dihydro-indole-1-carboxylic acid 2-hydroxy-ethyl ester (163.2 mg, 0.5 mmol) in 0.4 mL of pyridine and 5.0 mL of dichloromethane was added dimethyl chlorophosphate and the reaction mixture was stirred at room temperature for 20 h and concentrated. The residue was then purified by silica gel chromatography eluting with ethyl acetate-hexane (1:3), THF-dichloromethane (1:2.5), and THF-acetone-dichloromethane (1:1:2) sequentially to afford 88 mg (41%) of 3-[1-(3,5-dimethyl-1H-pyrrol-2-yl)-meth-(Z)-ylidene]-2-oxo-2,3-dihydro-indole-1-carboxylic acid 2-(dimethoxy-phosphonooxy)-ethyl ester. $^1$H NMR (400 MHz, CDCl$_3$) δ 12.64 (s, br, 1H, NH-1'), 7.83–7.86 (m, 1H, H-4), 7.49–7.52 (m, 1H, H-7), 7.41 (s, 1H, H-vinyl), 7.19–7.23 (m, 2H, H-5, 6), 6.04 (d, J=1.95 Hz, 1H, H-4'), 4.69–4.71 (m, 2H, NCOOCH$_2$CH$_2$OPO(OCH$_3$)$_2$-1), 4.44–4.48 (m, 2H, NCOOCH$_2$CH$_2$OPO(OCH$_3$)$_2$-1), 3.81 (s, 3H, NCOOCH$_2$CH$_2$OPO(OCH$_3$)$_2$-1), 3.78 (s, 3H, NCOOCH$_2$CH$_2$OPO(OCH$_3$)$_2$-1), 2.39 (s, 3H, CH$_3$), and 2.35 (s, 3H, CH$_3$). MS m/z (relative intensity, %) 435 (100, [M+1]$^+$.). $^{13}$P NMR (162 MHz, CDCl$_3$) δ 2.22.

Example 9

Synthesis of 3-[1-(3,5-dimethyl-1H-pyrrol-2-yl)-meth-(Z)-ylidene]-2-oxo-2,3-dihydro-indole-1-carboxylic acid 2,3-dihydroxy-propyl ester A reaction mixture of 3-[1-(3,5-dimethyl-1h-pyrrol-2-yl)-meth-(z)-ylidene]-1-(imidazol-1-ylcarboxnyl)-1,3-dihydro-indole-2-one (166 mg, 0.5 mmol), glycerol (138 mg, 1.5 mmol), TFA (68 mg, 0.6 mmol) in 3.0 mL of THF and 0.3 mL of DMF was stirred at room temperature for 3 h and concentrated. The residue was then triturated with ether to obtain 35 mg (20%) of 3-[1-(3,5-dimethyl-1H-pyrrol-2-yl)-meth-(Z)-ylidene]-2-oxo-2,3-dihydro-indole-1-carboxylic acid 2,3-dihydroxy-propyl ester.

Alternative Procedure

To the solution of glycerol (460 mg, 2.5 mmol) in 1.0 mL of pyridine and 2.0 mL of THF was added a suspension of 3-[1-(3,5-dimethyl-1H-pyrrol-2-yl)-meth-(Z)-ylidene]-2-oxo-2,3-dihydro-indole-1-carbonyl chloride in 2.0 mL of THF at 0° C. The reaction mixture was gradually warmed to room temperature, stirred for 2.5 h, and concentrated. The residue was triturated with ethyl acetate and filtered. The solid was then washed with ethyl acetate, water, ether, and dried to yield 87 mg of 3-[1-(3,5-dimethyl-1H-pyrrol-2-yl)-meth-(Z)-ylidene]-2-oxo-2,3-dihydro-indole-1-carboxylic acid 2,3-dihydroxy-propyl ester. The combined filtrate was concentrated and partitioned between water and ethyl acetate. The organic layer was washed with brine, dried over anhydrous sodium sulfate, and concentrated to give 120 mg of crude product which was suspended in water, filtered, and washed with small amount of ethyl acetate to afford another 67 mg of 3-[1-(3,5-dimethyl-1H-pyrrol-2-yl)-meth-(Z)-ylidene]-2-oxo-2,3-dihydro-indole-1-carboxylic acid 2,3-dihydroxy-propyl ester. The combined yield is 83%. $^1$H NMR (400 MHz, CDCl$_3$) δ 12.51 (s, 1H, NH-1'), 7.90–7.92 (m, 1H), 7.45–7.48 (m, 1H), 7.37 (s, 1H, H-vinyl), 7.18–7.24 (m, 2H), 6.04 (d, J=1.96 Hz, 1H, H-4'), 4.68 (dd, J=3.13, 11.24 Hz, 1H, OCH$_2$CH(OH)CH$_2$OH), 4.45 (dd, J=4.89, 11.24 Hz, 1H, OCH$_2$CH(OH)CH$_2$OH), 4.09 (m, br, 1H, OCH$_2$CH(OH)CH$_2$OH), 3.86–3.99 (m, 2H, OCH$_2$CH(OH)CH$_2$OH), 3.60 (d, J=6.65 Hz, 1H, OCH$_2$CH(OH)CH$_2$OH), 3.45 (dd, J=5.52, 7.82 Hz, 1H, OCH$_2$CH(OH)CH$_2$OH), 2.41 (s, 3H, CH$_3$), and 2.32 (s, 3H, CH$_3$). MS m/z (relative intensity, %) 357 (100, [M+1]$^+$.).

Example 10

Synthesis of 3-[1-(3,5-dimethyl-1H-pyrrol-2-yl)-meth-(Z)-ylidene]-2-oxo-2,3-dihydro-indole-1-carboxylic acid 2-hydroxy-3-phosphonooxy-propyl ester Step 1

To a solution of solketal (1.06 g, 8.0 mmol) in 4.0 mL of CH$_2$Cl$_2$ and 1.0 mL of pyridine was added dimethyl chlorophosphate (1.34 g, 9.2 mmol). The reaction mixture was stirred for 12 h at room temperature and concentrated. The residue was purified by silica gel chromatography eluting with CH$_2$Cl$_2$-Methanol (20:1) to yield 1.5 gram (81%) of phosphoric acid 2,2-dimethyl-[1,3]dioxolan-4-yl ester dimethyl ester as an oil. $^1$H NMR (400 MHz, DMSO-d$_6$) δ 4.21–4.27 (m, 1H), 3.96–4.02 (m, 2H), 3.87–3.93 (m, 1H), 3.60–3.70 (m, 1H), 3.66 (d, J=10.8 Hz, 6H, C(CH$_3$)$_2$), 1.32 (s, 3H, OCH$_3$), and 1.25 (s, 3H, OCH$_3$). $^{31}$P NMR (162 MHz, DMSO-d$_6$) δ 2.26.

Step 2

To a solution of phosphoric acid 2,2-dimethyl-[1,3]-dioxolan-4-yl ester dimethyl ester (600 mg, 2.5 mmol) in 3.0 mL of dichloromethane and 0.5 mL of methanol was added 3.5 mL of 1 M solution of hydrogen chloride in dimethylether dropwise. The reaction mixture was stirred for 5 h at room temperature and concentrated. The residue was purified by silica gel chromatography eluting with CH$_2$Cl$_2$-Methanol (9:1) to yield 321 mg (69%) of phosphoric acid 1,2-dihydroxy-ethyl ester dimethyl ester as an oil. $^1$H NMR (400 MHz, DMSO-d$_6$) δ 4.99 (d, J=5.2 Hz, 1H, OH), 4.66 (t, J=5.6 Hz, 1H, OH), 3.93–3.98 (m, 1H), 3.78–3.83 (m, 1H), 3.65 (d, J=11.2 Hz, 6H), and 3.27–3.37 (m, 3H). $^{31}$P NMR (162 MHz, d$_6$-DMSO) δ 2.5.

Step 3

To a solution of phosphoric acid 1,2-dihydroxy-ethyl ester dimethyl ester (151 mg, 0.75 mmol) and 3-[1-(3,5-dimethyl-1H-pyrrol-2-yl)-meth-(Z)-ylidene]-2-oxo-2,3-dihydro-indole-1-carbonyl chloride (98 mg, 0.33 mmol) in 5.0 mL of dichloromethane was added 0.1 mL of pyridine. The reaction mixture was stirred for 5 h at room temperature and concentrated. The residue was purified by silica gel chromatography eluting with dichloromethan-methanol (50:1) to yield 275 mg (79%) of 3-[1-(3,5-dimethyl-1H-pyrrol-2-yl)-meth-(Z)-ylidene]-2-oxo-2,3-dihydro-indole-1-carboxylic acid 3-(dimethoxyphosphonooxy)-2-hydroxy-propyl ester as a red solid. $^1$HNMR (400 MHz, DMSO-d$_6$) δ 12.61 (s, 1H, NH-1'), 7.84–7.86 (m, 1H, H-4), 7.77–7.79 (m, 1H, H-7), 7.64 (s, 1H, H-vinyl), 7.16–7.23 (m, 2H, H-5, 6), 6.11 (s, 1H, H-4'), 5.56 (d, J=5.2 Hz, 1H), 4.37 (t, J=4.4 Hz, 2H), 4.09–4.14 (m, 1H), 4.04–4.09 (m, 2H), 3.67 (d, J=11.2 Hz, 6H, 2×OCH$_3$), 2.37 (s, 3H, CH$_3$), and 2.33 (s, 3H, CH$_3$) $^{31}$P NMR (162 MHz, d$_6$-DMSO) δ 2.40; LCMS +cAPCI m/z 465 (M+H).

Step 4

To a solution of 3-[1-(3,5-dimethyl-1H-pyrrol-2-yl)-meth-(Z)-ylidene]-2-oxo-2,3-dihydro-indole-1-carboxylic acid 3-(dimethoxy-phosphonooxy)-2-hydroxy-propyl ester (60 mg, 0.4 mmol) in 1.5 mL of acetonitrile and 1.5 mL of dichloromethane was added 52 µl (0.40 mmoL) of TMSBr dropwise. The reaction mixture was stirred for 6 h at room temperature and concentrated. The residue was quenched with 0.05 mL of water followed by 1.5 mL of EtOAc. The resultant mixture was centrifuged and the solvent was decanted. The precipitate was washed twice with ethyl acetate and dried to afford 120 mg (62%) of 3-[1-(3,5-dimethyl-1H-pyrrol-2-yl)-meth-(Z)-ylidene]-2-oxo- 2,3-dihydro-indole-1-carboxylic acid 2-hydroxy-3-phosphonooxy-propyl ester as an orange solid. $^1$H NMR (400 MHz, DMSO-d$_6$) δ 12.61 (s, 1H, NH-1'), 7.84 (dd, J=2.4, 8.0 Hz, 1H, H-4), 7.79 (dd, J=2.2, 6.8 Hz, 1H, H-7), 7.64 (s, 1H, H-vinyl), 7.16–7.21 (m, 2H, H-5, 6), 6.11 (s, br, 1H, H-4'), 4.40 (dd, J=4.0, 10.8 Hz, 1H), 4.32 (dd, J=5.8, 11.2 Hz, 1H), 4.00–4.05 (m, 1H) 3.90–3.93 (m, 2H), 2.37 (s, 3H, CH$_3$), 2.33 (s, 3H, CH$_3$). $^{31}$P NMR (162 MHz, d$_6$-DMSO) δ 0.16.

Example 11

Synthesis of 3-[1-(3,5-dimethyl-1H-pyrrol-2-yl)-meth-(Z)-ylidene]-2-oxo-2,3-dihydro-indole-1-carboxylic acid 2-diethylamino-ethyl ester 3-[1-(3,5-dimethyl-1H-pyrrol-2-yl)-meth-(Z)-ylidene]-2-oxo-2,3-dihydro-indole-1-carboxylic acid 2-diethylamino-ethyl ester was prepared using the same procedure described in Example 9 above, but substituting glycerol with 2-diethylamino-ethanol to give the desired product in 31% yield. $^1$H NMR (400 MHz, CDCl$_3$) δ 12.68 (s, br, 1H, NH-1'), 7.90–7.92 (m, 1H), 7.49–7.51 (m, 1H), 7.40 (s, 1H, H-vinyl), 7.16–7.22 (m, 2H), 6.03 (d, J=1.95 Hz, 1H, H-4'), 4.52 (t, J=6.64 Hz, 2H, COOCH$_2$CH$_2$N(CH$_2$CH$_3$)$_2$), 2.91 (t, J=6.64 Hz, 2H, COOCH$_2$CH$_2$N(CH$_2$CH$_3$)$_2$), 2.66 (q, J=7.03 Hz, 4H, COOCH$_2$CH$_2$N(CH$_2$CH$_3$)$_2$), 2.38 (s, 3H, CH$_3$), 2.34 (s, 3H, CH$_3$), and 1.08 (t, J=7.03 Hz, 6H, COOCH$_2$CH$_2$N(CH$_2$CH$_3$)$_2$).

Example 12

Synthesis of 3-[1-(3,5-dimethyl-1H-pyrrol-2-yl)-meth-(Z)-ylidene]-2-oxo-2,3-dihydro-indole-1-carboxylic acid carboxymethyl ester A reaction mixture of 3-[1-(3,5-dimethyl-1h-pyrrol-2-yl)-meth-(z)-ylidene]-1-(imidazol-1-ylcarbonyl)-1,3-dihydro-indole-2-one (166 mg, 0.5 mmol), glycolic acid (163 mg, 1.5 mmol, 70% w/w in water) and (68 mg, 0.6 mmol) of TFA in 3 mL of THF was stirred at room temperature for 4 h and diluted with ethyl acetate and water. The organic layer was washed with brine, dried over anhydrous magnesium sulfate, and concentrated. The precipitate was filtered, washed with small amount of ethyl acetate, and dried in a vacuum oven overnight to afford 42 mg (25%) of 3-[1-(3,5-dimethyl-1H-pyrrol-2-yl)-meth-(Z)-ylidene]-2-oxo-2,3-dihydro-indole-1-carboxylic acid carboxymethyl ester. $^1$H NMR (400 MHz, DMSO-d6 and CDCl$_3$) δ 12.63 (s, 1H, NH-1'), 7.92–7.94 (m, 1H), 7.52–7.55 (m, 1H), 7.44 (s, 1H, H-vinyl), 7.20–7.22 (m, 2H), 6.06 (s, br, 1H, H-4'), 4.94 (s, 2H, CH2), 2.39 (s, 3H, CH$_3$), and 2.36 (s, 3H, CH$_3$).

Example 13

Synthesis of 3-[1-(3,5-dimethyl-1H-pyrrol-2-yl)-meth-(Z)-ylidene]-2-oxo-2,3-dihydro-indole-1-carboxylic acid 2-(2-oxo-pyrrolidin-1-yl)-ethyl ester 3-[1-(3,5-Dimethyl-1H-pyrrol-2-yl)-meth-(Z)-ylidene]-2-oxo-2,3-dihydro-indole-1-carboxylic acid 2-(2-oxo-pyrrolidin-1-yl)-ethyl ester was prepared by the procedure described in Example 12 above, but substituting glycolic acid with 2-(2-oxo-pyrrolidin-1-yl)ethanol to give a yield of 50%. $^1$H NMR (400 MHz, CDCl$_3$) δ 12.70 (s, 1H, NH-1'), 7.83–7.85 (m, 1H), 7.49–7.51 (m, 1H), 7.40 (s, 1H, H-vinyl), 7.17–7.24 (m, 2H), 6.04 (d, J=1.95 Hz, 1H, H-4'), 4.61 (t, J=5.45 Hz, 2H, CH$_2$), 3.77 (t, J=5.45 Hz, 2H, CH$_2$), 3.61 (t, J=7.03 Hz, 2H, CH$_2$), 2.42 (t, J=7.81 Hz, 2H, CH$_2$), 2.39 (s, 3H, CH$_3$), 2.35 (s, 3H, CH$_3$), and 2.02–2.10 (m, 2H, CH$_2$). MS m/z (relative intensity, %) 394 (100, [M+1]$^+$,.).

Example 14

Synthesis of 3-[1-(3,5-dimethyl-1H-pyrrol-2-yl)-meth-(Z)-ylidene]-2-oxo-2,3-dihydro-indole-1-carboxylic acid 2-(2,5-dioxo-pyrrolidin-1-yl)-ethyl ester 3-[1-(3,5-Dimethyl-1H-pyrrol-2-yl)-meth-(Z)-ylidene]-2-oxo-2,3-dihydro-indole-1-carboxylic acid 2-(2,5-dioxo-pyrrolidin-1-yl)-ethyl ester was prepared as described in Example 12 above, but substituting glycolic acid with 2-(2,5-dioxo-pyrrolidin-1-yl)-ethanol to provide a yield of 61%. $^1$H NMR (400 MHz, CDCl$_3$) δ 12.64 (s, 1H, NH-1'), 7.80–7.82 (m, 1H), 7.47–7.50 (m, 1H), 7.39 (s, 1H, H-vinyl), 7.16–7.23 (m, 2H), 6.03 (d, J=2.35 Hz, 1H, H-4'), 4.65 (t, J=5.27 Hz, 2H, CH$_2$), 4.02 (t, J=5.27 Hz, 2H, CH$_2$), 2.75 (s, 4H, 2×CH$_2$), 2.39, (s, 3H, CH$_3$), and 2.34 (s, 3H, CH$_3$).

Example 15

Synthesis of 3-[1-(3,5-dimethyl-1H-pyrrol-2-yl)-meth-(Z)-ylidene]-2-oxo-2,3-dihydro-indole-1-carboxylic acid 2-carboxy-2-hydroxy-ethyl ester A reaction mixture of 3-[1-(3,5-dimethyl-1h-pyrrol-2-yl)-meth-(z)-ylidene]-1-(imidazol-1-ylcarbonyl)-1,3-dihydro-indole-2-one (166 mg, 0.5 mmol), L-glyceric acid (432 mg, 1.5 mmol), and TFA (399 mg, 3.5 mmol) in 3 mL of THF was stirred at room temperature for 4 h and concentrated. The residue was purified by silica gel chromatography eluting with ethyl acetate-hexane (1:4) followed by 1% of acetic acid in ethylacetate-hexane (1:1) to afford 15 mg (8%) of 3-[1-(3,5-dimethyl-1H-pyrrol-2-yl)-meth-(Z)-ylidene]-2-oxo-2,3-dihydro-indole-1-carboxylic acid 2-carboxy-2-hydroxy-ethyl ester as a red solid. MS m/z (relative intensity, %) 371 (100, [M+1]$^+$.).

Example 16

Synthesis of 3-[1-(3,5-dimethyl-1H-pyrrol-2-yl)-meth-(Z)-ylidene]-2-oxo-2,3-dihydro-indole-1-carboxylic acid (3R,4S,5R)-3,4,5,6-tetrahydroxy-tetrahydro-pyran-2-ylmethyl ester Step 1

To a solution of 1,2,3,4-di-O-isopropylidene-D-galactopyranose (650 mg, 2.5 mmol) in 1.0 mL of pyridine and 2.0 mL of THF was added a suspension of 3-[1-(3,5-dimethyl-1H-pyrrol-2-yl)-meth-(Z)-ylidene]-2-oxo-2,3-dihydro-indole-1-carbonyl chloride (150 mg, 0.5 mmol) at 0° C. The reaction mixture was then gradually warmed to room temperature, stirred for 4 h, and concentrated. The residue was triturated with water and washed with ether to give 170 mg (65%) of 3-[1-(3,5-dimethyl-1H-pyrrol-2-yl)-meth-(Z)-ylidene]-2-oxo-2,3-dihydro-indole-1-carboxylic acid (3aR,5aS,8aS,8bR)-2,2,7,7-tetramethyl-tetrahydro-bis[1,3]dioxolo[4,5-b;4',5'-d]pyran-5-ylmethyl ester.

Step 2

3-[1-(3,5-Dimethyl-1H-pyrrol-2-yl)-meth-(Z)-ylidene]-2-oxo-2,3-dihydro-indole-1-carboxylic acid (3aR,5aS,8aS,8bR)-2,2,7,7-tetramethyl-tetrahydro-bis[1,3]dioxolo[4,5-b;4',5'-d]pyran-5-ylmethyl ester was dissolved in the mixture of 5.0 mL of 6 N HCl aq. and 20 mL of THF. The resultant mixture was stirred at room temperature for 3 h and 40 C for 1 h and concentrated. The residue was washed with ethyl acetate and THF and dried to give 133 mg (60%) of 3-[1-(3,5-dimethyl-1H-pyrrol-2-yl)-meth-(Z)-ylidene]-2-oxo-2,3-dihydro-indole-1-carboxylic acid (3R,4S,5R)-3,4,5,6-tetrahydroxy-tetrahydro-pyran-2-ylmethyl ester as a yellow solid.

$^1$H NMR (400 MHz, CDCl$_3$) δ 12.54 (s, br, 1H, NH-1'), 7.72–7.79 (m, 2H), 7.56 (s, 1H, H-vinyl), 7.20–7.27 (m, 2H), 6.14 (d, J=1.56 Hz, 1H, H-4'), 5.07 (d, J=3.52 Hz, 1H), 4.47–4.53 (m, 2H), 4.39 (d, J=7.43 Hz, 1H), 4.31 (t, J=5.86 Hz, 1H), 3.90–3.92 (m, 2H), 3.84 (d, J=3.12 Hz, 1H), 3.71 (dd, J=3.12, 10.16 Hz, CH), 3.65 (dd, J=3.52, 10.16 Hz, 1H), 3.45 (dd, J=3.52, 9.77 Hz, 1H), 3.36 (dd, J=7.63, 9.58 Hz, 1H), 2.39 (s, 3H, CH$_3$), and 2.34 (s, 3H, CH$_3$).

Example 17

Synthesis of 3-[1-(3,5-dimethyl-1H-pyrrol-2-yl)-meth-(Z)-ylidene]-2-oxo-2,3-dihydro-indole-1-carboxylic acid 2-morpholin-4-yl-ethyl ester To the reaction suspension of 3-[1-(3,5-dimethyl-1h-pyrrol-2-yl)-meth-(z)-ylidene]-1-(imidazol-1-ylcarboxnyl)-1,3-dihydro-indole-2-one (166 mg, 0.5 mmol) in 4 mL of THF-CH$_2$Cl$_2$ (2 mL:2 mL) was added TFA (0.13 mL, 1.5 mmol) and 4-(2-hydroxyethyl)morpholine at room temperature. The reaction mixture was then stirred at room temperature for 19 hours, concentrated, and purified on a silica gel column eluting with ethyl acetate-hexane-triethylamine (3:2:0.1) to give 3-[1-(3,5-dimethyl-1H-pyrrol-2-yl)-meth-(Z)-ylidene]-2-oxo-2,3-dihydro-indole-1-carboxylic acid 2-morpholin-4-yl-ethyl ester (26 mg, 13%)as an orange solid. $^1$HNMR (400 MHz, DMSO-d6) δ 12.63 (s, br, 1H, N-1'), 7.86–7.88 (m, 2H), 7.65 (s, 1H, H-vinyl), 7.19–7.24 (m, 2H), 6.13 (s, 1H, H-4'), 3.59 (t, J=4.49 Hz, 4H, CH$_{2\times2}$), 2.72 (t, J=5.47 Hz, 2H, CH$_2$), 2.38 (s, 3H, CH$_3$), 2.35 (s, 3H, CH$_3$), and 1.25 (m, 1H).

Example 18

Synthesis of 3-[1-(3,5-dimethyl-1H-pyrrol-2-yl)-meth-(Z)-ylidene]-2-oxo-2,3-dihydro-indole-1-carboxylic acid 2-pyrrolidin-1-yl-ethyl ester A reaction mixture containing 3-[1-(3,5-dimethyl-1h-pyrrol-2-yl)-meth-(z)-ylidene]-1-(imidazol-1-ylcarbonyl)-1,3-dihydro-indole-2-one (166 mg, 0.5 mmol), 2-pyrrolidin-1-yl-ethanol (115 mg, 1.0 mmol), and TFA (0.13 mL, 1.5 mmol) in 2 mL of THF, and 2 mL of dichloromethane gave 3-[1-(3,5-dimethyl-1H-pyrrol-2-yl)-meth-(Z)-ylidene]-2-oxo-2,3-dihydro-indole-1-carboxylic acid 2-pyrrolidin-1-yl-ethyl ester (28 mg, 15%) as a yellow solid. $^1$HNMR (400 MHz, DMSO-d6) δ 12.56 (s, br, 1H, N-1'), 7.80–7.86 (m, 2H), 7.64 (s, 1H, H-vinyl), 7.16–7.20 (m, 2H), 6.10 (s, 1H, H-4'), 4.46 (t, J=5.47 Hz, 2H, CH$_2$), 2.83 (m, br, 2H, CH$_2$), 2.56 (m, br, 4H, CH$_{2\times2}$), 2.36 (s, 3H, CH$_3$), 2.33 (s, 3H, CH$_3$), and 1.69 (m, br, 4H, CH$_{2\times2}$).

Example 19

Synthesis of 1-{3-[1-(3,5-dimethyl-1H-pyrrol-2-yl)-meth-(Z)-ylidene]-2-oxo-2,3-dihydro-indole-1-carbonyl}-pyrrolidine-2-carboxylic acid A reaction mixture of 3-[1-(3,5-dimethyl-1h-pyrrol-2-yl)-meth-(z)-ylidene]-1-(imidazol-1-ylcarboxnyl)-1,3-dihydro-indole-2-one (169 mg, 0.5 mmol), L-proline (69 mg, 0.6 mmol) in 2 mL of THF and 2 mL of dichloromethane was stirred at room temperature for two days and concentrated. The product was then purified on a silica gel column eluting with ethyl acetate-hexane-acetic acid (3:2:0.1) to give 1-{3-[1-(3,5-dimethyl-1H-pyrrol-2-yl)-meth-(Z)-ylidene]-2-oxo-2,3-dihydro-indole-1-carbonyl}-pyrrolidine-2-carboxylic acid (144 mg, 77%) as a yellow solid. $^1$HNMR (400 MHz, CDCl$_3$) δ 12.72 (s, 1H, H-1'), 7.47 (d, J=7.43 Hz, 1H), 7.26 (s, 1H, H-vinyl), 7.22 (d, J=7.43 Hz, 1H), 7.16 (t, J=7.43 Hz, 1H), 7.10 (t, J=7.43 Hz, 1H), 6.00 (s, 1H, H-4'), 4.78 (s, br, 1H), 3.77 (m, br, 2H), 2.37 (s, 3H, CH$_3$), 2.33 (s, 3H, CH$_3$), 2.28–2.37 (m, 2H), and 2.02–2.08 (m, 2H).

Example 20

Synthesis of 3-[1-(3,5-dimethyl-1H-pyrrol-2-yl)-meth-(Z)-ylidene]-2-oxo-2,3-dihydro-indole-1-carboxylic acid (2-hydroxy-3-morpholin-4-yl-propyl)-amide A reaction mixture of 3-[1-(3,5-dimethyl-1h-pyrrol-2-yl)-meth-(z)-ylidene]-1-(imidazol-1-ylcarboxnyl)-1,3-dihydro-indole-2-one (166 mg, 0.5 mmol) and 1-amino-3-morpholin-4-yl-propan-2-ol (96 mg, 0.6 mmol) in 2 mL of DMF was stirred at room temperature for 2 days and filtered. The solid was washed with ethyl acetate and hexane and dried in a vacuum oven overnight to give 3-[1-(3,5-dimethyl-1H-pyrrol-2-yl)-meth-(Z)-ylidene]-2-oxo-2,3-dihydro-indole-1-carboxylic acid (2-hydroxy-3-morpholin-4-yl-propyl)-amide (44 mg, 20%) as a yellow solid. $^1$HNMR (400 MHz, CDCl3) δ 12.54 (s, 1H, NH-1'), 9.11 (t, J=6.06 Hz, 1H, NCONH-1), 8.11–8.13 (m, 1H), 7.87–7.90 (m, 1H), 7.74 (s, 1H, H-vinyl), 7.16–7.23 (m, 2H, H-5,6), 6.17 (d, J=1.96 Hz, 1H, H-4'), 5.96 (s, br, 1H, OH, exchangeable with addition of D$_2$O), 4.26 (m, br, 1H), 3.90–3.97 (m, 2H), 3.75–3.84 (m, 2H), 2.27–3.5 (m, 5H), 3.11–3.17 (m, 3H), 2.39 (s, 3H, CH$_3$), and 2.37 (s, 3H, CH$_3$).

Example 21

Synthesis of 3-[1-(3,5-dimethyl-1H-pyrrol-2-yl)-meth-(Z)-ylidene]-2-oxo-2,3-dihydro-indole-1-carboxylic acid 2-hydroxy-3-pyrrolidin-1-yl-propyl ester To a reaction mixture of 3-[1-(3,5-dimethyl-1H-pyrrol-2-yl)-meth-(Z)-ylidene]-2-oxo-2,3-dihydro-indole-1-carbonyl chloride (150 mg, 0.5 mmol) and 3-pyrrolidin-1-yl-propane-1,2-diol (88 mg, 0.6 mmol) in 3.0 mL of THF was added 80 μl of pyridine dropwise at room temperature. Upon addition, the reaction mixture was stirred at room temperature for 20 min., and filtered. The orange solid was then washed with ethyl acetate and hexane sequentially and dried in a vacuum oven overnight to give 3-[1-(3,5-dimethyl-1H-pyrrol-2-yl)-meth-(Z)-ylidene]-2-oxo-2,3-dihydro-indole-1-carboxylic acid 2-hydroxy-3-pyrrolidin-1-yl-propyl ester as an orange solid. $^1$HNMR (400 MHz, CDCl$_3$ and 2 drops of DMSO-d6) δ 12.63 (s, br, 1H, NH-1'), 11.77 (s, br, 1H, OH), 7.86–7.88 (m, 1H), 7.51–7.53 (m, 1H), 7.42 (s, 1H, H-vinyl), 7.18–7.25 (m, 2H), 6.06 (d, J=2.3 Hz, 1H, H-4'), 4.65–4.73 (m, 2H), 4.44–4.56 (m, 2H), 3.91–3.93 (m, 1H), 3.33–3.52 (m, 2H), 2.88–3.15 (m, 2H), 2.40 (s, 3H, CH$_3$), 2.36 (s, 3H, CH$_3$), and 2.01–2.32 (m, 4H).

Example 22

Synthesis of 3-[1-(3,5-dimethyl-1H-pyrrol-2-yl)-meth-(Z)-ylidene]-2-oxo-2,3-dihydro-indole-1-carboxylic acid 3-hydroxy-propyl ester To a reaction mixture of 1,3-propanediol (380 mg, 5.0 mmol) in 1.5 mL of pyridine and 4.0 mL of THF was added a suspension of of 3-[1-(3,5-dimethyl-1H-pyrrol-2-yl)-meth-(Z)-ylidene]-2-oxo-2,3-dihydro-indole-1-carbonyl chloride (301 mg, 1.0 mmol) in 2.0 mL of THF dropwise at 0° C. The reaction mixture was then warmed to room temperature and stirred overnight and concentrated. The residue was suspended in ethyl acetate and filtered. The solid was washed with ethyl acetate, water, 0.1 N Hclaq, and ether to give 309 mg (91%) of 3-[1-(3,5-dimethyl-1H-pyrrol-2-yl)-meth-(Z)-ylidene]-2-oxo-2,3-dihydro-indole-1-carboxylic acid 3-(dimethoxy-phosphonooxy)-propyl ester as a orange solid. $^1$H NMR (400 MHz, CDCl$_3$) δ 12.59 (s, br, 1H, NH-1'), 7.94–7.96 (m, 1H, H-4), 7.49–7.51 (m, 1H, H-7), 7.41 (s, 1H, H-vinyl), 7.18–7.26 (m, 2H, H-5, 6), 6.03 (s, br, 1H, H-4'), 4.63 (t, J=5.47 Hz, 2H, NCOOCH$_2$CH$_2$CH$_2$OH-1), 3.91 (dt, J=5.61, 10.94 Hz, 2H, NCOOCH$_2$CH$_2$CH$_2$OH-1), 3.63 (t, J=5.61 Hz, 1H, OH), 2.40 (s, 3H, CH$_3$), 2.34 (s, 3H, CH$_3$), and 2.09–2.30 (m, 2H, NCOOCH$_2$CH$_2$CH$_2$OH-1).

Example 23

Synthesis of 1-{3-[1-(3,5-dimethyl-1H-pyrrol-2-yl)-meth-(Z)-ylidene]-2-oxo-2,3-dihydro-indole-1-carbonyl}-5-fluoro-1H-pyrimidine-2,4-dione To a reaction mixture of 3-[1-(3,5-dimethyl-1H-pyrrol-2-yl)-meth-(Z)-ylidene]-2-oxo-2,3-dihydro-indole-1-carbonyl chloride (75 mg, 0.25 mmol), 5-fluorouracil (75 mg, 0.58 mmol), and 0.5 mL of pyridine in 2.0 mL of THF was stirred at room temperature for 1 h and filtered. The solid was then washed with THF, acetone, methanol, and ether to give 34 mg (36%) of 1-{3-[1-(3,5-dimethyl-1H-pyrrol-2-yl)-meth-(Z)-ylidene]-2-oxo-2,3-dihydro-indole-1-carbonyl}-5-fluoro-1H-pyrimidine-2,4-dione as a light yellow solid. $^1$HNMR (400 MHz, DMSO-d6) δ 12.22 (d, J=4.69 Hz, 1H, CONHCO), 12.19 (s, br, 1H, NH-1'), 8.33 (d, J=6.64 Hz, 1H, H-6"), 7.92–7.94 (m, 1H, H-4), 7.74–7.76 (m, 1H, H-7), 7.71 (s, 1H, H-vinyl), 7.26–7.29 (m, 2H, H-5, 6), 6.16 (s, br, 1H, H-4'), 2.47 (s, 3H, $CH_3$), and 2.35 (s, 3H, $CH_3$).

Example 24

Synthesis of 3-[1-(3,5-dimethyl-1H-pyrrol-2-yl)-meth-(Z)-ylidene]-2-oxo-2,3-dihydro-indole-1-carboxylic acid 2-hydroxy-3-morpholin-4-yl-propyl ester A reaction mixture of 3-[1-(3,5-dimethyl-1H-pyrrol-2-yl)-meth-(Z)-ylidene]-2-oxo-2,3-dihydro-indole-1-carbonyl chloride (150 mg, 0.5 mmol), 3-morpholin-4-yl-propane-1,2-diol, and pyridine in 3.0 mL of THF was stirred at room temperature for 15 min and filtered. The solid was then washed with ethyl acetate and ether to give 116 mg (55%) of 3-[1-(3,5-dimethyl-1H-pyrrol-2-yl)-meth-(Z)-ylidene]-2-oxo-2,3-dihydro-indole-1-carboxylic acid 2-hydroxy-3-morpholin-4-yl-propyl ester as an orange solid. $^1$HNMR (400 MHz, DMSO-d6) δ 12.06 (s, br, 1H, NH-1'), 10.47 (s, br, 1H, OH), 7.86–7.88 (m, 1H, H-4), 7.79–7.81 (m, 1H, H-7), 7.66 (s, 1H, H-vinyl), 7.19–7.23 (m, 2H, H-5, 6), 6.12 (d, J=2.34 Hz, 1H, H-4'), 4.35–4.45 (m, 3H), 3.75–3.98 (m, 4H), 3.26–3.51 (m, 7H), 2.37 (s, 3H, $CH_3$), and 2.34 (s, 3H, $CH_3$).

Example 25

Synthesis of 3-[1-(3,5-dimethyl-1H-pyrrol-2-yl)-meth-(Z)-ylidene]-2-oxo-2,3-dihydro-indole-1-carboxylic acid 4-((E)-2-carboxy-vinyl)-phenyl ester A reaction mixture of of 3-[1-(3,5-dimethyl-1H-pyrrol-2-yl)-meth-(Z)-ylidene]-1-(imidazol-1-ylcarbonyl)-1,3-dihydro-indol-2-one (165 mg, 0.5 mmol), cinnamic acid (85 mg, 0.5 mmol), and 2 drops of triethylamine in 3 mL of THF was stirred at 60° C. for 5 h and room temperature overnight and filtered. The solid was then washed with ethyl acetate and 1 N aqueous hydrogen chloride solution. The filtrate was concentrated and the residue was partitioned between ethyl acetate and water-acetic acid. The organic layer was washed with diluted sodium hydroxide solution, dried over magnesium sulfate, and concentrated. The resultant residue was suspended in warm ethyl acetate and filtered. The combined solid was then dried in a vacuum oven overnight to afford 35 mg (16%) of 3-[1-(3,5-dimethyl-1H-pyrrol-2-yl)-meth-(Z)-ylidene]-2-oxo-2,3-dihydro-indole-1-carboxylic acid 4-((E)-2-carboxy-vinyl)-phenyl ester. $^1$H NMR (400 MHz, DMSO-d6) δ 12.55 (s, 1H, NH-1'), 12.41 (s, br, 1H, COOH), 7.91–7.94 (m, 1H), 7.82–7.85 (m, 3H), 7.71 (s, 1H, H-vinyl), 7.65 (d, J=6.02 Hz, 1H), 7.44 (d, J=8.99 Hz, 1H), 7.24–7.26 (m, 2H), 6.57 (d, J=6.02 Hz, 1H), 6.15 (d, J=2.35 Hz, 1H, H-4'), 2.39 (s, 3H, $CH_3$), and 2.37 (s, 3H, $CH_3$).

Example 26

Synthesis of 3-[1-(3,5-dimethyl-1H-pyrrol-2-yl)-meth-(Z)-ylidene]-2-oxo-2,3-dihydro-indole-1-carboxylic acid 4-carboxy-phenyl ester A reaction mixture of 3-[1-(3,5-dimethyl-1H-pyrrol-2-yl)-meth-(Z)-ylidene]-1-(imidazol-1-ylcarbonyl)-1,3-dihydro-indol-2-one (332 mg, 1.0 mmol), 4-hydroxybenzoic acid (138 mg, 1.0 mmol), and 2 drops of triethylamine in 3.0 mL of THF was stirred at room temperature overnight and concentrated. The residue was then purified on a silica gel column eluting with ethyl acetate-hexane (1:3) and 0.5% of acetic acid in ethyl acetate-dichloromethane (2:1) to afford 150 mg (37%) of 3-[1-(3,5-dimethyl-1H-pyrrol-2-yl)-meth-(Z)-ylidene]-2-oxo-2,3-dihydro-indole-1-carboxylic acid 4-carboxy-phenyl ester. $^1$H NMR (400 MHz, DMSO-d6) δ 12.65 (s, vbr, 1H, COOH), 12.60 (s, br, 1H, NH-1'), 8.12 (d, J=7.39 Hz, 2H), 7.86–7.88 (m, 1H), 7.64 (s, vbr, 1H), 7.51 (s, 1H, H-vinyl), 7.43 (d, J=7.39 Hz, 2H), 7.21–7.23 (m, 2H), 6.09 (s, br, 1H, H-4'), 2.40 (s, 3H, $CH_3$), and 2.38 (s, 3H, $CH_3$).

Example 27

Synthesis of 3-[1-(3,5-dimethyl-1H-pyrrol-2-yl)-meth-(Z)-ylidene]-2-oxo-2,3-dihydro-indole-1-carboxylic acid 2-phosphonooxy-ethyl ester To the suspension of 3-[1-(3,5-dimethyl-1H-pyrrol-2-yl)-meth-(Z)-ylidene]-2-oxo-2,3-dihydro-indole-1-carboxylic acid 2-(dimethoxy-phosphonooxy)-ethyl ester (180 mg, 0.4 mmol) in 12 mL of acetonitrile was added bromotrimethylsilane (120 mL, 0.91 mmol) and N,O-bis-(trimethylsily) acetamide (225 mL, 0.91 mmol) sequentially. The reaction mixture was then stirred at room temperature for 42 h and concentrated. The residue was then washed with ethyl acetate, water, and 0.1 N HClaq and dried in a vacuum oven to yield 75 mg (37%) of 3-[1-(3,5-dimethyl-1H-pyrrol-2-yl)-meth-(Z)-ylidene]-2-oxo-2,3-dihydro-indole-1-carboxylic acid 2-phosphonooxy-ethyl ester as a red solid. $^1$H NMR (400 MHz, $CDCl_3$) δ 12.40 (s, br, 1H, NH-1'), 7.84–7.86 (m, 1H, H-4), 7.76–7.79 (m, 1H, H-7), 7.63 (s, 1H, H-vinyl), 7.19–7.22 (m, 2H, H-5, 6), 6.11 (d, J=1.95 Hz, 1H, H-4'), 4.52–4.56 (m, 2H, NCOOC$H_2$C$H_2$OPO(O$CH_3$)$_2$-1), 4.15–4.19 (m, 2H, NCOOC$\underline{H}_2$CH$_2$OPO(O$CH_3$)$_2$-1), 2.37 (s, 3H, $CH_3$), and 2.33 (s, 3H, $CH_3$).

Example 28

Synthesis of 3-[1-(3,5-dimethyl-1H-pyrrol-2-yl)-meth-(Z)-ylidene]-2-oxo-2,3-dihydro-indole-1-carboxylic acid 3-(dimethoxy-phosphonooxy)-propyl ester 3-[1-(3,5-Dimethyl-1H-pyrrol-2-yl)-meth-(Z)-ylidene]-2-oxo-2,3-dihydro-indole-1-carboxylic acid 3-(dimethoxy-phosphonooxy)-propyl ester was prepared using the same protocol for synthesizing 3-[1-(3,5-dimethyl-1H-pyrrol-2-yl)-meth-(Z)-ylidene]-2-oxo-2,3-dihydro-indole-1-carboxylic acid 2-(dimethoxy-phosphonooxy)-ethyl ester by replacing 3-[1-(3,5-dimethyl-1H-pyrrol-2-yl)-meth-(Z)-ylidene]-

2-oxo-2,3-dihydro-indole-1-carboxylic acid 2-hydroxyethyl ester with 3-[1-(3,5-dimethyl-1H-pyrrol-2-yl)-meth-(Z)-ylidene]-2-oxo-2,3-dihydro-indole-1-carboxylic acid 3-hydroxy-propyl ester with a yield of (31%). $^1$H NMR (400 MHz, $CDCl_3$) δ 12.63 (s, br, 1H, NH-1'), 7.82–7.84 (m, 1H, H-4), 7.48–7.52 (m, 1H, H-7), 7.41 (s, 1H, H-vinyl), 7.17–7.24 (m, 2H, H-5, 6), 6.04 (s, br, 1H, H-4'), 4.61 (t, J=6.25 Hz, 2H, NCOOC$\underline{H}_2$CH$_2$CH$_2$OPO(OCH$_3$)$_2$-1), 4.31 (q, J=6.38, 10.94 Hz, 2H, NCOOCH$_2$CH$_2$C$\underline{H}_2$OPO(OCH$_3$)$_2$-1), 3.80 (s, 3H, NCOOCH$_2$CH$_2$CH$_2$OPO(OC$\underline{H}_3$)$_2$-1), 3.77 (s, 3H, NCOOCH$_2$CH$_2$CH$_2$OPO(OC$\underline{H}_3$)$_2$-1), 2.40 (s, 3H, CH$_3$), 2.35 (s, 3H, CH$_3$), and 2.23–2.29 (m, 2H, NCOOCH$_2$C$\underline{H}_2$CH$_2$OPO(OCH$_3$)$_2$-1). $^{13}$P NMR (162 MHz, $CDCl_3$) δ 2.40.

Example 29

Synthesis of 3-[1-(3,5-dimethyl-1H-pyrrol-2-yl)-meth-(Z)-ylidene]-2-oxo-2,3-dihydro-indole-1-carboxylic acid 3-phosphonooxypropyl ester 3-[1-(3,5-Dimethyl-1H-pyrrol-2-yl)-meth-(Z)-ylidene]-2-oxo-2,3-dihydro-indole-1-carboxylic acid 3-phosphonooxypropyl ester was prepared using the same procedure for preparing 3-[1-(3,5-dimethyl-1H-pyrrol-2-yl)-meth-(Z)-ylidene]-2-oxo-2,3-dihydro-indole-1-carboxylic acid 2-phosphonooxyethyl ester but substituting 3-[1-(3,5-dimethyl-1H-pyrrol-2-yl)-meth-(Z)-ylidene]-2-oxo-2,3-dihydro-indole-1-carboxylic acid 2-(dimethoxy-phosphonooxy)-ethyl ester with 3-[1-(3,5-dimethyl-1H-pyrrol-2-yl)-meth-(Z)-ylidene]-2-oxo-2,3-dihydro-indole-1-carboxylic acid 3-(dimethoxy-phosphonooxy)propyl ester.

Example 30

Synthesis of 3-[1-(3,5-dimethyl-1H-pyrrol-2-yl)-meth-(Z)-ylidene]-2-oxo-2,3-dihydro-indole-1-carboxylic acid 2-hydroxy-3-sulfooxypropyl ester sodium salt To the solution of (3-[1-(3,5-dimethyl-1H-pyrrol-2-yl)-meth-(Z)-ylidene]-2-oxo-2,3-dihydro-indole-1-carboxylic acid 2,3-dihydroxy-propyl ester (102 mg, 0.29 mmol) in 1.6 mL of pyridine was added sulfur trioxide pyridine complex (114 mg, 0.71 mmol) at room temperature and the reaction mixture was stirred at room temperature for 2 h. The reaction was then quenched with 25 mL of water and extrated with 3 mL of dichloromethane. The organic layer was then dried and purified on ion-exchange resin to give 3-[1-(3,5-dimethyl-1H-pyrrol-2-yl)-meth-(Z)-ylidene]-2-oxo-2,3-dihydro-indole-1-carboxylic acid 2-hydroxy-3-sulfooxypropyl ester sodium salt (65 mg, 49%) as a red solid.

Following the procedures described above, prodrugs of following compounds of Formula (II) can be prepared.

General Procedures

Method A: Formylation of Pyrroles $POCl_3$ (1.1 equiv.) is added dropwise to dimethylformamide (3 equiv.) at −10° C. followed by addition of the appropriate pyrrole dissolved in dimethylformamide. After stirring for two hours, the reaction mixture is diluted with $H_2O$ and basified to pH 11 with 10 N KOH. The precipitate which forms is collected by filtration, washed with $H_2O$ and dried in a vacuum oven to give the desired aldehyde.

Method B: Saponification of Pyrrolecarboxylic Acid Esters

A mixture of a pyrrolecarboxylic acid ester and KOH (2–4 equiv.) in EtOH is refluxed until reaction completion is indicated by thin layer chromatography (TLC). The cooled reaction mixture is acidified to pH 3 with 1 N HCl. The precipitate which forms is collected by filtration, washed with $H_2O$ and dried in a vacuum oven to give the desired pyrrolecarboxylic acid.

Method C: Amidation

To a stirred solution of a pyrrolecarboxylic acid dissolved in dimethylformamide(0.3M) is added 1-ethyl-3-(3-dimethylamino-propyl)carbodiimide (1.2 equiv.), 1-hydroxybenzotriazole (1.2 equiv.), and triethylamine (2 equiv.). The appropriate amine is added (1 equiv.) and the reaction stirred until completion is indicated by TLC. Ethyl acetate is then added to the reaction mixture and the solution washed with saturated $NaHCO_3$ and brine (with extra salt), dried over anhydrous $MgSO_4$ and concentrated to afford the desired amide.

Method D: Condensation of Aldehydes and Oxindoles Containing Carboxylic Acid Substituents A mixture of the oxindole (1 equivalent), 1 equivalent of the aldehyde and 1–3 equivalents of piperidine (or pyrrolidine) in ethanol (0.4 M) is stirred at 90–100° C. until reaction completion is indicated by TLC. The mixture is then concentrated and the residue acidified with 2N HCl. The precipitate that forms is washed with $H_2O$ and EtOH and then dried in a vacuum oven to give the product.

Method E: Condensation of Aldehydes and Oxindoles Not Containing Carboxylic Acid Substituents A mixture of the oxindole (1 equivalent), 1 equivalent of the aldehyde and 1–3 equivalents of piperidine (or pyrrolidine) in ethanol (0.4 M) is stirred at 90–100° C. until reaction completion is indicated by TLC. The mixture is cooled to room temperature and the solid which forms is collected by vacuum filtration, washed with ethanol and dried to give the product. If a precipitate does not form upon cooling of the reaction mixture, the mixture is concentrated and purified by column chromatography.

Synthesis of Oxindoles

5-Amino-2-oxindole

5-Nitro-2-oxindole (6.3 g) was hydrogenated in methanol over 10% palladium on carbon to give 3.0 g (60% yield) of the title compound as a white solid.

5-Bromo-2-oxindole

2-Oxindole (1.3 g) in 20 mL acetonitrile was cooled to −10° C. and 2.0 g N-bromosuccinimide was slowly added with stirring. The reaction was stirred for 1 hour at −10° C. and 2 hours at 0° C. The precipitate was collected, washed with water and dried to give 1.9 g (90% yield) of the title compound.

4-Methyl-2-oxindole

Diethyl oxalate (30 mL) in 20 mL of dry ether was added with stirring to 19 g of potassium ethoxide suspended in 50 mL of dry ether. The mixture was cooled in an ice bath and 20 mL of 3-nitro-o-xylene in 20 mL of dry ether was slowly added. The thick dark red mixture was heated to reflux for 0.5 hr, concentrated to a dark red solid, and treated with 10% sodium hydroxide until almost all of the solid dissolved. The dark red mixture was treated with 30% hydrogen peroxide until the red color changed to yellow. The mixture was treated alternately with 10% sodium hydroxide and 30% hydrogen peroxide until the dark red color was no longer present. The solid was filtered off and the filtrate acidified with 6N hydrochloric acid. The resulting precipitate was collected by vacuum filtration, washed with water, and dried under vacuum to give 9.8 g (45% yield) of 2-methyl-6-nitrophenylacetic acid as an off-white solid. The solid was hydrogenated in methanol over 10% palladium on carbon to give 9.04 g of the title compound as a white solid.

7-Bromo-5-chloro-2-oxindole

5-Chloro-2-oxindole (16.8 g) and 19.6 g of N-bromosuccinimide were suspended in 140 mL of acetonitrile and refluxed for 3 hours. Thin layer chromatography (silica, ethyl acetate) at 2 hours of reflux showed 5-chloro-2-oxindole or N-bromosuccinimide (Rf 0.8), product (Rf 0.85) and a second product (Rf 0.9) whose proportions did not change after another hour of reflux. The mixture was cooled to 10° C., the precipitate was collected by vacuum filtration, washed with 25 mL of ethanol and sucked dry for 20 minutes in the funnel to give 14.1 g of wet product (56% yield). The solid was suspended in 200 mL of denatured ethanol and slurry-washed by stirring and refluxing for 10 minutes. The mixture was cooled in an ice bath to 10° C. The solid product was collected by vacuum filtration, washed with 25 mL of ethanol and dried under vacuum at 40° C. to give 12.7 g (51% yield) of 7-bromo-5-chloro-2-oxindole.

5-Fluoro-2-oxindole

5-Fluoroisatin (8.2 g) was dissolved in 50 mL of hydrazine hydrate and refluxed for 1.0 hr. The reaction mixtures were then poured in ice water. The precipitate was then filtered, washed with water and dried in a vacuum oven to afford the title compound.

5-Nitro-2-oxindole

2-Oxindole (6.5 g) was dissolved in 25 mL concentrated sulfuric acid and the mixture maintained at −10 to −15° C. while 2.1 mL of fuming nitric acid was added dropwise. After the addition of the nitric acid the reaction mixture was stirred at 0° C. for 0.5 hr and poured into ice-water. The precipitate was collected by filtration, washed with water and crystallized from 50% acetic acid. The crystalline product was then filtered, washed with water and dried under vacuum to give 6.3 g (70%) of 5-nitro-2-oxindole.

5-Aminosulfonyl-2-oxindole

To a 100 mL flask charged with 27 mL of chlorosulfonic acid was added slowly 13.3 g of 2-oxindole. The reaction temperature was maintained below 30° C. during the addition. After the addition, the reaction mixture was stirred at room temperature for 1.5 hr, heated to 68° C. for 1 hr, cooled, and poured into water. The precipitate was washed with water and dried in a vacuum oven to give 11.0 g of 5-chlorosulfonyl-2-oxindole (50% yield) which was used without further purification.

5-Chlorosulfonyl-2-oxindole (2.1 g) was added to 10 mL of ammonium hydroxide in 10 mL of ethanol and stirred at room temperature overnight. The mixture was concentrated and the solid collected by vacuum filtration to give 0.4 g (20% yield) of the title compound as an off-white solid.

5-Isopropylaminosulfonyl-2-oxindole

To a 100 mL flask charged with 27 mL chlorosulfonic acid was slowly added 13.3 g 2-oxindole. The reaction temperature was maintained below 30° C. during the addition. The reaction mixture was stirred at room temperature for 1.5 hour, heated to 68° C. for 1 hour, cooled, and poured into water. The precipitate which formed was filtered, washed with water and dried in a vacuum oven to give 11.0 g (50%) of 5-chlorosulfonyl-2-oxindole which was used without further purification.

A suspension of 3 g 5-chlorosulfonyl-2-oxindole, 1.15 g isopropylamine and 1.2 mL of pyridine in 50 mL of dichloromethane was stirred at room temperature for 4 hours during which time a white solid formed. The solid was collected by vacuum filtration, slurry-washed with hot ethanol, cooled, collected by vacuum filtration and dried under vacuum at 40° C. overnight to give 1.5 g (45%) of 5-isopropylaminosulfonyl-2-oxindole.

$^1$HNMR (360 MHz, DMSO-d6) δ 10.69 (s, br, 1H, NH), 7.63 (dd, J=2 and 8 Hz, 1H), 7.59 (d, J=2 Hz, 1H), 7.32 (d, J=7 Hz, 1H, NH—SO$_2$—), 6.93 (d, J=8 Hz, 1H), 3.57 (s, 2H), 3.14–3.23 (m, 1H, CH—(CH$_3$)$_2$), 0.94 (d, J=7 Hz, 6H, 2×CH$_3$).

5-Phenylaminosulfonyl-2-oxindole

A suspension of 5-chlorosulfonyl-2-oxindole (1.62 g, 7 mmol), aniline (0.782 mL, 8.4 mmol) and pyridine (1 mL) in dichloromethane (20 ml) was stirred at room temperature for 4 hours. The reaction mixture was diluted with ethyl acetate (300 mL) and acidified with 1N hydrochloric acid (16 mL). The organic layer was washed with sodium bicarbonate and brine, dried and concentrated. The residue was washed with ethanol (3 mL) and then chromatographed on silica gel eluting with methanol/dichloromethane 1:9 to give of 5-phenylaminosulfonyl-2-oxindole.

$^1$HNMR (360 MHz, DMSO-d6) δ 10.71 (s, br, 1H, NH), 10.10 (s, br, 1H, NH), 7.57–7.61 (m, 2H), 7.17–7.22 (m, 2H), 7.06–7.09 (m, 2H), 6.97–7.0 (m, 1H), 6.88 (d, J=8.4 Hz, 1H), 3.52 (s, 2H).

2-Oxo-2,3-dihydro-1H-indole-5-sulfonic acid pyridin-3-ylamide

A solution of 5-chlorosufonyl-2-oxindole (3 g) and 3-aminopyridine (1.46 g) in pyridine (15 mL) was stirred at room temperature overnight at which time a brown solid was present. The solid was filtered, washed with ethanol and dried under vacuum to yield 1.4 g (38%) of 2-oxo-2,3-dihydro-1H-indole-5-sulfonic acid pyridin-3-ylamide.

$^1$HNMR (360 MHz, DMSO-d6) δ 10.74 (s, 1H, NH), 10.39 (s, 1H, SO$_2$NH), 8.27–8.28 (d, 1H), 8.21–8.23 (m, 1H), 7.59–7.62 (m, 2H), 7.44–7.68 (m, 1H), 7.24–7.28 (m, 1H), 6.69–6.71 (d, 1H), 3.54 (s, 2H).

MS m/z (APCI+) 290.2.

5-Phenyloxindole

5-Bromo-2-oxindole (5 g, 23.5 mmol) was dissolved in 110 mL toluene and 110 mL ethanol with stirring and a little heat. Tetrakis(triphenylphosphine)palladium(0) (1.9 g, 1.6 mmol) was added followed by 40 mL (80 mmol) 2M aqueous sodium carbonate. To this mixture was added benzene boronic acid (3.7 g, 30.6 mmol) and the mixture was heated in a 100° C. oil bath for 12 hours. The reaction was cooled, diluted with ethyl acetate (500 mL), washed with saturated sodium bicarbonate (200 mL), water (200 mL), 1N HCl (200 mL) and brine (200 mL). The organic layer was dried over magnesium sulfate and concentrated to afford a brown solid. Trituration with dichloromethane afforded 3.8 g (77%) of 5-phenyl-2-oxindole as a tan solid.

$^1$H NMR (360 MHz, DMSO-d6) δ 10.4 (br s, 1H, NH), 7.57 (dd, J=1.8 and 7.2 Hz, 1H), 7.5 to 7.35 (m, 5H), 7.29 (m, 1H), 6.89 (d, J=8.2 Hz, 1H), 3.51 (s, 2H, CH$_2$CO).

MS m/z 209 [M$^+$].

In similar fashion, the following oxindoles can be prepared:

6-(3,5-Dichlorophenyl)-1,3-dihydroindol-2-one $^1$H NMR (360 MHz, DMSO-d6) δ 10.46 (br, 1H, NH), 7.64 (d, J=1.8 Hz, 2H), 7.57 (m, 1H), 7.27 (m, 2H), 7.05 (d, J=1.1 Hz, 1H), 3.5 (s, 2H).

MS-EI m/z 277/279 [M]$^+$.

6-(4-Butylphenyl)-1,3-dihydroindol-2-one $^1$H NMR (360 MHz, DMSO-d6) δ 10.39 (s, 1H, NH), 7.49 (d, J=8.0 Hz, 2H), 7.25 (d, J=8 Hz, 3H), 7.17 (dd, J=1.5 and 7.8 Hz, 1H), 6.99 (d, J=1.5 Hz, 1H), 3.48 (s, 2H, CH$_2$CO), 2.60 (t, J=7.5 Hz, 2 Hz, CH$_2$CH$_3$), 1.57 (m, 2H, CH$_2$), 1.32 (m, 2H, CH$_2$), 0.9 (t, J=7.5 Hz, 3H, CH$_3$).

6-(5-Isopropyl-2-methoxyphenyl)-1,3-dihydroindol-2-one $^1$H NMR (360 MHz, DMSO-d6) δ 10.29 (br s, 1H, NH), 7.16–7.21 (m, 2H), 7.08 (d, J=2.4 Hz, 1H), 6.97–7.01 (m, 2H), 6.89 (d, J=0.8 Hz, 1H), 3.71 (s, 3H, OCH$_3$), 3.47 (s, 2H, CH$_2$CO), 2.86 (m, 1H, CH(CH$_3$)$_2$), 1.19 (d, J=6.8 Hz, 6H, CH(CH$_3$)$_2$).

MS-EI m/z 281 [M]$^+$.

6-(4-Ethylphenyl)-1,3-dihydroindol-2-one $^1$H NMR (360 MHz, DMSO-d6) δ 10.39 (br s, 1H, NH), 7.50 (d, J=8.2 Hz, 2H), 7.28 (d, J=8.2 Hz, 2H), 7.25 (d, J=7.5 Hz, 1H), 7.17 (dd, J=1.6 & 7.5 Hz, 1H), 6.99 (d, J=1.6 Hz, 1H), 3.48 (s, 2H, CH$_2$CO), 2.63 (q, J=7.6 Hz, 2H, CH$_2$CH$_3$), 1.20 (t, J=7.6 Hz, 3H, CH$_2$CH$_3$).

MS-EI m/z 237 [M]$^+$.

6-(3-Isopropylphenyl)-1,3-dihydroindol-2-one $^1$H NMR (360 MHz, DMSO-d6) δ 10.37 (br s, 1H, NH), 7.43 (m, 1H), 7.35–7.39 (m, 1H), 7.17–7.27 (m, 3H), 7.01 (d, J=1.8 Hz, 1H), 3.49 (s, 2H, CH$_2$CO), 2.95 (m, 1H, CH(CH$_3$)$_2$), 1.24 (d, J=6.8 Hz, 6H, CH(CH$_3$)$_2$).

MS-EI m/z 251 [M]$^+$.

6-(2,4-Dimethoxyphenyl)-1,3-dihydroindol-2-one $^1$H NMR (360 MHz, DMSO-d6) δ 810.28 (br s, 1H, NH), 7.17 (m, 2H), 6.93 (dd, J=1.6 & 7.6 Hz, 1H), 6.86 (d, J=1.6 Hz, 1H), 6.63 (d, J=2.4 Hz, 1H), 6.58 (dd, J=2.4 & 8.5 Hz, 1H), 3.79 (s, 3H, OCH$_3$), 3.74 (s, 3H, OCH$_3$), 3.45 (s, 2H, CH$_2$CO).

MS-EI m/z 269 [M]$^+$.

6-Pyridin-3-yl-1,3-dihydroindol-2-one $^1$H NMR (360 MHz, DMSO-d6) δ 10.51 (s, 1H, NH), 8.81 (d, J=2.5 Hz, 1H), 8.55 (dd, J=1.8 and 5.7 Hz, 1H), 8 (m, 1H), 7.45 (dd, J=5.7 and 9.3 Hz, 1H), 7.3 (m, 2H), 7.05 (s, 1H), 3.51 (s, 2H, CH$_2$CO).

MS m/z 210 [M]$^+$.

2-Oxo-2,3-dihydro-1H-indole-4-carboxylic acid (3-chloro-4-ethoxyphenyl)-amide To a solution of 4-carboxy-2-oxindole (200 mg, 1.13 mmol) and 3-chloro-4-methoxyphenylamine (178 mg, 1.13 mmol) in dimethylformamide (15 mL) at room temperature was added benzotriazol-1-yloxytris(dimethylamino)phosphonium hexafluorophosphate (BOP reagent, 997 mg, 2.26 mmol) followed by 4-dimethylaminopyridine (206 mg, 1.69 mmol). The mixture was stirred at room temperature for 72 hours. The reaction was then diluted with ethyl acetate (300 mL), washed with saturated sodium bicarbonate (100 mL), water, 2N hydrochloric acid (100 mL), water (3×200 mL) and brine. It was then dried over magnesium sulfate and concentrated. The residue was triturated with ethyl acetate to give 2-oxo-2,3-dihydro-1H-indole-4-carboxylic acid (3-chloro-4-methoxyphenyl)-amide as a pink solid.

$^1$HNMR (360 MHz, DMSO-d6) δ 10.50 (s, br, 1H, NH), 10.12 (s, br, 1H, NH), 7.9 (s, J=2.5 Hz, 1H), 7.62 (dd, J=2.5 & 9 Hz, 1H), 7.38 (d, J=7.6 Hz, 1H), 7.32 (t, J=7.6 Hz, 1H), 7.13 (d, J=9 Hz, 1H), 6.98 (d, J=7.6 Hz, 1H), 3.83 (s, 3H, OCH$_3$), 3.69 (s, 3H, CH$_2$).

MS-EI m/z 316 [M]$^+$.

4-Carboxy-2-oxindole

A solution of trimethylsilyldiazomethane in hexane (2 M) was added dropwise to a solution of 2.01 g 2-chloro-3-carboxy-nitrobenzene in 20 mL methanol at room temperature until no further gas evolution occurred. Acetic acid was then added to quench excess trimethylsilyldiazomethane. The reaction mixture was evaporated under vacuum and the residue was dried in an oven overnight. The 2-chloro-3-methoxycarbonylnitrobenzene obtained was pure enough for the following reaction.

Dimethyl malonate (6.0 mL) was added to an ice-cold suspension of 2.1 g sodium hydride in 15 mL DMSO. The reaction mixture was stirred at 100° C. for 1 hour and then cooled to room temperature. 2-Chloro-3-methoxycarbonylnitrobenzene (2.15 g) was added in one portion and the mixture was heated to 100° C. for 1.5 hours. The reaction mixture was then cooled to room temperature, poured into ice water, acidified to pH 5 and extracted with ethyl acetate. The organic layer was washed with brine, dried over anhydrous sodium sulfate and concentrated to give 3.0 g of the dimethyl 2-methoxycarbonyl-6-nitrophenyl-malonate.

Dimethyl 2-methoxycarbonyl-6-nitrophenylmalonate (3.0 g) was refluxed in 50 mL of 6 N hydrochloric acid overnight. The mixture was concentrated to dryness, 20 mL ethanol and 1.1 g of tin(II) chloride were added and the mixture was refluxed for 2 hours. The mixture was filtered through Celite, concentrated and chromatographed on silica gel using ethyl acetate:hexane:acetic acid as eluent to give 0.65 g (37%) of 4-carboxy-2-oxindole as a white solid.

$^1$HNMR (360 MHz, DMSO-d6) δ 12.96 (s, br, 1H, COOH), 10.74 (s, br, 1H, NH), 7.53 (d, J=8 Hz, 1H), 7.39 (t, J=8 Hz, 1H), 7.12 (d, J=8 Hz, 1H), 3.67 (s, 2H).

Syntheses of Compounds of Formula (II)

Example 1

Synthesis of 4-Methyl-5-(2-oxo-1,2-dihydroindol-3-ylidenemethyl)-1H-pyrrole-2-carboxylic acid 4-Methyl-2-pyrrolecarboxylic acid ethyl ester (commercially available) was formylated using method A to give (73%) of 5-formyl-4-methyl-2-pyrrolecarboxylic acid ethyl ester. It was then hydrolysed using method B to give 5-formyl-4-methyl-1H-pyrrole-2-carboxylic acid (58%).

Oxindole (133 mg, 1 mmol) was condensed with 5-formyl-4-methyl-1H-pyrrole-2-carboxylic acid (153 mg) using method D to give 268 mg (100%) of the title compound as an orange-red solid.

$^1$HNMR (360 MHz, DMSO-d6) δ 13.84 (s, br, 1H, NH), 12.84 (s, br, 1H, COOH), 10.98 (s, br, 1H, NH), 7.82 (d, J=7.5 Hz, 1H), 7.67 (s, 1H, H-vinyl), 7.18 (t, J=7.5 Hz, 1H), 7.01 (t, J=7.5 Hz, 1H), 6.88 (d, J=7.5 Hz, 1H), 6.71 (d, J=2.2 Hz, 1H), 2.32 (s, 3H, CH$_3$).

MS (negative mode) 266.8 [M−1]$^+$.

Example 2

Synthesis of 4-Methyl-5-(2-oxo-1,2-dihydroindol-3-ylidenemethyl)-1H-pyrrole-2-carboxylic acid methyl ester Oxindole (105 mg, 0.79 mmol) was condensed with 5-formyl-4-methyl-1H-pyrrole-2-carboxylic acid methyl ester (110 mg, 0.67 mmol) using method E to give 153.2 mg (81%) of the title compound.

¹HNMR (360 MHz, DMSO-d6) δ 13.98 (s, br, 1H, NH), 10.97 (s, br, 1H, NH), 7.82 (d, J=7.6 Hz, 1H), 7.67 (s, 1H, H-vinyl), 7.2 (dt, J=1.2 & 7.7 Hz, 1H), 7.01 (dt, J=1.2, 7.7 Hz, 1H), 6.90 (d, J=7.6 Hz, 1H), 6.77 (d, J=2 Hz, 1H).

MS (ES) m/z 283 [M$^+$+1].

Example 3

Synthesis of 5-(5-Chloro-2-oxo-1,2-dihydroindol-3-ylidenemethyl)-4-methyl-1H-pyrrole-2-carboxylic acid ethyl ester 5-Chloro-1,3-dihydroindol-2-one (2.22 g, 13.2 mmol) was condensed with 5-formyl-4-methyl-1H-pyrrole-2-carboxylic acid ethyl ester (2.43 g) using method E to give 4.1 g (94%) of the title compound as an orange solid.

¹HNMR (360 MHz, DMSO-d6) δ 13.95 (s, br, 1H, NH), 7.98 (d, J=2.2 Hz, 1H, H-4), 7.78 (s, 1H, H-vinyl), 7.18 (dd, J=2.2 & 8.3 Hz, 1H, H-6), 6.87 (d, J=8.3 Hz, 1H, H-7), 7.34 (d, J=1.8 Hz, 1H, H-3'), 4.27 (q, J=7.2 Hz, 2H, OCH$_2$CH$_3$), 2.33 (s, 3H, CH$_3$), 1.29 (t, J=7.2 Hz, 3H, OCH$_2$CH$_3$).

MS-EI m/z 330 [M$^+$].

Example 4

Synthesis of 5-(5-Chloro-2-oxo-1,2-dihydroindol-3-ylidenemethyl)-4-methyl-1H-pyrrole-2-carboxylic acid A mixture of 5-(5-chloro-2-oxo-1,2-dihydroindol-3-ylidenemethyl)-4-methyl-1H-pyrrole-2-carboxylic acid ethyl ester (1.3 g, 4 mmol) and potassium hydroxide in methanol (25 mL) and ethanol (25 mL) was heated to reflux for overnight. Insoluble materials were removed by filtration and the mixture was neutralized with 6N hydrochloric acid to give 0.876 g (70%) of the title compound.

¹HNMR (360 MHz, DMSO-d6) δ 13.80 (s, br, 1H, NH), 12.90 (s, br, 1H, COOH), 11.06 (s, br, 1H, NH), 8.02 (d, J=1.8 Hz, 1H, H-4), 7.81 (s, 1H, H-vinyl), 7.20 (dd, J=1.8 & 8.3 Hz, 1H, H-6), 6.89 (d, J=8.3 Hz, 1H, H-7), 6.72 (d, J=1.8 Hz, 1H, H-3'), 2.35 (s, 3H, CH$_3$).

MS-EI m/z 302 [M$^+$].

Example 5

Synthesis of 5-(5-Bromo-2-oxo-1,2-dihydroindol-3-ylidenemethyl)-2-isopropyl-4-phenyl-1H-pyrrole-3-carboxylic acid (3-diethylaminopropyl)amide A mixture of 2-aminoacetophenone hydrochloride (1 equiv.), ethyl isobutyrylacetate (1.2 equiv.) and sodium acetate (2.4 equiv.) in H$_2$O was stirred at 100° C. for 18 hours and then cooled to room temperature. The aqueous layer was decanted off and the oil was dissolved in ethyl acetate. It was then washed with water and brine and then dried to give (93%) of 2-isopropyl-4-phenyl-1H-pyrrole-3-carboxylic acid ethyl ester as a red brown oil.

¹HNMR (300 MHz, DMSO-d6) δ 11.21 (s, br, 1H, NH), 7.14–7.27 (m, 5H), 6.70 (d, J=2.7 Hz, 1H), 4.02 (q, J=7.1 Hz, 2H, OCH$_2$CH$_3$), 3.65 (m, 1H, CH(CH$_3$)$_2$), 1.22 (d, J=7.5 Hz, 6H, CH(CH$_3$)$_2$), 1.04 (t, J=7.1 Hz, 3H, OCH$_2$CH$_3$).

MS-EI m/z 257 [M$^+$].

The above pyrrole was formylated using method A to give (41%) 5-formyl-2-isopropyl-4-phenyl-1H-pyrrole-3-carboxylic acid ethyl ester as a reddish solid.

¹HNMR (300 MHz, DMSO-d6) δ 12.35 (s, br, 1H, NH), 9.14 (s, 1H, CHO), 7.36 (s, 5H), 3.96 (q, J=7.1 Hz, 2H, OCH$_2$CH$_3$), 3.74 (m, 1H, CH(CH$_3$)$_2$), 1.29 (d, J=6.9 Hz, 6H, CH(CH$_3$)$_2$), 0.90 (t, J=7.1 Hz, 3H, OCH$_2$CH$_3$).

MS-EI m/z 285 [M$^+$].

The pyrrolecarboxylic acid ester was hydrolysed using method B to give (57%) of 5-formyl-2-isopropyl-4-phenyl-1H-pyrrole-3-carboxylic acid as a beige solid.

¹HNMR (300 MHz, DMSO-d6) δ 12.28 (s, br, 1H, COOH), 12.02 (s, br, 1H, NH), 9.10 (s, 1H, CHO), 7.35 (s, 5H), 3.81 (m, 1H, CH(CH$_3$)$_2$), 1.28 (d, J=6.9 Hz, 6H, CH(CH$_3$)$_2$).

MS-EI m/z 257 [M$^+$].

5-Bromo-1,3-dihydroindol-2-one (120 mg, 0.31 mmol) was condensed with 5-formyl-2-isopropyl-4-phenyl-1H-pyrrole-3-carboxylic acid (3-diethylaminopropyl)amide (prepared by method C) to give 120 mg (71%) of the title compound.

¹HNMR (300 MHz, DMSO-d6) δ 14.23 (s, br, 1H, NH), 11.08 (s, br, 1H, NH), 7.38–7.55 (m, 7H, Ar—H & CONHCH$_2$), 7.30 (s, 1H, H-vinyl), 7.26 (dd, J=1.8 & 7.8 Hz, 1H), 6.85 (d, J=8.7 Hz, 1H), 3.36 (m, 1H, CH(CH$_3$)$_2$), 3.07 (m, 2H, CH$_2$), 2.34 (q, J=7.1 Hz, 4H, N(CH$_2$CH$_3$)$_2$), 2.22 (t, J=6.9 Hz, 2H, CH$_2$), 1.40 (m, 2H, CH$_2$), 1.31 (d, J=6.9 Hz, 6H, CH(CH$_3$)$_2$), 0.86 (t, J=7.1 Hz, 6H, N(CH$_2$CH$_3$)$_2$).

MS m/z 565.1 [M$^+$+1].

Example 6

Synthesis of 5-(5-Bromo-2-oxo-1,2-dihydroindol-3-ylidenemethyl)-2-isopropyl-4-phenyl-1H-pyrrole-3-carboxylic acid (3-pyrrolidin-1-ylpropyl)amide 5-(5-bromo-2-oxo-1,2-dihydroindol-3-ylidenemethyl)-2-isopropyl-4-phenyl-1H-pyrrole- 3-carboxylic acid (127 mg, 0.28 mmol) was condensed with 3-pyrrolidin-1-yl-propylamine (43 mg, 0.336 mmol) to give 140 mg (66%) of the title compound.

¹HNMR (300 MHz, DMSO-d6) δ 14.40 (s, br, 1H, NH), 7.38–7.47 (m, 7H), 7.23–7.27 (m, 2H), 6.84 (d, J=8.1 Hz, 1H), 3.36 (m, 1H, CH(CH$_3$)$_2$), 3.08 (m, 2H, CH$_2$), 2.30 (m, 4H, 2×CH$_2$), 2.20 (t, J=7.0 Hz, 2H, CH$_2$), 1.62 (m, 4H, 2×CH$_2$), 1.42 (t, J=7.0 Hz, 2H, CH$_2$), 1.31 (d, J=7.2 Hz, 6H, CH(CH$_3$)$_2$).

MS-EI m/z 560 and 562 [M$^+$−1 and M$^+$+1].

Example 7

Synthesis of 5-(5-Bromo-2-oxo-1,2-dihydroindol-3-ylidenemethyl)-2-isopropyl-4-phenyl-1H-pyrrole-3-carboxylic acid (2-diethylaminoethyl)amide 5-Bromo-1,3-dihydroindol-2-one (57, g. 0.27 mmol) was condensed with 5-formyl-2-isopropyl-4-phenyl-1H-pyrrole-3-carboxylic acid (2-diethylaminoethyl)amide (120 mg) to give 78 mg (53%) of the title compound as a yellow solid.

¹HNMR (300 MHz, DMSO-d6) δ 14.23 (s, br, 1H, NH), 11.09 (s, br, 1H, NH), 7.38–7.51 (m, 6H), 7.25–7.28 (m, 2H), 7.19 (t, 1H, CONHCH$_2$), 6.85 (d, J=7.8 Hz, 1H), 3.43 (m, 1H, CH(CH$_3$)$_2$), 3.11 (m, 2H, CH$_2$), 2.28–2.39 (m, 6H, N(CH$_2$CH$_3$)$_2$ & CH$_2$, 1.31 (d, J=6.9 Hz, CH(CH$_3$)$_2$), 0.85 (t, J=7.0 Hz, 6H, N(CH$_2$CH$_3$)$_2$.

MS-EI m/z 548 and 550 [M$^+$−1 and M$^+$+1].

Example 8

Synthesis of 5-(5-Bromo-2-oxo-1,2-dihydroindol-3-ylidenemethyl)-2-isopropyl-4-phenyl-1H-pyrrole-3-carboxylic acid [3-(4-methylpiperazin-1-yl)propyl]amide 5-Bromo-1,3-dihydroindol-2-one (53 mg, 0.25 mmol) was condensed with 5-formyl-2-isopropyl-4-phenyl-1H-pyrrole-3-carboxylic acid [3-(4-methylpiperazin-1-yl)propyl]amide (300 mg) to give 65 mg of the title compound.

$^1$HNMR (300 MHz, DMSO-d6) δ 14.22 (s, br, 1H, NH), 11.08 (s, br, 1H, NH), 7.23–7.50 (m, 9H), 6.85 (d, J=8.7 Hz, 1H), 3.37 (m, 1H, CH(CH$_3$)$_2$), 3.05 (m, 2H, CH$_2$), 2.24 (m, 8H, 4×CH$_2$), 2.11 (m, 5H, CH$_2$ & CH$_3$), 1.42 (m, 2H, CH$_2$), 1.31 (d, J=7.2 Hz, 6H, CH(CH$_3$)$_2$).

MS-EI m/z 589 and 591 [M$^+$−1 and M$^+$+1].

Example 9

Synthesis of 5-(5-Bromo-2-oxo-1,2-dihydroindol-3-ylidenemethyl)-2-isopropyl-4-phenyl-1H-pyrrole-3-carboxylic acid 5-Bromo-1,3-dihydroindol-2-one (170 mg, 0.8 mmol) was condensed with 5-formyl-2-isopropyl-4-phenyl-1H-pyrrole-3-carboxylic acid (205 mg) using method D to give 210 mg (58%) of the title compound as a yellow solid.

$^1$HNMR (300 MHz, DMSO-d6) δ 14.31 (s, br, 1H, NH), 11.16 (s, br, 1H, NH), 7.26–7.44 (m, 7H), 7.11 (s, 1H, H-vinyl), 6.85 (d, J=7.8 Hz, 1H), 3.78 (m, 1H, CH(CH$_3$)$_2$), 1.34 (d, J=6.9 Hz, 6H, CH(CH$_3$)$_2$).

MS-EI m/z 452 [M$^+$+1].

Example 10

Synthesis of 5-(5-Bromo-2-oxo-1,2-dihydroindol-3-ylidenemethyl)-2-methyl-4-phenyl-1H-pyrrole-3-carboxylic acid (2-pyrrolidin-1-ylethyl)amide 5-Bromo-1,3-dihydroindol-2-one (44 mg, 0.21 mmol) was condensed with 5-formyl-2-methyl-4-phenyl-1H-pyrrole-3-carboxylic acid (2-pyrrolidin-1-ylethyl)amide (70 mg, prepared in the same manner as the isopropyl analog, above) to give 0.03 g (27%) of the title compound as a yellow solid.

$^1$HNMR (300 MHz, DMSO-d6) δ 13.87 (s, br, 1H, NH), 11.11 (s, br, 1H, NH), 7.36–7.51 (m, 6H), 7.26 (dd, J=1.8 & 8.1 Hz, 1H), 7.2 (s, 1H, H-vinyl), 7.09 (m, 1H, CONHCH$_2$), 6.83 (d, J=8.1 Hz, 1H), 3.17 (m, 2H, NCH$_2$), 2.48 (m, CH$_3$), 2.29–2.35 (m, 6H, 3×NCH$_2$), 1.59 (m, 4H, 2×CH$_2$).

MS-EI m/z 518 and 520 [M$^+$−1 and M$^+$+1].

Example 11

Synthesis of 5-[6-(2-Methoxyphenyl)-2-oxo-1,2-dihydroindol-3-ylidenemethyl]-2-methyl-4-phenyl-1H-pyrrole-3-carboxylic acid (2-pyrrolidin-1-ylethyl)amide 6-(2-Methoxyphenyl)-1,3-dihydroindol-2-one (50 mg, 0.21 mmol) was condensed with 5-formyl-2-methyl-4-phenyl-1H-pyrrole-3-carboxylic acid (2-pyrrolidin-1-ylethyl)amide (70 mg) to give 0.04 g (35%) of the title compound as a yellow-orange solid.

$^1$HNMR (300 MHz, DMSO-d6) δ 13.82 (s, br, 1H, NH), 11.02 (s, br, 1H, NH), 7.48 (m, 2H), 7.43 (m, 1H), 7.38 (m, 2H), 7.32 (m, 1H), 7.24 (m, 2H), 7.16 (s, 1H, H-vinyl), 7.08 (m, 2H), 7.03 (m, 1H), 7.0 (m, 2H), 3.74 (s, 3H, OCH$_3$), 3.19 (m, 2H, NCH$_2$), 2.49 (m, CH$_3$), 2.32–2.38 (m, 6H, 3×NCH$_2$), 1.59 (m, 4H, 2×CH$_2$).

MS-EI m/z 546 [M$^+$].

Example 12

Synthesis of 5-(5-Bromo-2-oxo-1,2-dihydroindol-3-ylidenemethyl)-2-methyl-4-phenyl-1H-pyrrole-3-carboxylic acid (2-dimethylaminoethyl)amide 5-Bromo-1,3-dihydroindol-2-one (46 mg, 0.22 mmol) was condensed with 5-formyl-2-methyl-4-phenyl-1H-pyrrole-3-carboxylic acid (2-dimethylaminoethyl)amide (65 mg) to give 60 mg (55%) of the title compound as a yellow solid.

$^1$HNMR (360 MHz, DMSO-d6) δ 13.86 (s, br, 1H, NH), 11.09 (s, br, 1H, NH), 7.47–7.49 (m, 2H), 7.38–7.41 (m, 4H), 7.26 (dd, J=2.2 & 8.3 Hz, 1H), 7.21 (s, 1H, H-vinyl), 7.04 (m, 1H, CONHCH$_2$), 6.77 (d, J=8.3 Hz, 1H), 3.15 (m, 2H, NCH$_2$), 2.48 (m, CH$_3$), 2.16 (t, J=6.8 Hz, 2H, 3×NCH$_2$), 2.02 (s, 6H, 2×NCH$_3$).

MS m/z 493 and 494.8 [M$^+$ and M$^+$+2].

Example 13

Synthesis of 5-[6-(2-Methoxyphenyl)-2-oxo-1,2-dihydroindol-3-ylidenemethyl]-2-methyl-4H-pyrrole-3-carboxylic acid (2-dimethylaminoethyl)amide 6-(2-Methoxyphenyl)-1,3-dihydroindol-2-one (53 mg, 0.22 mmol) was condensed with 5-formyl-2-methyl-4-phenyl-1H-pyrrole-3-carboxylic acid (2-dimethylaminoethyl)amide (65 mg) to give 0.05 g (44%) of the title compound as an orange gum.

$^1$HNMR (300 MHz, DMSO-d6) δ 13.82 (s, br, 1H, NH), 11.02 (s, br, 1H, NH), 7.37–7.52 (m, 5H), 7.32 (m, 1H), 7.22–7.27 (m, 2H), 7.16 (s, 1H), 7.08 (m, 2H), 7.03 (m, 1H), 7.0 (m, 2H), 3.74 (s, 3H, OCH$_3$), 3.15 (m, 2H, NCH$_2$), 2.49 (m, CH$_3$), 2.16 (t, J=6.5 Hz, 2H, NCH$_2$), 2.02 (s, 6H, 2×NCH$_3$).

MS m/z 521 [M$^+$+1].

Example 14

Synthesis of 5-(5-Bromo-2-oxo-1,2-dihydroindol-3-ylidenemethyl)-2-methyl-4-phenyl-1H-pyrrole-3-carboxylic acid ethyl ester 5-Bromo-1,3-dihydroindol-2-one (60 mg, 0.29 mmol) was condensed with 5-formyl-2-methyl-4-phenyl-1H-pyrrole-3-carboxylic acid ethyl ester (75 mg) to give 78 mg (60%) of the title compound as an orange solid.

$^1$HNMR (360 MHz, DMSO-d6) δ 14.01 (s, br, 1H, NH), 11.13 (s, br, 1H, NH), 7.42–7.46 (m, 3H), 7.27–7.34 (m, 4H), 7.12 (s, 1H), 6.84 (dd, J=2.2 & 8.3 Hz, 1H), 3.99–4.03 (m, 2H, OCH$_2$CH$_3$), 2.61 (s, 3H, CH$_3$), 0.98–1.03 (m, 3H, OCH$_2$CH$_3$).

MS-EI m/z 450 and 452 [M$^+$−1 and M$^+$+1].

Example 15

Synthesis of 5-(5-Bromo-2-oxo-1,2-dihydroindol-3-ylidenemethyl)-2-methyl-4-phenyl-1H-pyrrole-3-carboxylic acid (3-diethylaminopropyl)amide 5-bromo-1,3-dihydroindol-2-one (0.47 g, 2.2 mmol) was condensed with 5-formyl-2-methyl-4-phenyl-1H-pyrrole-3-carboxylic acid (3-diethylaminopropyl)amide (0.75 g) to give 0.11 g (42%) of the title compound as an orange solid.

$^1$HNMR (300 MHz, DMSO-d6) δ 13.86 (s, br, 1H, NH), 7.42–7.46 (m, 3H), 7.37–7.50 (m, 7H), 7.24–7.28 (m, 2H), 6.83 (d, J=8.1 Hz, 1H), 3.09 (m, 2H, NCH$_2$), 2.45 (s, 3H, CH$_3$), 2.38 (q, J=7.1 Hz, 4H, 2×NCH$_2$CH$_3$), 2.26 (t, J=6.9 Hz, 2H, NCH$_2$), 1.42 (m, 2H, NCH$_2$), 0.87 (t, J=7.1 Hz, 6H, 2×NCH$_2$CH$_3$).

MS-EI m/z 535.0 and 537 [M$^+$ and M$^+$+2].

Example 16

Synthesis of 5-(5-Bromo-2-oxo-1,2-dihydroindol-3-ylidenemethyl)-2,4-dimethyl-1H-pyrrole-3-carboxylic acid (2-dimethylamino-ethyl)amide A mixture of tert-butyl 3-oxobutyrate and sodium nitrite (1 equiv.) in acetic acid was stirred at room temperature to give tert-butyl-2-hydroximino-3-oxobutyrate.

Ethyl-3-oxobutyrate (1 equiv.), zinc dust (3.8 equiv.) and the crude tert-butyl-2-hydroximino-3-oxobutyrate in acetic acid was stirred at 60° C. for 1 hr. The reaction mixture was poured into H$_2$O and the filtrate was collected to give (65%) 2-tert-butyloxycarbonyl-3,5-dimethyl-4-ethoxycarbonylpyrrole.

A mixture of 2-tert-butyloxycarbonyl-3,5-dimethyl-4-ethoxycarbonylpyrrole and triethyl orthoformate (1.5 equiv.) in trifluoroacetic acid was stirred at 15° C. for 1 hour. The reaction was concentrated and the residue was purified to give (64%) 2,4-dimethyl-3-ethoxycarbonyl-5-formylpyrrole as yellow needles.

2,4-Dimethyl-3-ethoxycarbonyl-5-formylpyrrole was hydrolyzed using method B to give (90%) 5-formyl-2,4-dimethyl-1H-pyrrole-3-carboxylic acid.

$^1$H NMR (360 MHz, DMSO-d6) δ 12 (br s, 2H, NH and CO$_2$H), 9.58 (s, 1H, CHO), 2.44 (s, 3H, CH$_3$), 2.40 (s, 3H, CH$_3$).

MS m/z 267 [M$^+$].

5-Bromo-1,3-dihydroindol-2-one (0.17 g, 0.8 mmol) was condensed with 5-formyl-2,4-dimethyl-1H-pyrrole-3-carboxylic acid (2-dimethylaminoethyl)amide (0.2 g, prepared by method C) using method B to give 0.3 g (83%) of the title compound as a yellow solid.

$^1$HNMR (360 MHz, DMSO-d6) δ 13.60 (s, br, 1H, NH), 10.94 (s, br, 1H, NH), 8.07 (d, J=1.8 Hz, 1H, H-4), 7.75 (s, 1H, H-vinyl), 7.44 (t, J=5.2 Hz, 1H, CONHCH$_2$), 7.24 (dd, J=1.8 & 8.4 Hz, 1H, H-6), 6.82 (d, J=8.4 Hz, 1H, H-7), 3.26–3.33 (m, 2H, NCH$_2$), 2.42 (s, 3H, CH$_3$), 2.41 (s, 3H, CH$_3$), 2.38 (t, J=6.7 Hz, 2H, NCH$_2$), 2.18 (s, 6H, N(CH$_3$)$_2$).

MS-EI m/z 430 and 432 [M$^+$–1 and M$^+$+1].

Example 17

Synthesis of 2,4-Dimethyl-5-(2-oxo-6-phenyl-1,2-dihydroindol-3-ylidenemethyl)-1H-pyrrole-3-carboxylic acid (2-dimethylaminoethyl)amide 6-Phenyl-1,3-dihydroindol-2-one (0.17 g, 0.8 mmol) was condensed with 5-formyl-2,4-dimethyl-1H-pyrrole-3-carboxylic acid (2-dimethylaminoethyl)amide (0.2 g) to give 0.13 g (36%) of the title compound as a yellow-orange solid.

$^1$HNMR (360 MHz, DMSO-d6) δ 13.59 (s, br, 1H, NH), 10.93 (, br, 1H, NH), 7.85 (d, J=7.92 Hz, 1H, H-4), 7.63–7.65 (m, 3H), 7.40–7.47 (m, 3H,), 7.32–7.36 (m, 1H, Ar—H), 7.30 (dd, J=1.6 & 7.9 Hz, 1H, H-5), 7.11 (d, J=1.6 Hz, 1H, H-7), 3.28–3.34 (m, 2H, NCH$_2$), 2.43 (s, 3H, CH$_3$), 2.41 (s, 3H, CH$_3$), 2.38 (t, J=6.8 Hz, 2H, NCH$_2$), 2.18 (s, 6H, N(CH$_3$)$_2$).

MS-EI m/z 428 [M$^+$].

Example 18

Synthesis of 5-(5-Chloro-2-oxo-1,2-dihydroindol-3-ylidenemethyl)-2,4-dimethyl-1H-pyrrole-3-carboxylic acid (2-dimethylamino-ethyl)amide 5-Chloro-1,3-dihydroindol-2-one (0.1 g, 0.6 mmol) was condensed with 5-formyl-2,4-dimethyl-1H-pyrrole-3-carboxylic acid (2-dimethylaminoethyl)amide (0.15 g) to give 0.22 g (90%) of the title compound as a yellow solid.

$^1$HNMR (300 MHz, DMSO-d6) δ 13.61 (s, br, 1H, NH), 10.98 (, br, 1H, NH), 7.96 (d, J=2.0 Hz, 1H, H-4), 7.75 (s, 1H, H-vinyl), 7.50 (t, J=5.5 Hz, 1H, CONHCH$_2$), 7.12 (dd, J=2.0 & 8.3 Hz, 1H, H-6), 6.86 (d, J=8.3 Hz, 1H, H-7), 3.26–3.31 (m, 2H, NCH$_2$), 2.42 (s, 3H, CH$_3$), 2.40 (s, 3H, CH$_3$), 2.36 (t, J=6.6 Hz, 2H, NCH$_2$), 2.17 (s, 6H, N(CH$_3$)$_2$).

MS-EI m/z 386 [M$^+$].

Example 19

Synthesis of 5-(5-Bromo-2-oxo-1,2-dihydroindol-3-ylidenemethyl)-2,4-dimethyl-1H-pyrrole-3-carboxylic acid (2-diethylamino-ethyl)amide 5-Bromo-1,3-dihydroindol-2-one (0.17 g, 0.8 mmol) was condensed with 5-formyl-2,4-dimethyl-1H-pyrrole-3-carboxylic acid (2-diethylaminoethyl)amide (0.2 g) to give 0.09 g (26%) of the title compound as a yellow solid.

$^1$HNMR (360 MHz, DMSO-d6) δ 13.61 (s, br, 1H, NH), 10.98 (, br, 1H, NH), 8.09 (d, J=1.7 Hz, 1H, H-4), 7.76 (s, 1H, H-vinyl), 7.42 (t, J=5.5 Hz, 1H, CONHCH$_2$), 7.24 (dd, J=1.7 & 8.0 Hz, 1H, H-6), 6.82 (d, J=8.0 Hz, 1H, H-7), 3.23–3.32 (m, 2H, NCH$_2$), 2.46–2.55 (m, 6H, 3×NCH$_2$), 2.43 (s, 3H, CH$_3$), 2.42 (s, 3H, CH$_3$), 0.96 (t, J=7.2 Hz, 6H, 2×NCH$_2$CH$_3$).

MS-EI m/z 458 and 460 [M$^+$–1 and M$^+$+1].

Example 20

Synthesis of 5-(5-Bromo-2-oxo-1,2-dihydroindol-3-ylidenemethyl)-2,4-dimethyl-1H-pyrrole-3-carboxylic acid (2-pyrrolidin-1-yl-ethyl)amide 5-Bromo-1,3-dihydroindol-2-one (0.09 g, 0.4 mmol) was condensed with 5-formyl-2,4-dimethyl-1H-pyrrole-3-carboxylic acid (2-pyrrolidin-1-ylethyl)amide (0.1 g) to give 0.14 g (81%) of the title compound as a yellow-orange solid.

$^1$HNMR (300 MHz, DMSO-d6) δ 13.61 (s, br, 1H, NH), 10.98 (, br, 1H, NH), 8.09 (d, J=1.9 Hz, 1H, H-4), 7.76 (s, 1H, H-vinyl), 7.53 (t, J=5.5 Hz, 1H, CONHCH$_2$), 7.24 (dd, J=1.9 & 8.5 Hz, 1H, H-6), 6.81 (d, J=8.5 Hz, 1H, H-7), 3.29–3.35 (m, 2H, NCH$_2$), 2.54 (t, J=6.9 Hz, 2H, NCH$_2$), 2.47 (m, under DMSO), 2.42 (s, 3H, CH$_3$), 2.40 (s, 3H, CH$_3$), 1.66–1.69 (m, 4H, 2×CH$_2$).

MS-EI m/z 456 and 458 [M$^+$–1 and M$^+$+1].

Example 21

Synthesis of 5-(5-Bromo-2-oxo-1,2-dihydroindol-3-ylidenemethyl)-2,4-dimethyl-1H-pyrrole-3-carboxylic acid (3-imidazol-1-yl-propyl)amide 5-Bromo-1,3-dihydroindol-2-one (0.09 g, 0.4 mmol) was condensed with 5-formyl-2,4-dimethyl-1H-pyrrole-3-carboxylic acid (3-imidazol-1-ylpropyl)amide (0.1 g) to give 0.1 g (59%) of the title compound as an orange solid.

$^1$HNMR (300 MHz, DMSO-d6) δ 13.63 (s, br, 1H, NH), 10.99 (, br, 1H, NH), 8.09 (d, J=2.2 Hz, 1H, H-4), 7.77 (s, 1H, H-vinyl), 7.71 (t, J=5.7 Hz, 1H, CONHCH$_2$), 7.65 (s, 1H, Ar—H), 7.25 (dd, J=2.2 & 8.4 Hz, 1H, H-6), 7.20 (s, 1H, Ar—H), 6.89 (s, 1H, Ar—H), 6.81 (d, J=8.4 Hz, 1H, H-7), 4.02 (t, J=6.7 Hz, 2H, NCH$_2$), 3.18 (q, J=6.7 Hz, 2H, NCH$_2$), 2.43 (s, 3H, CH$_3$), 2.41 (s, 3H, CH$_3$), 1.93 (m, 2H, CH$_2$).

MS-EI m/z 467 and 469 [M$^+$−1 and M$^+$+1].

Example 22

Synthesis of 5-[6-(2-Methoxyphenyl)-2-oxo-1,2-dihydroindol-3-ylidenemethyl]-2,4-dimethyl-1H-pyrrole-3-carboxylic acid (2-dimethylaminoethyl)amide 6-(2-Methoxyphenyl)-1,3-dihydroindol-2-one (30 mg, 0.13 mmol) was condensed with 5-formyl-2,4-dimethyl-1H-pyrrole-3-carboxylic acid (2-dimethylaminoethyl)amide (30 mg) to give 0.06 g (100%) of the title compound as a yellow-orange gum.

$^1$HNMR (300 MHz, DMSO-d6) δ 13.60 (s, br, 1H, NH), 10.89 (s, br, 1H, NH), 7.79 (d, J=8.4 Hz, 1H), 7.63 (s, 1H, H-vinyl), 7.46 (t, J=5.5 Hz, 1H, CONHCH$_2$), 7.28–7.35 (m, 2H), 6.99–7.11 (m, 4H), 3.76 (s, 3H, OCH$_3$), 3.27–3.31 (m, 2H, NCH$_2$), 2.43 (s, 3H, CH$_3$), 2.39 (s, 3H, CH$_3$), 2.37 (m, 2H, NCH$_2$), 2.18 (s, 6H, N(CH$_3$)$_2$).

MS-EI m/z 458 [M$^+$].

Example 23

Synthesis of 5-[6-(3-Methoxyphenyl)-2-oxo-1,2-dihydroindol-3-ylidenemethyl]-2,4-dimethyl-1H-pyrrole-3-carboxylic acid (2-dimethylaminoethyl)amide 6-(3-Methoxyphenyl)-1,3-dihydroindol-2-one (30 mg, 0.13 mmol) was condensed with 5-formyl-2,4-dimethyl-1H-pyrrole-3-carboxylic acid (2-dimethylaminoethyl)amide (30 mg) to give 8 mg (14%) of the title compound as a yellow-orange solid.

$^1$HNMR (360 MHz, DMSO-d6) δ 13.59 (s, br, 1H, NH), 10.92 (s, br, 1H, NH), 7.84 (d, J=7.6 Hz, 1H), 7.65 (s, 1H, H-vinyl), 7.42 (m, 1H, CONHCH$_2$), 7.36 (d, J=7.8 Hz, 1H), 7.29 (dd, J=1.6 & 7.6 Hz, 1H), 7.20 (d, J=7.8 Hz, 1H), 7.14 (d, J=2.8 Hz, 1H), 7.11 (d, J=1.6 Hz, 1H), 6.91 (dd, J=2.8 & 7.8 Hz, 1H), 3.82 (s, 3H, OCH$_3$), 3.21–3.33 (m, 2H, NCH$_2$), 2.43 (s, 3H, CH$_3$), 2.40 (s, 3H, CH$_3$), 2.36–2.40 (m, 2H, NCH$_2$), 2.18 (s, 6H, N(CH$_3$)$_2$).

MS-EI m/z 458 [M$^+$].

Example 24

Synthesis of 2,4-Dimethyl-5-(2-oxo-5-phenyl-1,2-dihydroindol-3-ylidenemethyl)-1H-pyrrole-3-carboxylic acid (2-diethylamino-ethyl)amide 5-Phenyl-1,3-dihydroindol-2-one (80 mg, 0.4 mmol) was condensed with 5-formyl-2,4-dimethyl-1H-pyrrole-3-carboxylic acid (2-diethylaminoethyl)amide (0.1 g) using method B to give 79 mg (46%) of the title compound.

$^1$HNMR (300 MHz, DMSO-d6) δ 13.66 (s, br, 1H, NH), 10.95 (, br, 1H, NH), 8.15 (d, J=1.2 Hz, 1H), 7.81 (s, 1H, H-vinyl), 7.71 (d, J=7.5 Hz, 1H), 7.40–7.47 (m, 4H), 7.31 (m, 1H), 6.95 (d, J=8.1 Hz, 1H), 3.2–3.31 (m, 2H, NCH$_2$), 2.46–2.55 (m, 6H, 3×NCH$_2$), 2.44 (s, 6H, 2×CH$_3$), 0.96 (t, J=7.4 Hz, 6H, 2×NCH$_2$CH$_3$).

MS-EI m/z 456 [M$^+$].

Example 25

Synthesis of 2,4-Dimethyl-5-(2-oxo-5-phenyl-1,2-dihydroindol-3-ylidenemethyl)-1H-pyrrole-3-carboxylic acid (2-pyrrolidin-1-ylethyl)amide 5-Phenyl-1,3-dihydroindol-2-one (0.04 g, 0.2 mmol) was condensed with 5-formyl-2,4-dimethyl-1H-pyrrole-3-carboxylic acid (2-pyrrolidin-1-ylethyl)amide (0.04 g) to give the title compound as a yellow-orange solid.

$^1$HNMR (300 MHz, DMSO-d6) δ 13.65 (s, br, 1H, NH), 10.96 (, br, 1H, NH), 8.15 (d, J=1.0 Hz, 1H), 7.80 (s, 1H, H-vinyl), 7.71 (d, J=7.2 Hz, 2H), 7.49 (t, J=6.3 Hz, 1H, CONHCH$_2$), 7.41–7.46 (m, 3H), 7.31 (m, 1H), 6.95 (d, J=7.8 Hz, 1H), 4.08 (m, 4H, 2×NCH$_2$), 3.32 (m, 2H, NCH$_2$), 2.55 (t, J=7.1 Hz, 2H, NCH$_2$), 2.47 (m, under DMSO), 2.43 (s, 6H, 2×CH$_3$), 1.66 (m, 4H, 2×CH$_2$).

MS-EI m/z 454 [M$^+$].

Example 26

Synthesis of 2,4-dimethyl-5-(2-oxo-5-phenyl-1,2-dihydroindol-3-ylidenemethyl)-1H-pyrrole-3-carboxylic acid (3-imidazol-1-ylpropyl)amide 5-Phenyl-1,3-dihydroindol-2-one (8 mg, 0.04 mmol) was condensed with 5-formyl-2,4-dimethyl-1H-pyrrole-3-carboxylic acid (3-imidazol-1-ylpropyl)amide (10 mg) to give 10 mg (59%) of the title compound as an orange solid.

$^1$HNMR (300 MHz, DMSO-d6) δ 13.67 (s, br, 1H, NH), 10.96 (, br, 1H, NH), 8.16 (d, J=1.2 Hz, 1H), 7.81 (s, 1H, H-vinyl), 7.65–7.72 (m, 4H), 7.44 (m, 3H), 7.31 (m, 1H, CONHCH$_2$), 7.21 (s, 1H, Ar—H), 4.02 (t, J=6.5 Hz, 2H, NCH$_2$), 3.19 (q, J=6.5 Hz, 2H, CONHCH$_2$), 2.44 (s, 6H, 2×CH$_3$), 1.93 (m, 2H, CH$_2$CH$_2$ CH$_2$).

MS-EI m/z 465 [M$^+$].

Example 27

Synthesis of 2,4-dimethyl-5-(2-oxo-6-phenyl-1,2-dihydroindol-3-ylidenemethyl)-1H-pyrrole-3-carboxylic acid (2-diethylaminoethyl)amide 6-Phenyl-1,3-dihydroindol-2-one (0.08 g, 0.4 mmol) was condensed with 5-formyl-2,4-dimethyl-1H-pyrrole-3-carboxylic acid (2-diethylaminoethyl)amide (0.1 g) to give 65 mg (38%) of the title compound as a yellow solid.

$^1$HNMR (300 MHz, DMSO-d6) δ 13.61 (s, br, 1H, NH), 10.99 (, br, 1H, NH), 7.86 (d, J=7.8 Hz, 1H), 7.62–7.66 (m,

3H), 7.40–7.47 (m, 3H), 7.28–7.36 (m, 2H), 7.10 (d, J=1.2 Hz, 1H), 3.26 (m, 2H, NCH$_2$), 2.46–2.55 (m, 6H, 3×NCH$_2$), 2.44 (s, 3H, CH$_3$), 2.41 (s, 3H, CH$_3$), 0.97 (t, J=7.2 Hz, 6H, 2×NCH$_2$CH$_3$).

MS-EI m/z 456 [M$^+$].

Example 28

Synthesis of 2,4-dimethyl-5-(2-oxo-6-phenyl-1,2-dihydroindol-3-ylidenemethyl)-1H-pyrrole-3-carboxylic acid (2-pyrrolidin-1-ylethyl)amide 6-Phenyl-1,3-dihydroindol-2-one (30 mg, 0.15 mmol) was condensed with 5-formyl-2,4-dimethyl-1H-pyrrole-3-carboxylic acid (2-pyrrolidin-1-ylethyl)amide (40 mg) to give 5.9 mg (8.5%) of the title compound as a yellow-orange solid.

$^1$HNMR (300 MHz, DMSO-d6) δ 13.60 (s, br, 1H, NH), 10.99 (, br, 1H, NH), 7.86 (d, J=7.8 Hz, 1H), 7.63–7.66 (m, 3H), 7.51 (m, 1H, CONHCH$_2$), 7.45 (m, 2H), 7.28–7.36 (m, 2H), 7.10 (d, J=1.5 Hz, 1H), 3.31 (m, 6H, 3×NCH$_2$), 2.55 (t, J=6.6 Hz, 2H, NCH$_2$), 2.43 (s, 3H, CH$_3$), 2.40 (s, 3H, CH$_3$), 1.67 (m, 4H, 2×CH$_2$).

MS-EI m/z 454 [M$^+$].

Example 29

Synthesis of 2,4-dimethyl-5-(2-oxo-6-phenyl-1,2-dihydroindol-3-ylidenemethyl)-1H-pyrrole-3-carboxylic acid (3-imidazol-1-ylpropyl)amide 6-Phenyl-1,3-dihydroindol-2-one (8 mg, 0.04 mmol) was condensed with 5-formyl-2,4-dimethyl-1H-pyrrole-3-carboxylic acid (3-imidazol-1-ylpropyl)amide (10 mg) to give 7.3 mg (43%) of the title compound as an orange solid.

$^1$HNMR (300 MHz, DMSO-d6) δ 13.62 (s, br, 1H, NH), 10.99 (, br, 1H, NH), 7.86 (d, J=8.2 Hz, 1H), 7.62–7.70 (m, 5H), 7.45 (m, 2H), 7.35 (m, 1H), 7.30 (dd, J=1.4 & 8.2 Hz, 1H), 7.21 (s, 1H), 7.10 (d, J=1.4 Hz, 1H), 6.89 (s, 1H), 4.02 (t, J=6.9 Hz, 2H, CH$_2$), 3.19 (m, 2H, NCH$_2$ CH$_2$), 2.43 (s, 3H, CH$_3$), 2.41 (s, 3H, CH$_3$), 1.93 (t, J=6.9 Hz, 2H, NCH$_2$).

MS-EI m/z 465 [M$^+$].

Example 30

Synthesis of 5-[6-(3,5-Dichlorophenyl)-2-oxo-1,2-dihydroindol-3-ylidenemethyl]-2,4-dimethyl-1H-pyrrole-3-carboxylic acid (2-diethylaminoethyl)amide 6-(3,5-Dichlorophenyl)-1,3-dihydroindol-2-one (64 mg, 0.23 mmol) was condensed with 5-formyl-2,4-dimethyl-1H-pyrrole-3-carboxylic acid (2-diethylaminoethyl)amide (60 mg) to give 53 mg (44%) of the title compound as a light brown solid.

$^1$HNMR (360 MHz, DMSO-d6) δ 13.62 (s, br, 1H, NH), 10.99 (s, 1H, NH), 7.89 (d, J=7.9 Hz, 1H, H-4), 7.69–7.71 (m, 3H), 7.55 (m, 1H, CONHCH$_2$), 7.37 (m, 2H), 7.14 (d, J=1.4 Hz, 1H, H-7), 3.27 (m, 2H, NCH$_2$), 2.48–2.58 (m, 6H, 3×NCH$_2$), 2.45 (s, 3H, CH$_3$), 2.42 (s, 3H, CH$_3$), 0.97 (t, J=6.8 Hz, 6H, 3×NCH$_2$CH$_3$).

MS m/z 526.9 [M$^+$+1].

Example 31

Synthesis of 2,4-dimethyl-5-(2-oxo-6-pyridin-3-yl-1,2-dihydroindol-3-ylidenemethyl)-1H-pyrrole-3-carboxylic acid (2-diethylaminoethyl)amide 6-Pyridin-3-yl-1,3-dihydroindol-2-one (40 mg, 0.19 mmol) was condensed with 5-formyl-2,4-dimethyl-1H-pyrrole-3-carboxylic acid (2-diethylaminoethyl)amide (50 mg) give 29 mg (33%) of the title compound as a light orange solid.

$^1$HNMR (300 MHz, DMSO-d6) δ 13.62 (s, br, 1H, NH), 11.05 (s, br, 1H, NH), 8.86 (s, br, 1H), 8.53 (d, J=5.8 Hz, 1H), 8.04 (m, 1H), 7.91 (d, J=8.1 Hz, 1H), 7.70 (s, 1H, H-vinyl), 7.40–7.48 (m, 2H), 7.35 (d, J=7.5 Hz, 1H), 7.14 (s, 1H), 3.26 (m, 2H, NCH$_2$), 2.48–2.55 (m, 3×NCH$_2$), 2.42 (s, 3H, CH$_3$), 2.38 (s, 3H, CH$_3$), 0.96 (t, J=6.9 Hz, 6H, 2×NCH$_2$CH$_3$).

MS-EI m/z 457 [M$^+$].

Example 32

Synthesis of 2,4-dimethyl-5-(2-oxo-6-pyridin-3-yl-1,2-dihydroindol-3-ylidenemethyl)-1H-pyrrole-3-carboxylic acid (2-pyrrolidin-1-ylethyl)amide 6-Pyridin-3-yl-1,3-dihydroindol-2-one (60 mg, 0.28 mmol) was condensed with 5-formyl-2,4-dimethyl-1H-pyrrole-3-carboxylic acid (2-pyrrolidin-1-ylethyl)amide (75 mg) to give 90 mg (71%) of the title compound as a light orange solid.

$^1$HNMR (300 MHz, DMSO-d6) δ 13.61 (s, br, 1H, NH), 11.05 (s, br, 1H, NH), 8.86 (d, J=1.5 Hz, 1H), 8.54 (dd, J=1.5 & 4.8 Hz, 1H), 8.05 (m, 1H), 7.91 (d, J=7.8 Hz, 1H), 7.70 (s, 1H, H-vinyl), 7.44–7.53 (m, 2H), 7.36 (dd, J=1.5 & 8.1 Hz, 1H), 7.15 (d, J=1.2 Hz, 1H), 3.33 (m, 2H, NCH$_2$), 2.47–2.57 (m, 6H, 3×NCH$_2$), 2.43 (s, 3H, CH$_3$), 2.41 (s, 3H, CH$_3$), 1.67 (m, 4H, 2×CH$_2$).

MS-EI m/z 455 [M$^+$].

Example 33

Synthesis of 2,4-dimethyl-5-(2-oxo-6-pyridin-3-yl-1,2-dihydroindol-3-ylidenemethyl)-1H-pyrrole-3-carboxylic acid (3-dimethylaminopropyl)amide 6-Pyridin-3-yl-1,3-dihydroindol-2-one (42 mg, 0.2 mmol) was condensed with 5-formyl-2,4-dimethyl-1H-pyrrole-3-carboxylic acid (3-dimethylaminopropyl)amide (50 mg) to give 67 mg (75%) of the title compound as yellow-brown solid.

$^1$HNMR (360 MHz, DMSO-d6) δ 13.61 (s, br, 1H, NH), 11.00 (s, br, 1H, NH), 8.86 (s, br, 1H), 8.54 (s, br, 1H), 8.04 (m, 1H), 7.90 (d, J=8.0 Hz, 1H), 7.69 (s, 1H, H-vinyl), 7.63 (m, 1H), 7.45–7.48 (m, 1H), 7.35 (dd, J=1.7 & 8.0 Hz, 1H), 7.15 (d, J=1.7 Hz, 1H), 3.21–3.27 (m, 2H, NCH$_2$), 2.43 (s, 3H, CH$_3$), 2.41 (s, 3H, CH$_3$), 2.28 (m, 2H, NCH$_2$), 2.14 (s, 6H, 2×NCH$_3$), 1.64 (m, 2H, CH$_2$).

MS-EI m/z 443 [M$^+$].

Example 34

Synthesis of 2,4-dimethyl-5-(2-oxo-5-phenyl-1,2-dihydroindol-3-ylidenemethyl)-1H-pyrrole-3-carboxylic acid (3-dimethylaminopropyl)amide 5-Phenyl-1,3-dihydroindol-2-one (67 mg, 0.32 mmol) was condensed with 5-formyl-2,4-dimethyl-1H-pyrrole-3-carboxylic acid (3-dimethylaminopropyl)amide (81 mg) to give 40 mg (28%) of the title compound as an orange solid.
$^1$HNMR (360 MHz, DMSO-d6) δ 13.66 (s, br, 1H, NH), 10.92 (s, br, 1H, NH), 8.14 (s, 1H), 7.79 (s, 1H), 7.71 (m, 2H), 7.62 (m, 1H), 7.44 (m, 3H), 7.32 (m, 1H), 6.95 (m, 1H), 3.33 (m, 2H, NCH$_2$), 2.43 (s, 6H, 2×CH$_3$), 2.27 (m, 2H, NCH$_2$), 2.13 (s, 6H, 2×NCH$_3$), 1.63 (m, 2H, CH$_2$).
MS-EI m/z 442 [M$^+$].

Example 35

Synthesis of 2,4-dimethyl-5-(2-oxo-5-phenyl-1,2-dihydroindol-3-ylidenemethyl)-1H-pyrrole-3-carboxylic acid (3-diethylamino-propyl)amide 5-Phenyl-1,3-dihydroindol-2-one (1.5 g, 7.16 mmol) was condensed with 5-formyl-2,4-dimethyl-1H-pyrrole-3-carboxylic acid (3-diethylaminopropyl)amide (2 g) to give 1.3 g (40%) of the title compound as a yellow-orange solid.
$^1$HNMR (360 MHz, DMSO-d6) δ 13.64 (s, 1H, NH), 10.91 (s, 1H, NH), 8.14 (d, J=1.4 Hz, 1H, ArH), 7.8 (s, 1H, ArH), 7.7 (dd, J=1.2 and 8.5 Hz, 2H, ArH), 7.6 (t, J=5.3 Hz, 1H, CONHCH$_2$), 7.4 (m, 3H, ArH), 7.3 (t, J=7.4 Hz, 1H, ArH), 6.9 (d, J=8.0 Hz, 1H, ArH), 3.2 (m, 2H, CONHC$\underline{H}_2$), 2.5 (m, 12H, 3×NC$\underline{H}_2$ and 2×C$\underline{H}_3$), 1.61 (m, 2H, CH$_2$C$\underline{H}_2$CH$_2$), 0.93 (t, J=6.7 Hz, 6H, NCH$_2$C$\underline{H}_3$).
MS-EI m/z 470 [M$^+$].

Example 36

Synthesis of 2,4-dimethyl-5-(2-oxo-6-phenyl-1,2-dihydroindol-3-ylidenemethyl)-1H-pyrrole-3-carboxylic acid (3-diethylaminopropyl)amide 6-Phenyl-1,3-dihydroindol-2-one (1.5 g, 7.16 mmol) was condensed with 5-formyl-2,4-dimethyl-1H-pyrrole-3-carboxylic acid (3-diethylaminopropyl)amide (2 g) to give 1.9 g (57%) of the title compound as an orange solid.
$^1$HNMR (360 MHz, DMSO-d6) δ 13.58 (s, 1H, NH), 10.94 (s, 1H, NH), 7.8 (d, J=7.9 Hz, 1H, ArH), 7.6 (m, 4H, ArH), 7.4 (t, J=7.5 Hz, 2H, ArH), 7.3 (m, 2H), 7.1 (d, J=1.4 Hz, 1H, ArH), 3.2 (m, 2H, CONHCH$_2$), 2.5 (m, 12H, 3×NCH$_2$ and 2×CH$_3$), 1.61 (m, 2H, CH$_2$CH$_2$CH$_2$), 0.93 (t, J=6.7 Hz, 6H, NCH$_2$CH$_3$).
MS-EI m/z 470 [M$^+$].

Example 37

Synthesis of 3-[4-(3-Diethylaminopropylcarbamoyl)-3,5-dimethyl-1H-pyrrol-2-ylmethylene]-2-oxo-2,3-dihydro-1H-indole-4-carboxylic acid (3-chloro-4-methoxyphenyl)amide 2-Oxo-2,3-dihydro-1H-indole-4-carboxylic acid (3-chloro-4-methoxyphenyl)amide (1 g, 3.16 mmol) was condensed with 5-formyl-2,4-dimethyl-1H-pyrrole-3-carboxylic acid (3-diethylaminopropyl)amide (1 g, 3.58 mmol) to give 1.7 g (85%) of the title compound as a yellow-orange solid.
MS-EI m/z 578.2 [M$^+$].

Example 38

Synthesis of 5-(5-Bromo-2-oxo-1,2-dihydroindol-3-ylidenemethyl)-2,4-dimethyl-1H-pyrrole-3-carboxylic acid (3-diethylamino-propyl)amide 5-Bromo-1,3-dihydroindol-2-one (0.5 g, 2.36 mmol) was condensed with 5-formyl-2,4-dimethyl-1H-pyrrole-3-carboxylic acid (3-diethylaminopropyl)amide (0.51 g) to give 0.84 g of the title compound as a red-orange solid.
$^1$HNMR (360 MHz, DMSO-d6) δ 13.61 (s, 1H, NH), 10.99 (s, 1H, NH), 8.09 (d, J=1.8 Hz, 1H, ArH), 7.7 (m, 4H), 7.2 (dd, J=1.8 and 8.3 Hz, 2H, ArH), 6.8 (d, J=7.8 Hz, 1H, ArH), 3.3 (br s, 4H, 2×NCH$_2$), 3.2 (m, 2H, CONHCH$_2$), 2.6 (br s, 2H, NCH$_2$and 2×CH$_3$), 2.4 (s, 6H, 2×CH$_3$), 1.66 (m, 2H, CH$_2$CH$_2$CH$_2$), 0.98 (t, J=7.1 Hz, 6H, NCH$_2$CH$_3$).
MS-EI m/z 472 and 474 [M$^+$−1 and M$^+$+1].

Example 39

Synthesis of 5-(5-Bromo-2-oxo-1,2-dihydroindol-3-ylidenemethyl)-2,4-diisopropyl-1H-pyrrole-3-carboxylic acid (2-diethylamino-ethyl)amide 5-Bromo-1,3-dihydroindol-2-one (100 mg, 0.47 mmol) was condensed with 5-formyl-2,4-diisopropyl-1H-pyrrole-3-carboxylic acid (2-diethylaminoethyl)amide (150 mg) to give 0.15 g (62%) of the title compound as a yellow-orange solid.
$^1$HNMR (300 MHz, DMSO-d6) δ 13.97 (s, 1H, NH), 10.95 (s, 1H, NH), 8.09 (d, J=1.3 Hz, 1H, ArH), 7.84 (m, 1H), 7.79 (s, 1H), 7.23 (dd, J=1.3 and 8.1 Hz, 1H, ArH), 6.8 (d, J=8.1 Hz, 1H, ArH), 3.5 (m, 1H, CH), 3.3 (m, 3H, CH and NHCH$_2$), 2.5 (br m, 6H, 3×NCH$_2$), 1.28 (d, J=6.9 Hz, 6H, 2×CH$_3$), 1.23 (d, J=6.6 Hz, 6H, 2×CH$_3$), 0.96 (m, 6H, 2×CH$_2$CH$_3$).
MS-EI m/z 514 and 516 [M$^+$−1 and M$^+$+1].

Example 40

Synthesis of 5-(5-Bromo-2-oxo-1,2-dihydroindol-3-ylidenemethyl)-2,4-diisopropyl-1H-pyrrole-3-carboxylic acid (3-diethylamino-propyl)amide 5-Bromo-1,3-dihydroindol-2-one (90 mg, 0.42 mmol) was condensed with 5-formyl-2,4-diisopropyl-1H-pyrrole-3-carboxylic acid (3-diethylaminopropyl)amide (140 mg) to give 54 mg (25%) of the title compound as red-brown solid.
$^1$HNMR (300 MHz, DMSO-d6) δ 13.98 (s, 1H, NH), 10.96 (s, 1H, NH), 8.09 (d, J=1.7 Hz, 2H), 7.78 (s, 1H, H-vinyl), 7.23 (dd, J=1.7 and 8.1 Hz, 1H, ArH), 6.82 (d, J=8.1 Hz, 1H, ArH), 3.5 (m, 1H, CH), 3.25 (m, 2H, NHCH$_2$), 3.15 (m, 1H, CH), 2.7 (br s, 6H, 3×NCH$_2$), 1.7 (br m, 2H, CH$_2$CH$_2$CH$_2$), 1.28 (d, J=6.9 Hz, 6H, 2×CH$_3$), 1.24 (d, J=5.9 Hz, 6H, 2×CH$_3$), 1.06 (m, 6H, 2×CH$_2$CH$_3$).
MS-EI m/z 528 and 530 [M$^+$−1 and M$^+$+1].

Example 41

Synthesis of 5-(5-Bromo-2-oxo-1,2-dihydroindol-3-ylidenemethyl)-2,4-diisopropyl-1H-pyrrole-3-carboxylic acid (3-pyrrolidin-1-ylpropyl)amide 5-Bromo-1,3-dihydroindol-2-one (130 mg, 0.6 mmol) was condensed with 5-formyl-2,4-diisopropyl-1H-pyrrole- 3-carboxylic acid (3-pyrrolidin-1-ylpropyl)amide (150 mg, 0.45 mmol) to give 36 mg (15%) of the title compound as a tan-orange solid.

$^1$HNMR (300 MHz, DMSO-d6) δ 13.98 (s, 1H, NH), 10.97 (s, 1H, NH), 8.10 (d, J=1.6 Hz, 2H), 7.78 (s, 1H, H-vinyl), 7.23 (dd, J=1.6 and 7.6 Hz, 1H, ArH), 6.82 (d, J=7.6 Hz, 1H, ArH), 3.5 (m, 1H, CH), 3.25 (m, 2H, NHCH$_2$), 3.15 (m, 1H, CH), 2.7 (br s, 6H, 3×NCH$_2$), 1.7 (br m, 6H, 3×NCH$_2$CH$_2$), 1.28 (d, J=5.6 Hz, 6H, 2×CH$_3$), 1.24 (d, J=5.7 Hz, 6H, 2×CH$_3$).

MS-EI m/z 526 and 528 [M$^+$−1 and M$^+$+1].

Example 42

Synthesis of 5-(5-Bromo-2-oxo-1,2-dihydroindol-3-ylidenemethyl)-2,4-dimethyl-1H-pyrrole-3-carboxylic acid (pyridin-4-ylmethyl)-amide 5-Bromo-1,3-dihydroindol-2-one (170 mg, 0.8 mmol) was condensed with 5-formyl-2,4-dimethyl-1H-pyrrole-3-carboxylic acid (pyridin-4-ylmethyl)amide (200 mg) to give 14 mg (4%) of the title compound as a yellow solid.

$^1$HNMR (300 MHz, DMSO-d6) δ 13.67 (s, 1H, NH), 11.01 (s, br, 1H, NH), 8.51 (dd, J=1.6 & 4.3 Hz, 2H), 8.23 (t, J=6.0 Hz, 1H, CONHCH$_2$), 8.11 (d, J=1.9 Hz, 1H), 7.78 (s, 1H, H-vinyl), 7.31 (d, J=6.0 Hz, 2H), 7.25 (dd, J=1.9 & 8.1 Hz, 1H), 6.82 (d, J=8.1 Hz, 1H), 4.45 (d, J=6.0 Hz, 2H, NCH$_2$), 2.46 (s, 6H, 2×CH$_3$).

MS-EI m/z 450 and 452 [M$^+$−1 and M$^+$+1].

Example 43

Synthesis of 5-[6-(4-Butylphenyl)-2-oxo-1,2-dihydroindol-3-ylidenemethyl]-2,4-dimethyl-1H-pyrrole-3-carboxylic acid (2-pyrrolidin-1-ylethyl)amide 5-[6-(4-Butylphenyl)]-1,3-dihydroindol-2-one (50 mg, 0.19 mmol) was condensed with 5-formyl-2,4-dimethyl-1H-pyrrole-3-carboxylic acid (2-pyrrolidin-1-ylethyl)amide (50 mg) to give 74 mg (76%) of the title compound as an orange solid.

$^1$HNMR (360 MHz, DMSO-d6) δ 13.58 (s, 1H, NH), 10.93 (s, br, 1H, NH), 7.82 (d, J=7.9 Hz, 1H), 7.63 (s, 1H, H-vinyl), 7.54 (d, J=7.9 Hz, 2H), 7.46 (m, 1H, CONH), 7.26 (m, 3H), 7.09 (s, 1H), 3.30 (m, 2H, CH$_2$), 2.52–2.63 (m, 4H, 2×CH$_2$), 2.49 (m, 4H, 2×CH$_2$), 2.43 (s, 3H, CH$_3$), 2.40 (s, 3H, CH$_3$), 1.68 (m, 4H, 2×CH$_2$), 1.58 (m, 2H, CH$_2$), 1.34 (m, 2H, CH$_2$), 0.91 (t, J=7.2 Hz, 3H, CH$_2$CH$_3$).

MS-EI m/z 510 [M$^+$].

Example 44

Synthesis of 5-[6-(5-Isopropyl-2-methoxyphenyl)-2-oxo-1,2-dihydroindol-3-ylidenemethyl]-2,4-dimethyl-1H-pyrrole-3-carboxylic acid (2-pyrrolidin-1-ylethyl)amide 6-(5-Isopropyl-2-methoxyphenyl)-1,3-dihydroindol-2-one (50 mg, 0.17 mmol) was condensed with 5-formyl-2,4-dimethyl-1H-pyrrole-3-carboxylic acid (2-pyrrolidin-1-ylethyl)amide (45 mg) to give 67 mg (75%) of the title compound as an orange solid.

$^1$HNMR (360 MHz, DMSO-d6) δ 13.60 (s, 1H, NH), 10.82 (s, br, 1H, NH), 7.77 (d, J=7.9 Hz, 1H), 7.61 (s, 1H, H-vinyl), 7.45 (m, 1H, CONH), 7.0–7.19 (m, 5H), 3.73 (s, 3H, OCH$_3$), 3.32 (m, 2H, CH$_2$), 2.87 (m, 1H, CH(CH$_3$)$_2$), 2.56 (m, 2H, CH$_2$), 2.48 (m, 4H, 2×CH$_2$), 2.43 (s, 3H, CH$_3$), 2.40 (s, 3H, CH$_3$), 1.68 (m, 4H, 2×CH$_2$), 1.21 (d, J=6.8 Hz, 6H, CH(CH$_3$)$_2$).

MS m/z 527.2 [M$^+$+1].

Example 45

Synthesis of 5-[6-(4-Ethylphenyl)-2-oxo-1,2-dihydroindol-3-ylidenemethyl]-2,4-dimethyl-1H-pyrrole-3-carboxylic acid (2-pyrrolidin-1-ylethyl)amide 6-(4-Ethylphenyl)-1,3-dihydroindol-2-one (45 mg, 0.19 mmol) was condensed 5-formyl-2,4-dimethyl-1H-pyrrole-3-carboxylic acid (2-pyrrolidin-1-ylethyl)amide (50 mg) to give 60 mg (65%) of the title compound as a yellow-orange solid.

$^1$HNMR (300 MHz, DMSO-d6) δ 13.59 (s, 1H, NH), 10.96 (s, br, 1H, NH), 7.83 (d, J=8.4 Hz, 1H), 7.64 (s, 1H, H-vinyl), 7.51–7.56 (m, 3H), 7.25–7.30 (m, 3H), 7.08 (d, J=1 Hz, 1H), 3.31 (m, 2H, CH$_2$), 2.63 (m, 2H, CH$_2$CH$_3$), 2.55 (m, 2H, CH$_2$), 2.49 (m, 4H, 2×CH$_2$), 2.42 (s, 3H, CH$_3$), 2.40 (s, 3H, CH$_3$), 1.67 (m, 4H, 2×CH$_2$), 1.20 (t, J=7.5 Hz, 3H, CH$_2$CH$_3$).

MS-EI m/z 482 [M$^+$].

Example 46

Synthesis of 5-[6-(2,4-Dimethoxyphenyl)-2-oxo-1,2-dihydroindol-3-ylidenemethyl]-2,4-dimethyl-1H-pyrrole-3-carboxylic acid (2-pyrrolidin-1-ylethyl)amide 6-(2,4-Dimethoxyphenyl)-1,3-dihydroindol-2-one (51 mg, 0.19 mmol) was condensed with 5-formyl-2,4-dimethyl-1H-pyrrole-3-carboxylic acid (2-pyrrolidin-1-ylethyl)amide (50 mg) to give 30 mg (31%) of the title compound as an orange solid.

$^1$HNMR (300 MHz, DMSO-d6) δ 13.59 (s, 1H, NH), 10.86 (s, br, 1H, NH), 7.75 (d, J=7.8 Hz, 1H), 7.60 (s, 1H, H-vinyl), 749 (m, 1H, CONH), 7.22 (d, J=8.4 Hz, 1H), 7.03 (m, 1H), 6.97 (s, 1H), 6.58–6.65 (m, 2H), 3.79 (s, 3H, OCH$_3$), 3.76 (s, 3H, OCH$_3$), 3.33 (m, 2H, CH$_2$), 2.55 (m, 2H, CH$_2$), 2.50 (m, 4H, 2×CH$_2$), 2.42 (s, 3H, CH$_3$), 2.39 (s, 3H, CH$_3$), 1.67 (m, 4H, 2×CH$_2$).

MS-EI m/z 514 [M$^+$].

Example 47

Synthesis of 5-[6-(3-Isopropylphenyl)-2-oxo-1,2-dihydroindol-3-ylidenemethyl]-2,4-dimethyl-1H-pyrrole-3-carboxylic acid (2-pyrrolidin-1-ylethyl)amide 6-(3-Isopropylphenyl)-1,3-dihydroindol-2-one (48 mg, 0.19 mmol) was condensed with 5-formyl-2,4-dimethyl-1H-pyrrole-3-carboxylic acid (2-pyrrolidin-1-ylethyl)amide (50 mg) to give 59 mg (63%) of the title compound as an orange solid.

$^1$HNMR (300 MHz, DMSO-d6) δ 13.63 (s, 1H, NH), 10.97 (s, br, 1H, NH), 7.87 (d, J=7.8 Hz, 1H), 7.68 (s, 1H, H-vinyl), 7.24–7.55 (m, 6H), 7.13 (s, 1H), 3.34 (m, 2H, CH$_2$), 3.30 (m, 1H, CH(CH$_3$)$_2$), 2.60 (m, 2H, CH$_2$), 2.50 (m, 4H, 2×CH$_2$), 2.45 (s, 3H, CH$_3$), 2.43 (s, 3H, CH$_3$), 1.70 (m, 4H, 2×CH$_2$), 1.27 (d, J=6.9 Hz, 6H, CH(CH$_3$)$_2$).

MS-EI m/z 496 [M$^+$].

Example 48

Synthesis of 5-(5-Fluoro-2-oxo-1,2-dihydroindol-3-ylidenemethyl)-2,4-dimethyl-1H-pyrrole-3-carboxylic acid (2-diethylamino-ethyl)amide 5-Fluoro-1,3-dihydroindol-2-one (0.54 g, 3.8 mmol) was condensed with 5-formyl-2,4-dimethyl-1H-pyrrole-3-carboxylic acid (2-diethylaminoethyl)amide to give 0.83 g (55%) of the title compound as a yellow green solid.
$^1$HNMR (360 MHz, DMSO-d6) δ 13.66 (s, 1H, NH), 10.83 (s, br, 1H, NH), 7.73 (dd, J=2.5 & 9.4 Hz, 1H), 7.69 (s, 1H, H-vinyl), 7.37 (t, 1H, CONHCH$_2$CH$_2$), 6.91 (m, 1H), 6.81–6.85 (m, 1H), 3.27 (m, 2H, CH$_2$), 2.51 (m, 6H, 3×CH$_2$), 2.43 (s, 3H, CH$_3$), 2.41 (s, 3H, CH$_3$), 0.96 (t, J=6.9 Hz, 6H, N(CH$_2$CH$_3$)$_2$).
MS-EI m/z 398 [M$^+$].

Example 49 (Alternative Synthesis)

Synthesis of 5-[5-Fluoro-2-oxo-1,2-dihydro-indol-(3Z)-ylidenemethyl]-2,4-dimethyl-1H-pyrrole-3-carboxylic acid (2-diethylamino-ethyl)-amide Hydrazine hydrate (55%, 3000 mL) and 5-fluoroisatin (300 g) were heated to 100° C. An additional 5-fluoro-isatin (500 g) was added in portions (100 g) over 120 minutes with stirring. The mixture was heated to 110° C. and stirred for 4 hours. The mixture was cooled to room temperature and the solids collected by vacuum filtration to give crude (2-amino-5-fluoro-phenyl)-acetic acid hydrazide (748 g). The hydrazide was suspended in water (700 mL) and the pH of the mixture adjusted to <pH 3 with 12 N hydrochloric acid. The mixture was stirred for 12 hours at room temperature. The solids were collected by vacuum filtration and washed twice with water. The product was dried under vacuum to give 5-fluoro-1,3-dihydro-indol-2-one (600 g, 73% yield) as a brown powder.
$^1$H-NMR (dimethylsulfoxide-d$_6$) δ 3.46 (s, 2H, CH$_2$), 6.75, 6.95, 7.05 (3×m, 3H, aromatic), 10.35 (s, 1H, NH). MS m/z 152 [M+1].

3,5-Dimethyl-1H-pyrrole-2,4-dicarboxylic acid 2-tert-butyl ester 4-ethyl ester (2600 g) and ethanol (7800 mL) were stirred vigorously while 10 N hydrochloric acid (3650 mL) was slowly added. The temperature increased from 25° C. to 35° C. and gas evolution began. The mixture was warmed to 54° C. and stirred with further heating for one hour at which time the temperature was 67° C. The mixture was cooled to 5° C. and 32 L of ice and water were slowly added with stirring. The solid was collected by vacuum filtration and washed three times with water. The solid was air dried to constant weight to give of 2,4-dimethyl-1H-pyrrole-3-carboxylic acid ethyl ester (1418 g, 87% yield) as a pinkish solid. $^1$H-NMR (dimethylsulfoxide-d$_6$) δ 2.10, 2.35 (2×s, 2×3H, 2×CH$_3$), 4.13 (q, 2H, CH$_2$), 6.37 (s, 1H, CH), 10.85 (s, 1H, NH). MS m/z 167 [M+1].

Dimethylformamide (322 g) and dichloromethane (3700 mL) were cooled in an ice bath to 4° C. and phosphorus oxychloride (684 g) was added with stirring. Solid 2,4-dimethyl-1H-pyrrole-3-carboxylic acid ethyl ester (670 g) was slowly added in aliquots over 15 minutes. The maximum temperature reached was 18° C. The mixture was heated to reflux for one hour, cooled to 10° C. in an ice bath and 1.6 L of ice water was rapidly added with vigorous stirring. The temperature increased to 15° C. 10 N Hydrochloric acid (1.6 L) was added with vigorous stirring. The temperature increased to 22° C. The mixture was allowed to stand for 30 minutes and the layers allowed to separate. The temperature reached a maximum of 40° C. The aqueous layer was adjusted to pH 12–13 with 10 N potassium hydroxide (3.8 L) at a rate that allowed the temperature to reach and remain at 55° C. during the addition. After the addition was complete the mixture was cooled to 10° C. and stirred for 1 hour. The solid was collected by vacuum filtration and washed four times with water to give 5-formyl-2,4-dimethyl-1H-pyrrole-3-carboxylic acid ethyl ester (778 g, 100% yield) as a yellow solid. $^1$H-NMR (DMSO-d$_6$) δ 1.25 (t, 3H, CH$_3$), 2.44, 2.48 (2×s, 2×3H, 2×CH$_3$), 4.16 (q, 2H, CH$_2$), 9.59 (s, 1H, CHO), 12.15 (br s, 1H, NH). MS m/z 195 [M+1].

5-Formyl-2,4-dimethyl-1H-pyrrole-3-carboxylic acid ethyl ester (806 g), potassium hydroxide (548 g), water (2400 mL) and methanol (300 mL) were refluxed for two hours with stirring and then cooled to 8° C. The mixture was extracted twice with dichloromethane. The aqueous layer was adjusted to pH 4 with 1000 mL of 10 N hydrochloric acid keeping the temperature under 15° C. Water was added to facilitate stirring. The solid was collected by vacuum filtration, washed three times with water and dried under vacuum at 50° C. to give 5-formyl-2,4-dimethyl-1H-pyrrole-3-carboxylic (645 g, 93.5% yield) acid as a yellow solid. NMR (DMSO-d$_6$) δ 2.40, 2.43 (2×s, 2×3H, 2×CH$_3$), 9.57 (s, 1H, CHO), 12.07 (br s, 2H, NH+COOH). MS m/z 168 [M+1].

5-Formyl-2,4-dimethyl-1H-pyrrole-3-carboxylic acid (1204 g) and 6020 mL of dimethylformamide were stirred at room temperature while 1-(3-dimethyl-aminopropyl-3-ethylcarbodiimide hydrochloride (2071 g), hydroxybenzotriazole (1460 g), triethylamine (2016 mL) and diethylethylenediamine (1215 mL) were added. The mixture was stirred for 20 hours at room temperature. The mixture was diluted with 3000 mL of water, 2000 mL of brine and 3000 mL of saturated sodium bicarbonate solution and the pH adjusted to greater than 10 with 10 N sodium hydroxide. The mixture was extracted twice with 5000 mL each time of 10% methanol in dichloromethane and the extracts combined, dried over anhydrous magnesium sulfate and rotary evaporated to dryness. The mixture was with diluted with 1950 mL of toluene and rotary evaporated again to dryness. The residue was triturated with 3:1 hexane:diethyl ether (4000 mL). The solids were collected by vacuum filtration, washed twice with 400 mL of ethyl acetate and dried under vacuum at 34° C. for 21 hours to give 5-formyl-2,4-dimethyl-1H-pyrrole-3-carboxylic acid (2-diethylamino-ethyl)-amide (819 g, 43% yield) as a light brown solid. $^1$H-NMR (dimethylsulfoxide-d$_6$) δ 0.96 (t, 6H, 2×CH$_3$), 2.31, 2.38 (2×s, 2×CH$_3$), 2.51 (m, 6H 3×CH$_2$), 3.28 (m, 2H, CH$_2$), 7.34 (m, 1H, amide NH), 9.56 (s, 1H, CHO), 11.86 (s, 1H, pyrrole NH). MS m/z 266 [M+1].

5-Formyl-2,4-dimethyl-1H-pyrrole-3-carboxylic acid (2-diethylaminoethyl)-amide (809 g), 5-fluoro-1,3-dihydro-indol-2-one (438 g), ethanol (8000 mL) and pyrrolidine (13 mL) were heated at 78° C. for 3 hours. The mixture was cooled to room temperature and the solids collected by vacuum filtration and washed with ethanol. The solids were stirred with ethanol (5900 mL) at 72° C. for 30 minutes. The mixture was cooled to room temperature. The solids were collected by vacuum filtration, washed with ethanol and dried under vacuum at 54° C. for 130 hours to give 5-[5-fluoro-2-oxo-1,2-dihydro-indol-(3Z)-ylidenemethyl]-2,4-dimethyl-1H-pyrrole-3-carboxylic acid (2-diethylamino-ethyl)-amide (1013 g, 88% yield) as an orange solid. $^1$H-NMR (dimethylsulfoxide-d$_6$) δ 0.98 (t, 6H, 2×CH$_3$), 2.43, 2.44 (2×s, 6H, 2×CH$_3$), 2.50 (m, 6H, 3×CH$_2$), 3.28 (q, 2H, CH$_2$), 6.84, 6.92, 7.42, 7.71, 7.50 (5×m, 5H, aromatic, vinyl, CONH), 10.88 (s, 1H, CONH), 13.68 (s, 1H, pyrrole NH). MS m/z 397 [M−1].

Example 50

Synthesis of 3-[4-(2-Diethylaminoethylcarbamoyl)-3,5-dimethyl-1H-pyrrol-2-ylmethylene]-2-oxo-2,3-dihydro-1H-indole-6-carboxylic acid 2-Oxo-2,3-dihydro-1H-indole-6-carboxylic acid (80 mg, 0.45 mmol) was condensed with 5-formyl-2,4-dimethyl-1H-pyrrole-3-carboxylic acid (2-diethylaminoethyl)amide to give 210 mg (92%) of the title compound as a yellow orange solid.

$^1$HNMR (360 MHz, DMSO-d6) δ 13.6 (s, 1H, NH), 7.76 (d, J=8.0 Hz, 1H), 7.66 (s, 1H, H-vinyl), 7.57 (dd, J=1.5 & 8.0 Hz, 1H), 7.40–7.42 (m, 2H), 3.28 (m, 2H, CH$_2$), 2.88 (m, H-piperidine), 2.54 (m, 6H, 3×CH$_2$), 2.44 (s, 3H, CH$_3$), 2.40 (s, 3H, CH$_3$), 1.56 (m, H-piperidine), 0.97 (t, J=6.98 Hz, 6H, N(CH$_2$CH$_3$)$_2$).

MS m/z 424 [M$^+$].

Example 51

Synthesis of 5-(5-dimethylsulfamoyl-2-oxo-1,2-dihydroindol-3-ylidenemethyl)-2,4-dimethyl-1H-pyrrole-3-carboxylic acid (2-pyrrolidin-1-ylethyl) amide 2-Oxo-2,3-dihydro-1H-indole-5-sulfonic acid dimethylamide (90 mg, 0.38 mmol) was condensed with 5-formyl-2,4-dimethyl-1H-pyrrole-3-carboxylic acid (2-pyrrolidin-1-ylethyl)amide (100 mg) to give 100 mg (54%) of the title compound as a yellow solid.

$^1$HNMR (360 MHz, DMSO-d6) δ 13.65 (s, 1H, NH), 11.30 (s, br, 1H, NH), 8.25 (d, 1H), 7.92 (s, 1H, H-vinyl), 7.48–7.53 (m, 2H), 7.07 (d, J=8.2 Hz, 1H), 3.33 (m, 2H, CH$_2$), 2.61 (s, 6H, N(CH$_3$)$_2$), 2.56 (t, 2H, CH$_2$), 2.49 (m, 4H, 2×CH$_2$), 2.45 (s, 3H, CH$_3$), 2.44 (s, 3H, CH$_3$), 1.67 (m, 4H, 2×CH$_2$).

MS-EI m/z 485 [M$^+$].

Example 52

Synthesis of 5-[5-(3-Chlorophenylsulfamoyl)-2-oxo-1,2-dihydroindol-3-ylidenemethyl]-2,4-dimethyl-1H-pyrrole-3-carboxylic acid (2-pyrrolidin-1-ylethyl) amide 2-Oxo-2,3-dihydro-1H-indole-5-sulfonic acid (3-chlorophenyl)amide (120 mg, 0.38 mmol) was condensed with 5-formyl-2,4-dimethyl-1H-pyrrole-3-carboxylic acid (2-pyrrolidin-1-ylethyl)amide (100 mg) to give 150 mg (69%) of the title compound as a yellow orange solid.

$^1$HNMR (360 MHz, DMSO-d6) δ 13.55 (s, 1H, NH), 11.26 (br s, 1H, NH), 10.30 (br s, 1H, NH), 8.26 (d, 1H), 7.79 (s, 1H, H-vinyl), 7.51–7.57 (m, 2H), 7.22 (t, J=8.1 Hz, 1H), 7.15 (m, 1H), 7.07 (m, 1H), 7.0 (m, 2H), 3.44 (m, 2H, CH$_2$), 2.57 (t, J=7.0 Hz, 2H, CH$_2$), 2.49 (m, 4H, 2×CH$_2$), 2.44 (s, 3H, CH$_3$), 2.43 (s, 3H, CH$_3$), 1.68 (m, 4H, 2×CH$_2$).

MS m/z 568 [M$^+$].

Example 53

Synthesis of 2,4-dimethyl-5-[2-oxo-5-(pyridin-3-ylsulfamoyl)-1,2-dihydroindol-3-ylidenemethyl]-1H-pyrrole-3-carboxylic acid (2-pyrrolidin-1-ylethyl) amide 2-Oxo-2,3-dihydro-1H-indole-5-sulfonic acid pyridin-3-ylamide (110 mg, 0.38 mmol) was condensed with 5-formyl-2,4-dimethyl-1H-pyrrole-3-carboxylic acid (2-pyrrolidin-1-ylethyl)amide (100 mg) to give 150 mg (74%) of the title compound as an orange solid.

$^1$HNMR (360 MHz, DMSO-d6) δ 13.58 (s, 1H, NH), 8.21 (d, J=2.0 Hz, 2H), 8.04 (m, 1H), 7.76 (s, 1H, H-vinyl), 7.49–7.54 (m, 2H), 7.41 (m, 1H), 7.14 (m, 1H), 6.94 (d, J=8.5 Hz, 1H), 3.33 (m, 2H, CH$_2$), 2.56 (t, J=7.06 Hz, 2H, CH$_2$), 2.49 (m, 4H, 2×CH$_2$), 2.43 (s, 6H, 2×CH$_3$), 1.68 (m, 4H, 2×CH$_2$).

MS m/z 535 [M$^+$].

Example 54

Synthesis of 3-[3,5-dimethyl-4-(4-methylpiperazine-1-carbonyl)-1H-pyrrol-2-ylmethylene]-4-(2-hydroxyethyl)-1,3-dihydroindol-2-one 4-(2-Hydroxyethyl)-1,3-dihydroindol-2-one (71 mg, 0.4 mmol) was condensed with 3,5-dimethyl-4-(4-methyl-piperazine-1-carbonyl)-1H-pyrrole-2-carbaldehyde to give 90 mg (55%) of the title compound as an orange solid.

$^1$HNMR (300 MHz, DMSO-d6) δ 14.25(s, 1H, NH), 10.88 (s, 1H, NH), 7.57 (s, 1H, H-vinyl), 7.03 (m, 1H), 6.75–6.82 (m, 2H), 4.86 (m, 1H, OH), 3.70 (m, 2H, CH$_2$), 3.04 (m, 2H, CH$_2$), 2.48 (m, 4H, 2×CH$_2$), 2.28 (br s, 7H), 2.19 (s, 3H, CH$_3$), 2.18 (s, 3H, CH$_3$).

MS m/z (+ve) 4.09.3 [M$^+$].

Example 55

Synthesis of 3-[3,5-dimethyl-4-(4-methylpiperazine-1-carbonyl)-1H-pyrrol-2-ylmethylene]-2-oxo-2,3-dihydro-1H-indole-5-sulfonic acid phenylamide 2-Oxo-2,3-dihydro-1H-indole-5-sulfonic acid phenylamide (110 mg, 0.4 mmol) was condensed with 3,5-dimethyl-4-(4-methylpiperazine-1-carbonyl)-1H-pyrrole-2-carbaldehyde (100 mg) to give 50 mg (24%) of the title compound as a yellow solid.

$^1$HNMR (300 MHz, DMSO-d6) δ 13.52 (s, 1H, NH), 11.26 (s, 1H, NH), 10.08 (s, 1H, NH), 8.21 (d, J=1.6 Hz, 1H), 7.75 (s, 1H, H-vinyl), 7.50 (dd, J=1.6 & 8.3 Hz, 1H), 7.19 (m, 2H), 7.10 (m, 2H), 6.97 (m, 2H), 2.49 (m, 4H, 2×CH$_2$), 2.28 (m, 10H, 2×CH$_3$ & 2×CH$_2$), 2.18 (s, 3H, CH$_3$).

MS-EI m/z 519 [M$^+$].

Example 56

Synthesis of 5-(5-dimethylsulfamoyl-2-oxo-1,2-dihydroindol-3-ylidenemethyl)-2,4-dimethyl-1H-pyrrole-3-carboxylic acid (2-diethylaminoethyl) amide 2-Oxo-2,3-dihydro-1H-indole-5-sulfonic acid dimethylamide (90 mg, 0.38 mmol) was condensed with 5-formyl-2, 4-dimethyl-1H-pyrrole-3-carboxylic acid (2-diethylaminoethyl) amide (100 mg) to give 80 mg (43%) of the title compound as a yellow solid.

$^1$HNMR (300 MHz, DMSO-d6) δ 11.30 (s, 1H, NH), 8.27 (d, J=1.7 Hz, 1H), 7.94 (s, 1H, H-vinyl), 7.49 (dd, J=1.7 & 8.0 Hz, 1H), 7.44 (m, 1H, CONHCH$_2$CH$_2$), 7.07 (d, J=8.0 Hz, 1H), 3.26 (m, 2H, CH$_2$), 2.60 (s, 6H, N(CH$_3$)$_2$), 2.53 (m, 2H, CH$_2$), 2.45–2.50 (m, 10H, 2×CH$_3$ & N(CH$_2$CH$_3$)$_2$), 0.96 (t, J=7.2 Hz, 6H, N(CH$_2$CH$_3$)$_2$).

MS-EI m/z 487 [M$^+$].

Example 57

Synthesis of 5-[5-(3-Chlorophenylsulfamoyl)-2-oxo-1,2-dihydroindol-3-ylidenemethyl]-2,4-dimethyl-1H-pyrrole-3-carboxylic acid (2-diethylaminoethyl) amide 2-Oxo-2,3-dihydro-1H-indole-5-sulfonic acid (3-chlorophenyl)amide (120 mg, 3.8 mmol) was condensed with 5-formyl-2,4-dimethyl-1H-pyrrole-3-carboxylic acid (2-diethylaminoethyl)amide (100 mg) to give 80 mg (37%) of the title compound as a yellow solid.

$^1$HNMR (360 MHz, DMSO-d6) δ 13.55 (s, 1H, NH), 11.24 (s, 1H, NH), 10.29 (s, 1H, NH), 8.25 (d, J=1.87 Hz, 1H), 7.79 (s, 1H, H-vinyl), 7.52 (dd, J=1.87 & 8.3 Hz, 1H), 7.42 (m, 1H, CONHCH$_2$CH$_2$), 7.22 (t, J=8.02 Hz, 1H), 7.15 (t, J=2 Hz, 1H), 7.08 (m, 1H), 7.0 (m, 2H), 3.27 (m, 2H, CH$_2$), 2.48–2.57 (m, 6H, 3×CH$_2$), 2.45 (s, 3H, CH$_3$), 2.44 (s, 3H, CH$_3$), 0.97 (t, J=7.0 Hz, 6H, N(CH$_2$CH$_3$)$_2$).

MS m/z 570.1 [M$^+$].

Example 58

Synthesis of 4-Methyl-5-(5-methylsulfamoyl-2-oxo-1,2-dihydro-indol-3-ylidenemethyl)-1H-pyrrole-3-carboxylic acid $^1$HNMR (300 MHz, DMSO-d6) δ 13.56 (br s, 1H, NH), 8.24 (d, J=1.5 Hz, 1H), 7.86 (s, 1H, H-vinyl), 7.74 (d, J=2.96 Hz, 1H), 7.56 (dd, J=1.5 & 8.1 Hz, 1H), 7.20 (br m, 1H, NHCH$_3$), 7.03 (d, J=8.1 Hz, 1H), 2.57 (s, 3H, CH$_3$), 2.41 (s, 3H, CH$_3$).

MS-EI m/z 361 [M$^+$].

Example 59

Synthesis of {[4-Methyl-5-(4-methyl-5-methylsulfamoyl-2-oxo-1,2-dihydro-indol-3-ylidenemethyl)-1H-pyrrole-3-carbonyl]-amino}-acetic acid ethyl ester 4-Methyl-1H-pyrrole-3-carboxylic acid ethyl ester (lit. ref. D. O. Cheng, T. L. Bowman and E. LeGoff; J. Heterocyclic Chem.; 1976; 13; 1145–1147) was formylated using method A, hydrolysed using method B followed by amidation (method C) to give [(5-formyl-4-methyl-1H-pyrrole-3-carbonyl)-amino]-acetic acid ethyl ester.

4-Methyl-5-methylaminosulfonyl-2-oxindole (50 mg, 0.21 mmol) was condensed with [(5-formyl-4-methyl-1H-pyrrole-3-carbonyl)-amino]-acetic acid ethyl ester (100 mg, 0.42 mmol) and piperidine (0.1 mL) in ethanol (2 mL) to give 50 mg (52%) of the title compound.

$^1$HNMR (360 MHz, DMSO-d6) δ 13.59 (s, 1H, NH), 11.29 (v.br. s, 1H, NH—CO), 8.33 (t, J=5.8 Hz, 1H, CONHCH$_2$), 7.83 (d, J=3.11 Hz, 1H), 7.80 (s, 1H, H-vinyl), 7.71 (d, J=8.5 Hz, 1H), 7.34 (br m, 1H, NHCH$_3$), 6.89 (d, J=8.5 Hz, 1H), 4.11 (q, J=7.1 Hz, 2H, OCH$_2$CH$_3$), 3.92 (d, J=5.8 Hz, 2H, GlyCH$_2$), 2.86 (s, 3H, CH$_3$), 2.48 (s, 3H, CH$_3$), 2.42 (d, J=4.71 Hz, 3H, HNCH$_3$), 1.20 (t, J=7.1 Hz, 3H, OCH$_2$CH$_3$).

MS-EI m/z 460 [M$^+$].

Example 60

Synthesis of {[4-Methyl-5-(5-methylsulfamoyl-2-oxo-1,2-dihydro-indol-3-ylidenemethyl)-1H-pyrrole-3-carbonyl]-amino}-acetic acid ethyl ester A mixture of 5-methylaminosulfonyl-2-oxindole (0.06 g, 0.22 mmol), [(5-formyl-4-methyl-1H-pyrrole-3-carbonyl)-amino]-acetic acid ethyl ester (0.075 g, 0.27 mmol) and piperidine (2 drops) in ethanol (5 mL) was heated in a sealed tube at 90° C. for 12 hrs. After cooling, the precipitate was collected by vacuum filtration, washed with ethanol, triturated with dichloromethane/ether and dried to give 0.035 g (36%) of the title compound as a yellowish brown solid.

$^1$H NMR (360 MHz, DMSO-d6) δ 13.6 (s, 1H, NH), 11 (v.br. s, 1H, NH—CO), 8.30 (t, J=5.7 Hz, 1H, CONHCH$_2$), 8.25 (d, J=1.2 Hz, 1H), 7.88 (s, 1H, H-vinyl), 7.84 (d, J=3.3 Hz, 1H), 7.57 (dd, J=1.9 & 8.5 Hz, 1H), 7.14 (br m, 1H, NHCH$_3$), 7.04 (d, J=8.5 Hz, 1H), 4.11 (q, J=6.7 Hz, 2H, OCH$_2$CH$_3$), 3.92 (d, J=5.7 Hz, 2H, GlyCH$_2$), 2.55 (s, 3H, CH$_3$), 2.41 (m, 3H, NCH$_3$), 1.20 (t, J=6.7 Hz, 3H, OCH$_2$CH$_3$).

MS m/z 446 [M$^+$].

Example 61

Synthesis of {[4-Methyl-5-(5-methylsulfamoyl-2-oxo-1,2-dihydro-indol-3-ylidenemethyl)-1H-pyrrole-3-carbonyl]-amino}-acetic acid A mixture of [(5-formyl-4-methyl-1H-pyrrole-3-carbonyl)-amino]-acetic acid ethyl ester (0.142 g, 0.59 mmol) and 1N NaOH (1.2 mL) in methanol (10 mL) was stirred at room temperature for 1 hr. The reaction was concentrated and the residue was condensed with 5-methylaminosulfonyl-2-oxindole (0.13 g, 0.48 mmol) and piperidine (0.12 mL) in ethanol (12 mL) to give 0.11 g (52%) of the title compound.

$^1$HNMR (300 MHz, DMSO-d6) δ 13.98 (br s, 1H, NH), 8.17 (s, 1H), 7.80 (s, 1H), 7.75 (d, J=3.1 Hz, 1H), 7.51 (dd, J=2 & 8.2 Hz, 1H), 7.21 (m on br s, 2H), 6.97 (d, J=8.1 Hz, 1H), 3.41 (d, J=4.2 Hz, 2H, CH$_2$NH), 2.54 (s, 3H, pyrrole-CH$_3$), 2.39 (s, 3H, ArCH$_3$).

MS m/z 417 [M−1]$^+$.

Example 62

Synthesis of 5-Methyl-2-(2-oxo-1,2-dihydro-indol-3-ylidenemethyl)-1H-pyrrole-3-carboxylic acid $^1$HNMR (300 MHz, DMSO-d6) δ 13.77 (br s, 1H, NH), 12.49 (s, 1H, COOH), 11.07 (s, 1H, NH), 8.39 (s, 1H, H-vinyl), 7.43 (d, J=7.47 Hz, 1H), 7.20 (t, J=7.47 Hz, 1H), 7.03 (t, J=7.47 Hz, 1H), 6.91 (d, J=7.47 Hz, 1H), 6.49 (d, J=1.53 Hz, 1H), 2.34 (s, 3H, CH$_3$).

MS m/z 269 [M+H]$^+$.

Example 63

Synthesis of 5-Methyl-2-(2-oxo-1,2-dihydro-indol-3-ylidene-methyl)-1H-pyrrole-3-carboxylic acid ethyl ester $^1$HNMR (300 MHz, DMSO-d6) δ 13.79 (s, 1H, NH), 11.08 (s, 1H, NH), 8.31 (s, 1H, H-vinyl), 7.45 (d, J=7.52 Hz, 1H), 7.20 (t, J=7.52 Hz, 1H), 7.03 (t, J=7.52 Hz, 1H), 6.91 (d, J=7.52 Hz, 1H), 6.50 (d, J=2.1 Hz, 1H), 4.26 (q, J=7.2 Hz, 2H, OCH$_2$CH$_3$), 2.33 (s, 3H, CH$_3$), 1.32 (t, J=7.2 Hz, 3H, OCH$_2$CH$_3$).

MS m/z 297.1 [M+H]$^+$.

Example 64

Synthesis of 2-(5-Bromo-2-oxo-1,2-dihydroindol-3-ylidenemethyl)-5-methyl-1H-pyrrole-3-carboxylic acid ethyl ester $^1$HNMR (360 MHz, DMSO-d6) δ 13.72(s, 1H, NH), 11.16 (s, 1H, NH), 8.29 (s, 1H, H-vinyl), 7.53 (d, J=2.0 Hz, 1H), 7.35 (dd, J=2.0 & 8.05 Hz, 1H), 6.87 (t, J=8.05 Hz, 1H), 6.53 (d, J=2.4 Hz, 1H), 4.28 (q, J=7.03 Hz, 2H, OCH$_2$CH$_3$), 2.35 (s, 3H, CH$_3$), 1.33 (t, J=7.03 Hz, 3H, OCH$_2$CH$_3$).

MS m/z 375 & 377 [M+H]$^+$.

Example 65

Synthesis of 2-(5-Bromo-2-oxo-1,2-dihydroindol-3-ylidenemethyl)-5-methyl-1H-pyrrole-3-carboxylic acid $^1$HNMR (300 MHz, DMSO-d6) δ 13.72(s, 1H, NH), 12.57 (s, 1H, COOH), 11.19 (s, 1H, NH), 8.36 (s, 1H, H-vinyl), 7.51 (d, J=1.4 Hz, 1H), 7.34 (dd, J=1.4 & 8.17 Hz, 1H), 6.87 (t, J=8.17 Hz, 1H), 6.52 (d, J=2.5 Hz, 1H), 2.35 (s, 3H, CH$_3$).

MS m/z 347 & 349 [M+H]$^+$.

Example 66

Synthesis of 2-(5-Bromo-2-oxo-1,2-dihydroindol-3-ylidenemethyl)-5-methyl-1H-pyrrole-3-carboxylic acid (2-diethylaminoethyl)-amide To a solution of 2-formyl-5-methyl-1H-pyrrole-3-carboxylic acid (320 mg, 2.1 mmol) in dimethylformamide (3 mL) was added 1-ethyl-3-(3-dimethylaminopropyl)carbodiimide (483 mg, 1.2 equiv.), 1-hydroxybenzotriazole (340 mg, 1.2 equiv.), triethylamine (0.59 mL, 2 equiv.) and N,N-diethylethylenediamine (0.32 mL, 1.1 equiv.). After stirring at room temperature overnight, the reaction was diluted with saturated sodium bicarbonate and brine (with extra salt) and extracted with 10% methanol in dichloromethane. The combined organic layers were washed with brine, dried over anhydrous sodium sulfate and concentrated to give 2-formyl-5-methyl-1H-pyrrole-3-carboxylic acid (2-diethylaminoethyl)-amide.

A mixture of 5-bromo-2-oxindole (106 mg, 0.5 mmol), 2-formyl-5-methyl-1H-pyrrole-3-carboxylic acid (2-diethylamino-ethyl)-amide (126 mg, 1 equiv.) and piperidine (0.2 mL) in ethanol (2 mL) was heated in a sealed tube at 80° C. for 1 hr and then cooled. The precipitate was collected by vacuum filtration, washed with ethanol and ethyl acetate and dried to give the title compound as an orange solid.

$^1$HNMR (360 MHz, DMSO-d6) δ 13.62 (s, 1H, NH), 11.11 (br s, 1H, NH), 8.54 (s, 1H, H-vinyl), 8.1 (m, 1H, CONHCH$_2$), 7.49 (d, J=2.2 Hz, 1H), 7.31 (dd, J=2.2 & 8.3 Hz, 1H), 6.86 (d, J=8.3 Hz, 1H), 6.58 (d, J=2.24 Hz, 1H), 3.31 (m, 2H, HNCH$_2$CH$_2$), 2.59 (m, 6H, 3×CH$_2$), 2.36 (s, 3H, CH$_3$), 0.99 (t, J=6.8 Hz, 6H, N(CH$_2$CH$_3$)$_2$).

MS m/z 445/447 [M$^+$ and M$^+$+2].

Example 67

Synthesis of 2,4-dimethyl-5-(2-oxo-1,2-dihydro-indol-3-ylidenemethyl)-1H-pyrrole-3-carboxylic acid (2-diethylamino-ethyl)amide A mixture of 1,3-dihydro-indol-2-one (266 mg, 2 mmol), 5-formyl-2,4-dimethyl-1H-pyrrole-3-carboxylic acid (2-diethylamino-ethyl)-amide (530 mg, 2 mmol) and piperidine (1 drop) in ethanol was heated at 90° C. for 2 hours. The reaction was cooled to room temperature, the resulting precipitate was collected by vacuum filtration, washed with ethanol and dried to give 422 mg (55%) of the title compound as a light yellow solid.

$^1$H NMR (400 MHz, DMSO-d6) δ 13.7 (s, 1H, NH), 10.9 (s, 1H, NH), 7.88 (d, J=7.6 Hz, 1H), 7.64 (s, 1H, H-vinyl), 7.41 (t, J=5.4 Hz, 1H, NH), 7.13 (dt, J=1.2 & 7.6 Hz, 1H), 6.99 (dt, J=1.2 & 7.6 Hz, 1H), 6.88 (d, J=7.6 Hz, 1H), 3.28 (m, 2H), 2.48–2.55 (m, 6H), 2.44 (s, 3H, CH$_3$), 2.41 (s, 3H, CH$_3$), 0.97 (t, J=7.2 Hz, 6H, N(CH$_2$CH$_3$)$_2$).

MS+ve APCI 381 [M$^+$+1].

Example 68

Synthesis of 5-(5-Chloro-2-oxo-1,2-dihydro-indol-3-ylidenemethyl)-2,4-dimethyl-1H-pyrrole-3-carboxylic acid (2-diethylamino-ethyl)-amide A mixture of 5-Chloro-1,3-dihydro-indol-2-one (335 mg, 2 mmol), 5-formyl-2,4-dimethyl-1H-pyrrole-3-carboxylic acid (2-diethylamino-ethyl)-amide (530 mg, 2 mmol) and piperidine (1 drop) in ethanol was heated at 90° C. for 2 hours. The reaction was cooled to room temperature, the resulting precipitate was collected by vacuum filtration, washed with ethanol and dried to give 565 mg (68%) of the title compound as an orange solid.

$^1$H NMR (400 MHz, DMSO-d6) δ 13.65 (s, 1H, NH), 11.0 (s, 1H, NH), 7.98 (d, J=2.1 Hz, 1H) 7.77 (s, 1H H-vinyl), 7.44 (t, NH), 7.13 (dd, J=2,1 & 8.4 Hz, 1H) 6.87 (d, J=8.4 Hz, 1H), 3.28 (g, 2H), 2.48–2.53 (m, 6H), 2.44 (s, 3H, CH$_3$), 2.43 (s, 3H, CH$_3$), 0.97 (t, J=7.0 Hz, 6H, N(CH$_2$CH$_3$)$_2$)

MS+ve APCI 415 [M$^+$+1]

Example 69

Synthesis of 2,4-dimethyl-5-(2-oxo-1,2-dihydro-indol-3-ylidenemethyl)-1H-pyrrole-3-carboxylic acid (2-pyrrolidin-1-ethyl)-amide 1,3-Dihydro-indol-2-one was condensed with 5-formyl-2,4-dimethyl-1H-pyrrole-3-carboxylic acid (2-pyrrolidin-1-yl-ethyl)-amide to give the title compound.

MS+ve APCI 379 [M$^+$+1].

Example 70

Synthesis of 5-(5-Fluoro-2-oxo-1,2-dihydro-indol-3-ylidenemethyl)-2,4-dimethyl-1H-pyrrole-3-carboxylic acid (2-pyrrolidin-1-yl-ethyl)-amide 5-Fluoro-1,3-dihydro-indol-2-one was condensed with 5-formyl-2,4-dimethyl-1H-pyrrole-3-carboxylic acid (2-pyrrolidin-1-yl-ethyl)-amide to give the title compound.

MS+ve APCI 397 [M$^+$+1].

Scale-up Procedure:

5-Formyl-2,4-dimethyl-1H-pyrrole-3-carboxylic acid (61 g), 5-fluoro-1,3-dihydro-indol-2-one (79 g), ethanol (300 mL) and pyrrolidine (32 mL) were refluxed for 4.5 hours. Acetic acid (24 mL) was added to the mixture and refluxing was continued for 30 minutes. The mixture was cooled to room temperature and the solids collected by vacuum filtration and washed twice with ethanol. The solids were stirred for 130 minutes in 40% acetone in water (400 mL) containing 12 N hydrochloric acid (6.5 mL). The solids were collected by vacuum filtration and washed twice with 40% acetone in water. The solids were dried under vacuum to give 5-[5-fluoro-2-oxo-1,2-dihydro-indol-(3Z)-ylidenemethyl]-2,4-dimethyl-1H-pyrrole-3-carboxylic acid (86 g, 79% yield) as an orange solid. $^1$H-NMR (dimethylsulfoxide-d$_6$) δ 2.48, 2.50 (2×s, 6H, 2×CH$_3$), 6.80, 6.88, 7.68, 7.72 (4×m, 4H, aromatic and vinyl), 10.88 (s, 1H, CONH), 12.12 (s, 1H, COOH), 13.82 (s, 1H, pyrrole NH).

MS m/z 299 [M−1].

5-[5-Fluoro-2-oxo-1,2-dihydro-indol-(3Z)-ylidenemethyl]-2,4-dimethyl-1H-pyrrole-3-carboxylic acid (100 g) and dimethylformamide (500 mL) were stirred and benzotriazol-1-yloxytris(dimethylamino)phosphonium hexafluorophosphate (221 g), 1-(2-aminoethyl)pyrrolidine (45.6 g) and triethylamine (93 mL) were added. The mixture was stirred for 2 hours at ambient temperature. The solid product was collected by vacuum filtration and washed with ethanol. The solids were slurry-washed by stirring in ethanol (500 mL) for one hour at 64° C. and cooled to room temperature. The solids were collected by vacuum filtration, washed with ethanol, and dried under vacuum to give 5-[5-fluoro-2-oxo-1,2-dihydro-indol-(3Z)-ylidenemethyl]-2,4-dimethyl-1H-pyrrole-3-carboxylic acid (2-pyrrolidin-1-yl-ethyl)-amide (101.5 g, 77% yield). $^1$H-NMR (dimethylsulfoxide-d$_6$) δ 1.60 (m, 4H, 2×CH$_2$), 2.40, 2.44 (2×s, 6H, 2×CH$_3$), 2.50 (m, 4H, 2×CH$_2$), 2.57, 3.35 (2×m, 4H, 2×CH$_2$), 7.53, 7.70, 7.73, 7.76 (4×m, 4H, aromatic and vinyl), 10.88 (s, 1H, CONH), 13.67 (s, 1H, pyrrole NH). MS m/z 396 [M$^+$].

Example 71

Synthesis of 5-(5-Chloro-2-oxo-1,2-dihydro-indol-3-ylidenemethyl)-2,4-dimethyl-1H-pyrrole-3-carboxylic acid (2-pyrrolidin-1-yl-ethyl)-amide 5-Chloro-1,3-dihydro-indol-2-one was condensed with 5-formyl-2,4-dimethyl-1H-pyrrole-3-carboxylic acid (2-pyrrolidin-1-yl-ethyl)-amide to give the title compound. MS+ve APCI 413 [M$^+$+1].

Example 72

Synthesis of 2,4-dimethyl-5-(2-oxo-1,2-dihydro-indol-3-ylidenemethyl)-1H-pyrrole-3-carboxylic acid (2-dimethylaminoethyl)-amide 1,3-Dihydro-indol-2-one was condensed with 5-formyl-2,4-dimethyl-1H-pyrrole-3-carboxylic acid (2-dimethylamino-ethyl)amide to give the title compound.

$^1$H NMR (400 MHz, DMSO-d6) δ 13.63 (s, 1H, NH), 10.90 (s, 1H, NH), 7.78 (d, J=7.8 Hz, 1H), 7.63 (s, 1H H-vinyl), 7.48 (t, 1H, NH), 7.13 (dt, 1H), 6.98 (dt, 1H), 6.88 (d, J=7.7 Hz, 1H), 3.31 (q, J=6.6 Hz, 2H), 2.43 (s, 3H, CH$_3$), 2.40 (s, 3H, CH$_3$), 2.38 (t, J=6.6 Hz, 2H), 2.19 (s, 6H, N(CH$_2$CH$_3$)$_2$).

MS+ve APCI 353 [M$^+$+1].

Example 73

Synthesis of 5-(5-Fluoro-2-oxo-1,2-dihydro-indol-3-ylidenemethyl)-2,4-dimethyl-1H-pyrrole-3-carboxylic acid (2-dimethylaminoethyl)-amide 5-Fluoro-1,3-dihydro-indol-2-one was condensed with 5-formyl-2,4-dimethyl-1H-pyrrole-3-carboxylic acid (2-dimethylaminoethyl)amide to give the title compound.

$^1$H NMR (400 MHz, DMSO-d6) δ 13.68 (s, 1H, NH), 10.90 (s, 1H, NH), 7.76 (dd, J=2.4 & 9.4 Hz, 1H), 7.71 (s, 1H H-vinyl), 7.51 (t, 1H, NH), 6.93 (m, 1H), 6.84 (dd, J=4.6 & 8.4 Hz, 1H), 3.31 (q, J=6.6 Hz, 2H), 2.43 (s, 3H, CH$_3$), 2.41 (s, 3H, CH$_3$), 2.38 (t, J=6.6 Hz, 2H), 2.19 (s, 6H, N(CH$_2$CH$_3$)$_2$. MS+ve APCI 371 [M$^+$+1].

Example 74

Synthesis of 5-[5-Fluoro-2-oxo-1,2-dihydro-indol-(3Z)-ylidenemethyl]-2,4-dimethyl-1H-pyrrole-3-carboxylic acid (2-ethylamino-ethyl)-amide 5-Formyl-2,4-dimethyl-1H-pyrrole-3-carboxylic acid (2-ethylamino-ethyl)-amide (99 g), ethanol (400 mL), 5-fluoro-2-oxindole (32 g) and pyrrolidine (1.5 g) were refluxed for 3 hours with stirring. The mixture was cooled to room temperature and the solids collected by vacuum filtration. The solids were stirred in ethanol at 60° C., cooled to room temperature and collected by vacuum filtration. The product was dried under vacuum to give 5-[5-fluoro-2-oxo-1,2-dihydro-indol-(3Z)-ylidenemethyl]-2,4-dimethyl-1H-pyrrole-3-carboxylic acid (2-ethylamino-ethyl)-amide (75 g, 95% yield). $^1$H-NMR (dimethylsulfoxide-d$_6$) δ 1.03 (t, 3H, CH$_3$), 2.42, 2.44 (2×s, 6H, 2×CH$_3$), 2.56 (q, 2H, CH$_2$), 2.70, 3.30 (2×t, 4H, 2×CH$_2$), 6.85, 6.92, 7.58, 7.72, 7.76 (5×m, 5H, aromatic, vinyl and CONH), 10.90 (br s, 1H, CONH), 13.65 (br s, 1H, pyrrole NH). MS m/z 369 [M−1].

Example 75

Synthesis of 5-[5-Fluoro-2-oxo-1,2-dihydro-indol-(3Z)-ylidenemethyl]-2,4-dimethyl-1H-pyrrole-3-carboxylic acid (2-diethyl-N-oxoamino-ethyl)-amide Method A:

5-[5-Fluoro-2-oxo-1,2-dihydro-indol-(3Z)-ylidenemethyl]-2,4-dimethyl-1H-pyrrole-3-carboxylic acid (2-diethylamino-ethyl)-amide (598 mg) and dichloromethane (60 mL) in an ice bath were treated with 3-chloroperbenzoic acid (336 mg) and the mixture stirred at room temperature overnight. The solvent was rotary evaporated and the residue suspended in methanol (20 mL). Water (20 mL) containing sodium hydroxide (240 mg) was added and the mixture stirred for one hour. The precipitate was collected by vacuum filtration, washed with 5 mL of water and dried under a vacuum to give 5-[5-fluoro-2-oxo-1,2-dihydro-indol-(3Z)-ylidenemethyl]-2,4-dimethyl-1H-pyrrole-3-carboxylic acid (2-diethyl-N-oxoamino-ethyl)-amide (510 mg, 82% yield) as an orange solid. $^1$H-NMR (DMSO-d6) δ 13.72 (br s, 1H, NH), 11.02 (br s, 1H, CONH), 9.81 (br s, 1H, CONH), 7.75 (dd, 1H, aromatic), 7.70 (s, 1H, aromatic), 6.93 (td, 1H, aromatic), 6.84 (m, 1H, aromatic), 3.63 (m, 2H, $CH_2$), 3.29 (m, 2H, $CH_2$), 3.14 (m, 4H, 2×$CH_2$), 2.47 (s, 1H, $CH_3$), 2.45 (s, 3H, $CH_3$), 1.64 (t, 6H, 2×$CH_3$). MS m/z 415 [M+1].

Method B:

5-Formyl-2,4-dimethyl-1H-pyrrole-3-carboxylic acid (2-diethylamino-ethyl)-amide (10 g) was suspended in dichloromethane (100 mL) and cooled in an ice bath. 3-Chloro-peroxybenzoic acid (13.1 g) was added with stirring and the mixture allowed to warm to room temperature and then stirred ovenight. The mixture was rotary evaporated to dryness and chromatographed on a column of silica gel eluting with 20% methanol in dichloromethane. Fractions containing product were combined and rotary evaporated to dryness to give 5-formyl-2,4-dimethyl-1H-pyrrole-3-carboxylic acid (2-diethyl-N-oxoamino-ethyl)-amide (9 g, 83% yield).

5-Formyl-2,4-dimethyl-1H-pyrrole-3-carboxylic acid (2-diethyl-N-oxoamino-ethyl)-amide (9 g), 5-fluoro-1,3-dihydro-indol-2-one ((9 g, 83% yield)), and pyrrolidine ((9 g, 83% yield (0.1 g) were refluxed in ethanol (30 mL) for 4 hours. The mixture was cooled in an ice bath and the precipitate collected by vacuum filtration and washed with ethanol. The solids were stirred in ethyl acetate (30 mL), collected by vacuum filtration, washed with ethyl acetate and dried under vacuum to give 5-[5-fluoro-2-oxo-1,2-dihydro-indol-(3Z)-ylidenemethyl]-2,4-dimethyl-1H-pyrrole-3-carboxylic acid (2-diethyl-N-oxoamino-ethyl)-amide (10.3 g 80% yield) as an orange solid. $^1$H-NMR (DMSO-d6) δ 13.72 (br s, 1H, NH), 11.02 (br s, 1H, CONH), 9.81 (br s, 1H, CONH), 7.75 (dd, 1H, aromatic), 7.70 (s, 1H, aromatic), 6.93 (td, 1H, aromatic), 6.84 (m, 1H, aromatic), 3.63 (m, 2H, $CH_2$), 3.29 (m, 2H, $CH_2$), 3.14 (m, 4H, 2×$CH_2$), 2.47 (s, 1H, $CH_3$), 2.45 (s, 3H, $CH_3$), 1.64 (t, 6H, 2×$CH_3$). MS m/z 415 [M+1].

Example 76

Synthesis of 5-[5-fluoro-2-oxo-1,2-dihydro-indol-(3Z)-ylidenemethyl]-2,4-dimethyl-1H-pyrrole-3-carboxylic acid [2-(pyridin-1-yl)ethyl]-amide 5-[5-Fluoro-2-oxo-1,2-dihydro-indol-(3Z)-ylidenemethyl]-2,4-dimethyl-1H-pyrrole-3-carboxylic acid (120 mg, 0.4 mmol) was shaken with EDC, HCl (96 mg, 0.5 mmol), anhydrous 1-hydroxy-benztriazole (68 mg, 0.5 mmol), and 2-(2-aminoethylpyridine purchased from Aldrich in anhydrous DMF (3 mL) for 2–3 days at room temperature. The reaction mixture was diluted with 1M NaHCO3 (1.5 ml), then with 8 ml of water. The precipitated crude product was collected by filtration, washed with water, dried and purified by crystallization or chromatography to give 5-[5-fluoro-2-oxo-1,2-dihydro-indol-(3Z)-ylidenemethyl]-2,4-dimethyl-1H-pyrrole-3-carboxylic acid [2-(pyridin-1-yl)-ethyl]amide.

Example 77

Synthesis of 5-[5-Chloro-2-oxo-1,2-dihydro-indol-(3Z)-ylidenemethyl]-2,4-dimethyl-1H-pyrrole-3-carboxylic acid [2-(pyridin-1-yl)ethyl]amide Proceeding as described in previous example but substituting 5-[5-fluoro-2-oxo-1,2-dihydro-indol-(3Z)-ylidenemethyl]-2,4-dimethyl-1H-pyrrole-3-carboxylic acid with 5-[5-chloro-2-oxo-1,2-dihydro-indol-(3Z)-ylidenemethyl]-2,4-dimethyl-1H-pyrrole-3-carboxylic acid (127 mg) provided 5-[5-chloro-2-oxo-1,2-dihydro-indol-(3Z)-ylidenemethyl]-2,4-dimethyl-1H-pyrrole-3-carboxylic acid [2-(pyridin-1-yl)ethyl]amide.

Example 78

Synthesis of 5-[5-Bromo-2-oxo-1,2-dihydro-indol-(3Z)-ylidenemethyl]-2,4-dimethyl-1H-pyrrole-3-carboxylic acid [2-(pyridin-1-yl)ethyl]amide Proceeding as described in Example 76 above but substituting 5-[5-fluoro-2-oxo-1,2-dihydro-indol-(3Z)-ylidenemethyl]-2,4-dimethyl-1H-pyrrole-3-carboxylic acid with 5-[5-bromo-2-oxo-1,2-dihydro-indol-(3Z)-ylidenemethyl]-2,4-dimethyl-1H-pyrrole-3-carboxylic acid (145 mg) provided 5-[5-bromo-2-oxo-1,2-dihydro-indol-(3Z)-ylidenemethyl]-2,4-dimethyl-1H-pyrrole-3-carboxylic acid [2-(pyridin-1-yl)ethyl]amide.

Example 79

Synthesis of 5-[2-Oxo-1,2-dihydro-indol-(3Z)-ylidenemethyl]-2,4-dimethyl-1H-pyrrole-3-carboxylic acid [2-(pyridin-1-yl)ethyl]amide Proceeding as described in Example 76 above but substituting 5-[5-fluoro-2-oxo-1,2-dihydro-indol-(3Z)-ylidenemethyl]-2,4-dimethyl-1H-pyrrole-3-carboxylic acid with 5-[2-oxo-1,2 -dihydro-indol-(3Z)-ylidenemethyl]-2,4-dimethyl-1H-pyrrole-3-carboxylic acid (113 mg) provided 5-[2-oxo-1,2-dihydro-indol-(3Z)-ylidenemethyl]-2,4-dimethyl-1H-pyrrole-3-carboxylic acid [2-(pyridin-1-yl)ethyl]amide.

Example 80

Synthesis of 5-[5-Cyano-2-oxo-1,2-dihydro-indol-(3Z)-ylidenemethyl]-2,4-dimethyl-1H-pyrrole-3-carboxylic acid [2-(pyridin-1-yl)ethyl]amide Proceeding as described in Example 76 above but substituting 5-[5-fluoro-2-oxo-1,2-dihydro-indol-(3Z)-ylidenemethyl]-2,4-dimethyl-1H-pyrrole-3-carboxylic acid with 5-[5-cyano-2-oxo-1,2-dihydro-indol-(3Z)-ylidenemethyl]-2,4-dimethyl-1H-pyrrole-3-carboxylic acid (123 mg) provided 5-[5-cyano-2-oxo-1,2-dihydro-indol-(3Z)-ylidenemethyl]-2,4-dimethyl-1H-pyrrole-3-carboxylic acid [2-(pyridin-1-yl)ethyl]amide.

Examples 81–85

Proceeding as described in Examples 76–80 above but substituting 2-(2-aminoethyl)pyridine with 1-(2-aminoethyl)pyrrolidine, purchased from Aldrich Chemical Company, Inc. provided the desired compounds.

Examples 86–90

Proceeding as described in Examples 76–80 above but substituting 2-(2-aminoethyl)pyridine with 1-(2-aminoethyl)imidazolin-2-one (prepared by heating dimethyl carbonate with bis(2-aminoethyl) amine (2 equivalents) in a sealed flask to 150° C. for 30 min., following the procedure described in U.S. Pat. No. 2,613,212 (1950), to Rohm & Haas Co. The crude product was purified on silica using an eluent mixture chloroform-methanol-aqueous ammonia 80:25:2) provided the desired compounds.

Examples 91–96

Proceeding as described in Examples 76–80 above but substituting 2-(2-aminoethyl)pyridine with 4-(2-aminoethyl)piperazine-1-acetic acid ethyl ester (prepared as follows: Piperazine-1-acetic acid ethyl ester (11.22 g) was treated with iodoacetonitrile (5.0 mL) in the presence of potassium carbonate (6.9 g) in ethyl acetate (260 mL) at 0° C. After complete iodoacetonitrile addition (45 min), the reaction mixture was subsequently stirred at room temperature for 11 hours. The reaction mixture was filtered and the filtrates evaporated. The residue was hydrogenated in a presence of cobalt boride (prepared from CoCl2 and sodium borohydride) at room temperature at 50 psi for 2 days in ethanol. Filtration, evaporation and chromatographic purification using an eluent mixture chloroform-methanol-aqueous ammonia 80:25:2 provided the desired amine (3.306 g) as a pale yellow oil) provided the desired compounds.

Example 97–101

Proceeding as described in Examples 76–80 above but substituting 2-(2-aminoethyl)pyridine with 2-[(2-aminoethylamino)]acetonitrile (prepared as follows: A solution of iodoacetonitrile (50 mmol) in ethyl alcohol (80 ml) was added to a solution of ethylene diamine (150 ml) in ethyl alcohol (60 ml) at 0° C. over a period of 30 minutes. The stirring was continued for another 1 hr at 0° C., then at room temperature for 14 hours. 55 mmol of potassium carbonate was added, stirred for 30 minutes, filtered and the filtrate was concentrated at room temperature. The residue was purified on silica using an eluent mixture chloroform-methanol-aqueous ammonia 80:15:1.5 to give 2-[(2-aminoethylamino)]-acetonittile (3.550 g) which was used immediately) provided the desired compounds.

Example 102–107

Proceeding as described in Examples 76–80 above but substituting 2-(2-aminoethyl)pyridine with 1-(3-aminopropyl)-azepin-2-one (prepared according to the procedure in Kraft A.: J. Chem. Soc. Perkin Trans. 1, 6, 1999, 705–14, except that the hydrolysis of DBU was performed at 145° C. neat in a presence of lithium hydroxide (1 hr, 5 ml of DBU, 2 ml of water, 420 mg of lithium hydroxide hydrate). Purification of the crude product on silica using an eluent mixture chloroform-methanol-aqueous ammonia 80:40:4 provided 1-(3-aminopropyl)azepin-2-one (4.973 g, 87% yield)) provide the desired compounds.

Examples 108–112

Proceeding as described in Examples 76–80 above but substituting 2-(2-aminoethyl)pyridine with N-acetyl ethylene diamine, (prepared by heating a mixture of ethyl acetate with ethylene diamine (1.5 equivalents) to 160° C. for 1 hr in a sealed vessel. The vacuum distillation provided the desired product in 56% yield. N-acetylethylene diamine is also available from Aldrich) provide the desired compounds.

Examples 113–117

Proceeding as described in Examples 76–80 above but substituting 2-(2-aminoethyl)pyridine with 1-(3-aminopropyl)-tetrahydro-pyrimidin-2-one (prepared in the same way as 1-(3-aminopropyl)-azepin-2-one according to the procedure in Kraft A.: J. Chem. Soc. Perkin Trans. 1, 6, 1999, 705–14: Briefly, 1,3,4,6,7,8-hexahydro-2H-pyrimido[1,2-a]pyrimidine (4.939 g), lithium hydroxide hydrate (918 mg) and 2 ml of water was heated without a solvent in a sealed vessel to 145° C. for 1 hr. The crude product was purified on a column of silica in chloroform-methanol-aqueous ammonia 80:40:4 to give pure amine (5.265 g, 94% yield).

Examples 118–122

Proceeding as described in Examples 76–80 above but substituting 2-(2-aminoethyl)pyridine with 1-(2-aminoethyl)-piperazine- 2-one (prepared as follows: Neat tert-butyldiphenylsilyl chloride (25 mL, 97.7 mmol) was added dropwise into a solution of DBU (19.5 ml, 130 mmol) and bis(2-aminoethyl)amine (4.32 mL, 40 mmol) in anhydrous dimethyl acetamide (80 mL) at room temperature upon cooling on water bath within 5 minutes. The mixture was stirred for 5 hours. Bromoacetic acid ethyl ester (6.70 mL, 60 mmol) was added neat upon cooling to room temperature. The reaction was stirred for 25 minutes, then evaporated on high vacuum. The residue was dissolved in methanol (200 ml), KHCO$_3$ (10 g) and KF (12 g, 200 mmol) were added and the mixture was stirred at 60° C. for 5 hours. 10 g of Na$_2$CO$_3$ was added, stirred for 10 minutes, cooled and filtered. The filtrates were evaporated. The residue was extracted with hexanes (2 times 250 ml). The hexane-insoluble material was dissolved in ethanol (60 ml), filtered and evaporated. The residue was purified on column of silica in chloroform-methanol-aqueous ammonia 80:40:4 to give pure amine (4.245 g, 74% yield)) provided the desired compounds.

Examples 123–127

Proceeding as described in Examples 76–80 above but substituting 2-(2-aminoethyl)pyridine with 3-[(2-aminoethyl)amino]propionitrile (prepared from ethylene diamine (150 mmol) and acrylonitrile (50 mmol) in THF at room temperature, as described in Israel, M. et al: *J. Med Chem.* 7, 1964, 710–16., provided the desired amine (4.294 g)) provided the desired compounds.

Example 128

Synthesis of 5-(5-Fluoro-2-oxo-1,2-dihydro-indol-3-ylidenemethyl)-2,4-dimethyl-1H-pyrrole-3-carboxylic acid [2-(4-methylpiperazin-1-yl)-ethyl]-amide To a stirred yellow muddy mixture of 5-[5-fluoro-2-oxo-1,2-dihydro-indol-(3Z)-ylidenemethyl]-2,4-dimethyl-1H-pyrrole-3-carboxylic acid (90 mg), DMF (0.8 mL) and TEA (0.084 mL) in a 20 mL reaction tube, was added BOP reagent (199 mg). The mixture became clear in 5 min. 2-(4-Methylpiperazin-1-yl)ethylamine[1] (51 mg) was added into the clear mixture. The resulting solution was stirred at room temperature over night. Yellow solid products precipitated from the reaction system. Thin layer chromatography (10% methanol in methylene chloride) showed that all the starting material had been converted into the product. The solid was isolated by vacuum filtration and washed once with ethanol (1 mL). The solid was sonicated in diethyl ether (2 mL) for 20 min and collected by vacuum filtration. After drying under vacuum, 5-(5-Fluoro-2-oxo-1,2-dihydro-indol-3-ylidenemethyl)-2,4-dimethyl-1H-pyrrole-3-carboxylic acid (4-methylpiperazin-1-yl-ethyl)-amide (79 mg, 62% yield) was obtained.

$^1$H NMR (DMSO-$d_6$) δ 2.13 (s, 3H, CH$_3$), 2.40, 2.42 (2×s, 6H, 2×CH$_3$), 2.41 (m, 2H, CH$_2$), 2.47 (m, 8H, 4×CH$_2$), 3.30 (m, 2H, CH$_2$), 6.82 (dd, J=4.5, 8.7 Hz, 1H), 6.91(td, $^2$J=2.4, $^3$J=8.8 Hz, 1H), 7.43 (t, J=5.6 Hz, 1H), 7.70 (s, 1H), 7.75 (dd, J=2.8, 9.6 Hz, 1H) (aromatic and vinyl); 10.88 (s, 1H, CONH), 13.67 (s, 1H, NH). LC-MS (m/z) 424.4 (M−1).

Example 129

Synthesis of 5-(5-Chloro-2-oxo-1,2-dihydro-indol-3-ylidenemethyl)-2,4-dimethyl-1H-pyrrole-3-carboxylic acid (4-methylpiperazin-1-yl-ethyl)-amide Following the procedure in Example 128 above but substituting 5-[5-fluoro-2-oxo-1,2-dihydro-indol-(3Z)-ylidenemethyl]-2,4-dimethyl-1H-pyrrole-3-carboxylic acid with 5-[5-chloro-2-oxo-1,2-dihydro-indol-(3Z)-ylidenemethyl]-2,4-dimethyl-1H-pyrrole-3-carboxylic acid (95 mg, 0.3 mmol) gave 5-(5-chloro-2-oxo-1,2-dihydro-indol-3-ylidenemethyl)-2,4-dimethyl-1H-pyrrole-3-carboxylic acid (4-methylpiperazin-1-yl-ethyl)-amide (76 mg, 58%).

$^1$H NMR (DMSO-$d_6$) δ 2.13 (s, 3H, CH$_3$), 2.41, 2.42 (2×s, 6H, 2×CH$_3$), 2.42 (m, 2H, CH$_2$), 2.48 (m, 8H, 4×CH$_2$), 3.30 (m, 2H, CH$_2$), 6.84 (d, J=8.0 Hz, 1H), 7.11 (dd, J=2.0, 8.0 Hz, 1H), 7.44 (t, J=5.6 Hz, 1H), 7.76 (s, 1H), 7.97 (d, J=2.0 Hz, 1H) (aromatic and vinyl), 10.98 (s, 1H, CONH), 13.62 (s, 1H, NH). LC-MS (m/z) 440.2 (M−1).

Example 130

Synthesis of 5-(5-Bromo-2-oxo-1,2-dihydro-indol-3-ylidenemethyl)-2,4-dimethyl-1H-pyrrole-3-carboxylic acid (4-methylpiperazin-1-yl-ethyl)-amide Following the procedure described in Example 128, but substituting 5-(5-chloro-2-oxo-1,2-dihydro-indol-3-ylidenemethyl)-2,4-dimethyl-1H-pyrrole-3-carboxylic acid with 5-(5-bromo-2-oxo-1,2-dihydro-indol-3-ylidenemethyl)-2,4-dimethyl-1H-pyrrole-3-carboxylic acid gave 5-(5-bromo-2-oxo-1,2-dihydro-indol-3-ylidenemethyl)-2,4-dimethyl-1H-pyrrole-3-carboxylic acid (4-methylpiperazin-1-yl-ethyl)-amide (39 mg, 54%) was obtained from SU011670 (54 mg, 0.15 mmol).

$^1$H NMR (DMSO-$d_6$) δ 2.14 (s, 3H, CH$_3$), 2.41, 2.42 (2×s, 6H, 2×CH$_3$), 2.42 (m, 2H, CH$_2$), 2.48 (m, 8H, 4×CH$_2$), 3.31 (m, 2H, CH$_2$), 6.80 (d, J=8.0 Hz, 1H), 7.23 (dd, J=2.0, 8.0 Hz, 1H), 7.44 (t, J=5.6 Hz, 1H), 7.76 (s, 1H), 8.09 (d, J=2.0 Hz, 1H) (aromatic and vinyl), 10.99 (s, 1H, CONH), 13.61 (s, 1H, NH). LC-MS (m/z) 486.6 (M).

Example 131

Synthesis of 5-(2-Oxo-1,2-dihydro-indol-3-ylidenemethyl)-2,4-dimethyl-1H-pyrrole-3-carboxylic acid (4-methylpiperazin-1-yl-ethyl)-amide Following the procedure described in Example 128 above but substituting 5-(5-fluoro-2-oxo-1,2-dihydro-indol-3-ylidenemethyl)-2,4-dimethyl-1H-pyrrole-3-carboxylic acid SU014900 with 5-(2-oxo-1,2-dihydro-indol-3-ylidenemethyl)-2,4-dimethyl-1H-pyrrole-3-carboxylic acid gave 5-(2-oxo-1,2-dihydro-indol-3-ylidenemethyl)-2,4-dimethyl-1H-pyrrole-3-carboxylic acid (4-methylpiperazin-1-yl-ethyl)-amide, SU014903 (136 mg, 84%) was obtained from SU012120 (112.8 mg, 0.4 mmol).

$^1$H-NMR (DMSO-$d_6$) δ 2.13 (s, 3H, CH$_3$), 2.39, 2.42 (2×s, 6H, 2×CH$_3$), 2.42 (m, 2H, CH$_2$), 2.48 (m, 8H, 4×CH$_2$), 3.30 (t, 2H, CH$_2$), 6.86 (d, J=8.0 Hz, 1H), 6.96 (t, J=7.4 Hz, 1H), 7.10 (t, J=7.8 Hz, 1H), 7.41 (t, J=5.4 Hz, 1H), 7.62 (s, 1H), 7.76 (d, J=7.6 Hz, 1H) (aromatic and vinyl), 10.88 (s, 1H, CONH), 13.61 (s, 1H, NH). LC-MS (m/z) 406.6 (M−1).

Example 132

Synthesis of 5-[2-Oxo-1,2-dihydro-indol-(3Z)-ylidenemethyl]-2,4-dimethyl-1H-pyrrole-3-carboxylic acid [2-(3,5-dimethylpiperazin-1-yl)ethyl)amide To a stirred yellow muddy mixture of 5-[2-oxo-1,2-dihydro-indol-(3Z)-ylidenemethyl]-2,4-dimethyl-1H-pyrrole-3-carboxylic acid (112.8 mg, 0.4 mmol), DMF (0.5 mL) and triethylamine (0.111 mL) in a 20 mL reaction tube, was added BOP reagent (265 mg). The mixture became clear in 5 min. 2-(2,6-dimethylpiperazin-1-yl)ethylamine (68.6 mg) (see., Tapia, L. Alonso-Cires, P. Lopez-T.udanca, R. Mosquera, L. Labeaga, A. Innerarity, A. Orjales, J. Med. Chem., 1999, 42, 2870–2880) was added into the clear mixture. The resulting solution was stirred at room temperature over night. Thin layer chromatography (10% methanol in methylene chloride) showed that all the starting material had been converted into the product. The reaction mixture was evaporated to dryness and then purified by flash chromatography (CH$_2$Cl$_2$/CH$_3$OH=20/1–15/1) followed by recrystalization to give 5-(2-oxo-1,2-dihydro-indol-(3Z)-ylidenemethyl]-2,4-dimethyl-1H-pyrrole-3-carboxylic acid [2-(3,5-dimethylpiperazin-1-yl)ethyl)amide (83 mg, 50% yield).

$^1$H NMR (DMSO-$d_6$) δ 1.15, 1.16 (2×s, 6H, 2×CH$_3$), 1.95 (t, J=11.6 Hz, 2H, CH$_2$), 2.41, 2.47 (2×s, 6H, 2×CH$_3$), 2.50 (m, 2H, CH$_2$), 3.03 (d, J=10 Hz, 2H), 3.19 (m, 2H), 3.30 (m, 2H, CH$_2$), 6.86 (d, J=8.0 Hz, 1H), 6.97 (t, J=7.2 Hz, 1H), 7.11 (t, J=7.8 Hz, 1H), 7.48 (t, J=5.6 Hz, 1H), 7.61 (s, 1H), 7.75 (d, J=7.6 Hz, 1H) (aromatic and vinyl), 10.88 (s, 1H, CONH), 13.62 (s, 1H, NH). LC-MS (m/z) 422.2 (M+1).

Example 133

Synthesis of 5-[5-Fluoro-2-oxo-1,2-dihydro-indol-(3Z)-ylidenemethyl]-2,4-dimethyl-1H-pyrrole-3-carboxylic acid [2-(3,5-dimethylpiperazin-1-yl)ethyl)amide Following the procedure described in Example 128 above the desired compound was obtained (60 mg, 0.2 mmol).

$^1$H NMR (DMSO-$d_6$) δ 0.891, 0.907 (2×s, 6H, 2×CH$_3$), 1.49 (t, J=10.4 Hz, 2H), 2.40, 2.42 (2×s, 6H, 2×CH$_3$), 2.41 (m, 2H, CH$_2$), 2.74 (m, 4H), 3.30 (m, 2H), 6.82 (dd, J=4.5, 8.7 Hz, 1H), 6.90 (td, $^2$J=2.4, $^3$J=8.4 Hz, 1H), 7.42 (t, J=5.6 Hz, 1H), 7.70 (s, 1H), 7.74 (dd, J=4.6, 8.4 Hz, 1H) (aromatic and vinyl), 10.88 (s, 1H, CONH), 13.65 (s, 1H, NH). LC-MS (m/z) 438.4 (M−1).

Example 134

Synthesis of 5-[5-Chloro-2-oxo-1,2-dihydro-indol-(3Z)-ylidenemethyl]-2,4-dimethyl-1H-pyrrole-3-carboxylic acid [2-(3,5-dimethylpiperazin-1-yl)ethyl)amide Following the procedure for Example 132 above the desired compound (31.2 mg, 34%) was obtained from 5-[5-chloro-2-oxo-1,2-dihydro-indol-(3Z)-ylidenemethyl]-2,4-dimethyl-1H-pyrrole-3-carboxylic acid (63 mg, 0.2 mmol).

$^1$H NMR (DMSO-d$_6$) δ 1.15, 1.16 (2×s, 6H, 2×CH$_3$), 1.95 (t, J=11.6 Hz, 2H, CH$_2$), 2.40, 2.42 (2×s, 6H, 2×CH$_3$), 2.50 (m, 2H, CH$_2$), 3.03 (d, J=11.2 Hz, 2H), 3.19 (m, 2H), 3.30 (m, 2H, CH$_2$), 6.85 (d, J=8.4 Hz, 1H), 7.11 (dd, J=2.0, 8.0 Hz, 1H), 7.52 (t, J=5.6 Hz, 1H), 7.76 (s, 1H), 7.97 (d, J=2.0 Hz, 1H) (aromatic and vinyl), 10.99 (s, 1H, CONH), 13.63 (s, 1H, NH). LC-MS (m/z) 456.2 (M+1).

Example 135

Synthesis of 5-[5-Bromo-2-oxo-1,2-dihydro-indol-(3Z)-ylidenemethyl]-2,4-dimethyl-1H-pyrrole-3-carboxylic acid (2-(3,5-dimethylpiperazin-1-yl)ethyl)amide Following the procedure described in Example 132 the desired compound (40 mg, 40%) was obtained from 5-(5-bromo-2-oxo-1,2-dihydro-indol-(3Z)-ylidenemethyl]-2,4-dimethyl-1H-pyrrole-3-carboxylic acid (74 mg, 0.2 mmol).

$^1$H NMR (DMSO-d$_6$) δ 1.15, 1.16 (2×s, 6H, 2×CH$_3$), 1.95 (t, J=11.6 Hz, 2H, CH$_2$), 2.40, 2.42 (2×s, 6H, 2×CH$_3$), 2.50 (m, 2H, CH$_2$), 3.03 (d, J=10.4 Hz, 2H), 3.19 (m, 2H), 3.30 (m, 2H, CH$_2$), 6.81 (d, J=8.4 Hz, 1H), 7.24 (dd, J=2.0, 8.4 Hz, 1H), 7.51 (t, J=5.6 Hz, 1H), 7.76 (s, 1H), 8.10 (d, J=2.0 Hz, 1H) (aromatic and vinyl), 10.99 (s, 1H, CONH), 13.62 (s, 1H, NH). LC-MS (m/z) 498.4 (M−1)

Biological Examples

A. Assay Procedures.

The following assays may be used to determine the level of activity and effect of the different compounds of the present invention on one or more of the PKs. Similar assays can be designed along the same lines for any PK using techniques well known in the art.

Several of the assays described herein are performed in an ELISA (Enzyme-Linked Immunosorbent Sandwich Assay) format (Voller, et al., 1980, "Enzyme-Linked Immunosorbent Assay," Manual of Clinical Immunology, 2d ed., Rose and Friedman, Am. Soc. Of Microbiology, Washington, D.C., pp. 359–371). The general procedure is as follows: a compound is introduced to cells expressing the test kinase, either naturally or recombinantly, for a selected period of time after which, if the test kinase is a receptor, a ligand known to activate the receptor is added. The cells are lysed and the lysate is transferred to the wells of an ELISA plate previously coated with a specific antibody recognizing the substrate of the enzymatic phosphorylation reaction. Non-substrate components of the cell lysate are washed away and the amount of phosphorylation on the substrate is detected with an antibody specifically recognizing phosphotyrosine compared with control cells that were not contacted with a test compound.

The presently preferred protocols for conducting the ELISA experiments for specific PKs is provided below. However, adaptation of these protocols for determining the activity of compounds against other RTKS, as well as for CTKs and STKs, is well within the scope of knowledge of those skilled in the art. Other assays described herein measure the amount of DNA made in response to activation of a test kinase, which is a general measure of a proliferative response. The general procedure for this assay is as follows: a compound is introduced to cells expressing the test kinase, either naturally or recombinantly, for a selected period of time after which, if the test kinase is a receptor, a ligand known to activate the receptor is added. After incubation at least overnight, a DNA labeling reagent such as 5-bromodeoxyuridine (BrdU) or H$^3$-thymidine is added. The amount of labeled DNA is detected with either an anti-BrdU antibody or by measuring radioactivity and is compared to control cells not contacted with a test compound.

GST-Flk-1 Bioassay

This assay analyzes the tyrosine kinase activity of GST-Flk1 on poly(glu,tyr) peptides.

Materials and Reagents:
1. Corning 96-well ELISA plates (Corning Catalog No. 5805-96).
2. poly(glu,tyr) 4:1, lyophilizate (Sigma Catalog #P0275).
3. Preparation of poly(glu,tyr) (pEY) coated assay plates: Coat 2 ug/well of poly(glu,tyr) (pEY) in 100 ul PBS, hold at room temperature for 2 hours or at 4° C. overnight. Cover plates well to prevent evaporation.
4. PBS Buffer: for 1 L, mix 0.2 g KH$_2$PO$_4$, 1.15 g Na$_2$HPO$_4$, 0.2 g KCl and 8 g NaCl in approx. 900 ml dH$_2$O. When all reagents have dissolved, adjust the pH to 7.2 with HCl. Bring total volume to 1 L with dH$_2$O.
5. PBST Buffer: to 1 L of PBS Buffer, add 1.0 ml Tween-20.
6. TBB—Blocking Buffer: for 1 L, mix 1.21 g TRIS, 8.77 g NaCl, 1 ml TWEEN-20 in approximately 900 ml dH$_2$O. Adjust pH to 7.2 with HCl. Add 10 g BSA, stir to dissolve. Bring total volume to 1 L with dH$_2$O. Filter to remove particulate matter.
7. 1% BSA in PBS: To make a 1× working solution, add 10 g BSA to approx. 990 ml PBS buffer, stir to dissolve. Adjust total volume to 1 L with PBS buffer, filter to remove particulate matter.
8. 50 mM Hepes pH 7.5.
9. GST-Flk1cd purified from sf9 recombinant baculovirus transformation (SUGEN, Inc.).
10. 4% DMSO in dH$_2$O.
11. 10 mM ATP in dH$_2$O.
12. 40 mM MnCl$_2$
13. Kinase Dilution Buffer (KDB): mix 10 ml Hepes (pH 7.5), 1 ml 5M NaCl, 40 μL 100 mM sodium orthovanadate and 0.4 ml of 5% BSA in dH$_2$O with 88.56 ml dH$_2$O.
14. NUNC 96-well V bottom polypropylene plates, Applied Scientific Catalog #AS-72092
15. EDTA: mix 14.12 g ethylenediaminetetraacetic acid (EDTA) to approx. 70 ml dH$_2$O. Add 10 N NaOH until EDTA dissolves. Adjust pH to 8.0. Adjust total volume to 100 ml with dH$_2$O.
16. 1° Antibody Dilution Buffer: mix 10 ml of 5% BSA in PBS buffer with 89.5 ml TBST.

17. Anti-phosphotyrosine monoclonal antibody conjugated to horseradish peroxidase (PY99 HRP, Santa Cruz Biotech).
18. 2,2'-Azinobis(3-ethylbenzthiazoline-6-sulfonic acid (ABTS, Moss, Cat. No. ABST).
19. 10% SDS.

Procedure:
1. Coat Corning 96-well ELISA plates with 2 µg of polyEY peptide in sterile PBS as described in step 3 of Materials and Reagents.
2. Remove unbound liquid from wells by inverting plate. Wash once with TBST. Pat the plate on a paper towel to remove excess liquid.
3. Add 100 µl of 1% BSA in PBS to each well. Incubate, with shaking, for 1 hr. at room temperature.
4. Repeat step 2.
5. Soak wells with 50 mM HEPES (pH7.5) (150 µl/well).
6. Dilute test compound with $dH_2O$/4% DMSO to 4 times the desired final assay concentration in 96-well polypropylene plates.
7. Add 25 µl diluted test compound to ELISA plate. In control wells, place 25 µl of $dH_2O$/4% DMSO.
8. Add 25 µl of 40 mM $MnCl_2$ with 4×ATP (2 µM) to each well.
9. Add 25 µl 0.5M EDTA to negative control wells.
10. Dilute GST-Flk1 to 0.005 µg (5 ng)/well with KDB.
11. Add 50 µl of diluted enzyme to each well.
12. Incubate, with shaking, for 15 minutes at room temperature.
13. Stop reaction by adding 50 µl of 250 mM EDTA (pH 8.0).
14. Wash 3× with TBST and pat plate on paper towel to remove excess liquid.
15. Add 100 µl per well anti-phosphotyrosine HRP conjugate, 1:5,000 dilution in antibody dilution buffer. Incubate, with shaking, for 90 min. at room temperature.
16. Wash as in step 14.
17. Add 100 µl of room temperature ABTS solution to each well.
18. Incubate, with shaking, for 10 to 15 minutes. Remove any bubbles.
19. Stop reaction by adding 20 µl of 10% SDS to each well.
20. Read results on Dynatech MR7000 ELISA reader with test filter at 410 nM and reference filter at 630 nM.

Pyk2 Bioassay

This assay is used to measure the in vitro kinase activity of HA epitope-tagged full length pyk2 (FL.pyk2-HA) in an ELISA assay.

Materials and Reagents:
1. Corning 96-well Elisa plates.
2. 12CA5 monoclonal anti-HA antibody (SUGEN, Inc.)
3. PBS (Dulbecco's Phosphate-Buffered Saline (Gibco Catalog #450-1300EB)
4. TBST Buffer: for 1 L, mix 8.766 g NaCl, 6.057 g TRIS and 1 ml of 0.1% Triton X-100 in approx. 900 ml $dH_2O$. Adjust pH to 7.2, bring volume to 1 L.
5. Blocking Buffer: for 1 L, mix 100 g 10% BSA, 12.1 g 100 mM TRIS, 58.44 g 1M NaCl and 10 mL of 1% TWEEN-20.
6. FL.pyk2-HA from sf9 cell lysates (SUGEN, Inc.).
7. 4% DMSO in MilliQue $H_2O$.
8. 10 mM ATP in $dH_2O$.
9. 1M $MnCl_2$.
10. 1M $MgCl_2$.
11. 1M Dithiothreitol (DTT).
12. 10×Kinase buffer phosphorylation: mix 5.0 ml 1M Hepes (pH 7.5), 0.2 ml 1M $MnCl_2$, 1.0 ml 1 M $MgCl_2$, 1.0 ml 10% Triton X-100 in 2.8 ml $dH_2O$. Just prior to use, add 0.1 ml 1M DTT.
13. NUNC 96-well V bottom polypropylene plates.
14. 500 mM EDTA in $dH_2O$.
15. Antibody dilution buffer: for 100 mL, 1 mL 5% BSA/PBS and 1 mL 10% Tween-20 in 88 mL TBS.
16. HRP-conjugated anti-Ptyr PY99), Santa Cruz Biotech Cat. No. SC-7020.
17. ABTS, Moss, Cat. No. ABST-2000.
18. 10% SDS.

Procedure:
1. Coat Corning 96 well ELISA plates with 0.5 µg per well 12CA5 anti-HA antibody in 100 ul PBS. Store overnight at 4° C.
2. Remove unbound HA antibody from wells by inverting plate. Wash plate with $dH_2O$. Pat the plate on a paper towel to remove excess liquid.
3. Add 150 µl Blocking Buffer to each well. Incubate, with shaking, for 30 min at room temperature.
4. Wash plate 4× with TBS-T.
5. Dilute lysate in PBS (1.5 µg lysate/100 µl PBS).
6. Add 100 µl of diluted lysate to each well. Shake at room temperature for 1 hr.
7. Wash as in step 4.
8. Add 50 µl of 2× kinase Buffer to ELISA plate containing captured pyk2-HA.
9. Add 25 µL of 400 µM test compound in 4% DMSO to each well. For control wells use 4% DMSO alone.
10. Add 25 µL of 0.5 M EDTA to negative control wells.
11. Add 25 µl of 20 µM ATP to all wells. Incubate, with shaking, for 10 minutes.
12. Stop reaction by adding 25 µl 500 mM EDTA (pH 8.0) to all wells.
13. Wash as in step 4.
14. Add 100 µL HRP conjugated anti-Ptyr diluted 1:6000 in Antibody Dilution Buffer to each well. Incubate, with shaking, for 1 hr. at room temperature.
15. Wash plate 3× with TBST and 1× with PBS.
16. Add 100 µL of ABST solution to each well.
17. If necessary, stop the development reaction by adding 20 µL 10% SDS to each well.
18. Read plate on ELISA reader with test filter at 410 nM and reference filter at 630 nM.

FGFR1 Bioassay

This assay is used to measure the in vitro kinase activity of FGF1-R in an ELISA assay.

Materials and Reagents:
1. Costar 96-well Elisa plates (Corning Catalog #3369).
2. Poly(Glu-Tyr) (Sigma Catalog #P0275).
3. PBS (Gibco Catalog #450-1300EB)
4. 50 mM Hepes Buffer Solution.
5. Blocking Buffer (5% BSA/PBS).
6. Purified GST-FGFR1 (SUGEN, Inc.)
7. Kinase Dilution Buffer.
   Mix 500 µl 1M Hepes (GIBCO), 20 µl 5% BSA/PBS, 10 µl 100 mM sodium orthovanadate and 50 µl 5M NaCl.
8. 10 mM ATP
9. ATP/$MnCl_2$ phosphorylation mix: mix 20 µL ATP, 400 µL 1M $MnCl_2$ and 9.56 ml $dH_2O$.

10. NUNC 96-well V bottom polypropylene plates (Applied Scientific Catalog #AS-72092).
11. 0.5M EDTA.
12. 0.05% TBST
    Add 500 μL TWEEN to 1 liter TBS.
13. Rabbit polyclonal anti-phosphotyrosine serum (SUGEN, Inc.).
14. Goat anti-rabbit IgG peroxidase conjugate (Biosource, Catalog #ALI0404).
15. ABTS Solution.
16. ABTS/$H_2O_2$ solution.

Procedure:
1. Coat Costar 96 well ELISA plates with 1 μg per well Poly(Glu,Tyr) in 100 μl PBS. Store overnight at 4° C.
2. Wash coated plates once with PBS.
3. Add 150 μL of 5% BSA/PBS Blocking Buffer to each well. Incubate, with shaking, for 1 hr. room temperature.
4. Wash plate 2× with PBS, then once with 50 mM Hepes. Pat plates on a paper towel to remove excess liquid and bubbles.
5. Add 25 μL of 0.4 mM test compound in 4% DMSO or 4% DMSO alone (controls) to plate.
6. Dilute purified GST-FGFR1 in Kinase Dilution Buffer (5 ng kinase/50 μl KDB/well).
7. Add 50 μL of diluted kinase to each well.
8. Start kinase reaction by adding 25 μl/well of freshly prepared ATP/Mn++ (0.4 ml 1M $MnCl_2$, 40 μL 10 mm ATP, 9.56 ml $dH_2O$), freshly prepared).
9. This is a fast kinase reaction and must be stopped with 25 μL of 0.5M EDTA in a manner similar to the addition of ATP.
10. Wash plate 4× with fresh TBST.
11. Make up Antibody Dilution Buffer: Per 50 ml:
    Mix 5 ml of 5% BSA, 250 μl of 5% milk and 50 μl of 100 mM sodium vanadate, bring to final volume with 0.05% TBST.
12. Add 100 μl per well of anti-phosphotyrosine (1:10000 dilution in ADB). Incubate, with shaking for 1 hr. at room temperature.
13. Wash as in step 10.
14. Add 100 μl per well of Biosource Goat anti-rabbit IgG peroxidase conjugate (1:6000 dilution in ADB). Incubate, with shaking for 1 hr. at room temperature.
15. Wash as in step 10 and then with PBS to remove bubbles and excess TWEEN.
16. Add 100 μl of ABTS/$H_2O_2$ solution to each well.
17. Incubate, with shaking, for 10 to 20 minutes. Remove any bubbles.
18. Read assay on Dynatech MR7000 elisa reader: test filter at 410 nM, reference filtrate 630 nM.

EGFR Bioassay

This assay is used to the in vitro kinase activity of FGF1-R in an ELISA assay.

Materials and Reagents:
1. Corning 96-well Elisa plates.
2. SUMO1 monoclonal anti-EGFR antibody (SUGEN, Inc.).
3. PBS
4. TBST Buffer
5. Blocking Buffer: for 100 ml, mix 5.0 g Carnation Instant Non-fat Milk® with 100 ml of PBS.
6. A431 cell lysate (SUGEN, Inc.).
7. TBS Buffer:

8. TBS+10% DMSO: for 1 L, mix 1.514 g TRIS, 2.192 g NaCl and 25 ml DMSO; bring to 1 liter total volume with $dH_2O$.
9. ATP (Adenosine-5'-triphosphate, from Equine muscle, Sigma Cat. No. A-5394), 1.0 mM solution in $dH_2O$. This reagent should be made up immediately prior to use and kept on ice.
10. 1.0 mM $MnCl_2$.
11. ATP/$MnCl_2$ phosphorylation mix: to make 10 ml, mix 300 μl of 1 mM ATP, 500 μl $MnCl_2$ and 9.2 ml $dH_2O$. Prepare just prior to use, keep on ice.
12. NUNC 96-well V bottom polypropylene plates.
13. EDTA.
14. Rabbit polyclonal anti-phosphotyrosine serum (SUGEN, Inc.).
15. Goat anti-rabbit IgG peroxidase conjugate (Biosource Cat. No. ALI0404).
16. ABTS.
17. 30% Hydrogen peroxide.
18. ABTS/$H_2O_2$.
19. 0.2 M HCl.

Procedure:
1. Coat Corning 96 well ELISA plates with 0.5 μg SUMO1 in 100 μl PBS per well, store overnight at 4° C.
2. Remove unbound SUMO1 from wells by inverting plate to remove liquid. Wash 1× with $dH_2O$. Pat the plate on a paper towel to remove excess liquid.
3. Add 150 μl of Blocking Buffer to each well. Incubate, with shaking, for 30 min. at room temperature.
4. Wash plate 3× with deionized water, then once with TBST. Pat plate on a paper towel to remove excess liquid and bubbles.
5. Dilute lysate in PBS (7 μg lysate/100 μl PBS)
6. Add 100 μl of diluted lysate to each well. Shake at room temperature for 1 hr.
7. Wash plates as in 4, above.
8. Add 120 μl TBS to ELISA plate containing captured EGFR.
9. Dilute test compound 1:10 in TBS, place in well
10. Add 13.5 μl diluted test compound to ELISA plate. To control wells, add 13.5 μl TBS in 10% DMSO.
11. Incubate, with shaking, for 30 minutes at room temperature.
12. Add 15 μl phosphorylation mix to all wells except negative control well. Final well volume should be approximately 150 μl with 3 μM ATP/5 mM $MnCl_2$ final concentration in each well. Incubate with shaking for 5 minutes.
13. Stop reaction by adding 16.5 μl of EDTA solution while shaking. Shake for additional 1 min.
14. Wash 4× with deionized water, 2× with TBST.
15. Add 100 μl anti-phosphotyrosine (1:3000 dilution in TBST) per well. Incubate, with shaking, for 30–45 min. at room temperature.
16. Wash as in 4, above.
17. Add 100 μl Biosource Goat anti-rabbit IgG peroxidase conjugate (1:2000 dilution in TBST) to each well. Incubate with shaking for 30 min. at room temperature.
18. Wash as in 4, above.
19. Add 100 μl of ABTS/$H_2O_2$ solution to each well.
20. Incubate 5 to 10 minutes with shaking. Remove any bubbles.
21. If necessary, stop reaction by adding 100 μl 0.2 M HCl per well.

22. Read assay on Dynatech MR7000 ELISA reader: test filter at 410 nM, reference filter at 630 nM.

PDGFR Bioassay

This assay is used to the in vitro kinase activity of FGF1-R in an ELISA assay.

Materials and Reagents:
1. Corning 96-well Elisa plates
2. 28D4C10 monoclonal anti-PDGFR antibody (SUGEN, Inc.).
3. PBS.
4. TBST Buffer.
5. Blocking Buffer (same as for EGFR bioassay).
6. PDGFR-β expressing NIH 3T3 cell lysate (SUGEN, Inc.).
7. TBS Buffer.
8. TBS+10% DMSO.
9. ATP.
10. $MnCl_2$.
11. Kinase buffer phosphorylation mix: for 10 ml, mix 250 µl 1M TRIS, 200 µl 5M NaCl, 100 µl 1M $MnCl_2$ and 50 µl 100 mM Triton X-100 in enough $dH_2O$ to make 10 ml.
12. NUNC 96-well V bottom polypropylene plates.
13. EDTA.
14. Rabbit polyclonal anti-phosphotyrosine serum (SUGEN, Inc.).
15. Goat anti-rabbit IgG peroxidase conjugate (Biosource Cat. No. ALI0404).
16. ABTS.
17. Hydrogen peroxide, 30% solution.
18. $ABTS/H_2O_2$.
19. 0.2 M HCl.

Procedure:
1. Coat Corning 96 well ELISA plates with 0.5 µg 28D4C10 in 100 µl PBS per well, store overnight at 4° C.
2. Remove unbound 28D4C10 from wells by inverting plate to remove liquid. Wash 1× with $dH_2O$. Pat the plate on a paper towel to remove excess liquid.
3. Add 150 µl of Blocking Buffer to each well. Incubate for 30 min. at room temperature with shaking.
4. Wash plate 3× with deionized water, then once with TBST. Pat plate on a paper towel to remove excess liquid and bubbles.
5. Dilute lysate in HNTG (10 µg lysate/100 µl HNTG).
6. Add 100 µl of diluted lysate to each well. Shake at room temperature for 60 min.
7. Wash plates as described in Step 4.
8. Add 80 µl working kinase buffer mix to ELISA plate containing captured PDGFR.
9. Dilute test compound 1:10 in TBS in 96-well polypropylene plates.
10. Add 10 µl diluted test compound to ELISA plate. To control wells, add 10 µl TBS+10% DMSO. Incubate with shaking for 30 minutes at room temperature.
11. Add 10 µl ATP directly to all wells except negative control well (final well volume should be approximately 100 µl with 20 µM ATP in each well.) Incubate 30 minutes with shaking.
12. Stop reaction by adding 10 µl of EDTA solution to each well.
13. Wash 4× with deionized water, twice with TBST.
14. Add 100 µl anti-phosphotyrosine (1:3000 dilution in TBST) per well. Incubate with shaking for 30–45 min. at room temperature.
15. Wash as in Step 4.
16. Add 100 µl Biosource Goat anti-rabbit IgG peroxidase conjugate (1:2000 dilution in TBST) to each well. Incubate with shaking for 30 min. at room temperature.
17. Wash as in Step 4.
18. Add 100 µl of $ABTS/H_2O_2$ solution to each well.
19. Incubate 10 to 30 minutes with shaking. Remove any bubbles.
20. If necessary stop reaction with the addition of 100 µl 0.2 M HCl per well.
21. Read assay on Dynatech MR7000 ELISA reader with test filter at 410 nM and reference filter at 630 nM.

Cellular HER-2 Kinase Assay

This assay is used to measure HER-2 kinase activity in whole cells in an ELISA format.

Materials and Reagents:
1. DMEM (GIBCO Catalog #11965-092).
2. Fetal Bovine Serum (FBS, GIBCO Catalog #16000-044), heat inactivated in a water bath for 30 min. at 56° C.
3. Trypsin (GIBCO Catalog #25200-056).
4. L-Glutamine (GIBCO Catalog #25030-081)
5. HEPES (GIBCO Catalog #15630-080).
6. Growth Media
   Mix 500 ml DMEM, 55 ml heat inactivated FBS, 10 ml HEPES and 5.5 ml L-Glutamine.
7. Starve Media
   Mix 500 ml DMEM, 2.5 ml heat inactivated FBS, 10 ml HEPES and 5.5 ml L-Glutamine.
8. PBS.
9. Flat Bottom 96-well Tissue Culture Micro Titer Plates (Corning Catalog #25860).
10. 15 cm Tissue Culture Dishes (Corning Catalog #08757148).
11. Corning 96-well ELISA Plates.
12. NUNC 96-well V bottom polypropylene plates.
13. Costar Transfer Cartridges for the Transtar 96 (Costar Catalog #7610).
14. SUMO 1: monoclonal anti-EGFR antibody (SUGEN, Inc.).
15. TBST Buffer.
16. Blocking Buffer: 5% Carnation Instant Milk® in PBS.
17. EGF Ligand: EGF-201, Shinko American, Japan. Suspend powder in 100 uL of 10 mM HCl. Add 100 uL 10 mM NaOH. Add 800 uL PBS and transfer to an Eppendorf tube store at −20° C. until ready to use.
18. HNTG Lysis Buffer
    For Stock 5×HNTG, mix 23.83 g Hepes, 43.83 g NaCl, 500 ml glycerol and 100 ml Triton X-100 and enough $dH_2O$ to make 1 L of total solution. For 1×HNTG*, mix 2 ml HNTG, 100 µL 0.1M $Na_3VO_4$, 250 µL 0.2M $Na_4P_2O_7$ and 100 µL EDTA.
19. EDTA.
20. $Na_3VO_4$. To make stock solution, mix 1.84 g $Na_3VO_4$ with 90 ml $dH_2O$. Adjust pH to 10. Boil in microwave for one minute (solution becomes clear). Cool to room temperature. Adjust pH to 10. Repeat heating/cooling cycle until pH remains at 10.
21. 200 mM $Na_4P_2O_7$.
22. Rabbit polyclonal antiserum specific for phosphotyrosine (anti-Ptyr antibody, SUGEN, Inc.).
23. Affinity purified antiserum, goat anti-rabbit IgG antibody, peroxidase conjugate (Biosource Cat #ALI0404).

24. ABTS Solution.
25. 30% Hydrogen peroxide solution.
26. ABTS/$H_2O_2$.
27. 0.2 M HCl.

Procedure:
1. Coat Corning 96 well ELISA plates with SUMO1 at 1.0 ug per well in PBS, 100 ul final volume/well. Store overnight at 4° C.
2. On day of use, remove coating buffer and wash plate 3 times with d$H_2$O and once with TBST buffer. All washes in this assay should be done in this manner, unless otherwise specified.
3. Add 100 ul of Blocking Buffer to each well. Incubate plate, with shaking, for 30 min. at room temperature. Just prior to use, wash plate.
4. Use EGFr/HER-2 chimera/3T3-C7 cell line for this assay.
5. Choose dishes having 80–90% confluence. Collect cells by trypsinization and centrifuge at 1000 rpm at room temperature for 5 min.
6. Resuspend cells in starve medium and count with trypan blue. Viability above 90% is required. Seed cells in starve medium at a density of 2,500 cells per well, 90 ul per well, in a 96 well microtiter plate. Incubate seeded cells overnight at 37° under 5% $CO_2$.
7. Start the assay two days after seeding.
8. Test compounds are dissolved in 4% DMSO. Samples are then further diluted directly on plates with starve-DMEM. Typically, this dilution will be 1:10 or greater. All wells are then transferred to the cell plate at a further 1:10 dilution (10 µl sample and media into 90 µl of starve media. The final DMSO concentration should be 1% or lower. A standard serial dilution may also be used.
9. Incubate under 5% $CO_2$ at 37° C. for 2 hours.
10. Prepare EGF ligand by diluting stock EGF (16.5 uM) in warm DMEM to 150 nM.
11. Prepare fresh HNTG* sufficient for 100 ul per well; place on ice.
12. After 2 hour incubation with test compound, add prepared EGF ligand to cells, 50 ul per well, for a final concentration of 50 nM. Positive control wells receive the same amount of EGF. Negative controls do not receive EGF. Incubate at 37° C. for 10 min.
13. Remove test compound, EGF, and DMEM. Wash cells once with PBS.
14. Transfer HNTG* to cells, 100 ul per well. Place on ice for 5 minutes. Meanwhile, remove blocking buffer from ELISA plate and wash.
15. Scrape cells from plate with a micropipettor and homogenize cell material by repeatedly aspirating and dispensing the HNTG* lysis buffer. Transfer lysate to a coated, blocked, washed ELISA plate. Or, use a Costar transfer cartridge to transfer lysate to the plate.
16. Incubate, with shaking, at room temperature for 1 hr.
17. Remove lysate, wash. Transfer freshly diluted anti-Ptyr antibody (1:3000 in TBST) to ELISA plate, 100 ul per well.
18. Incubate, with shaking, at room temperature, for 30 min.
19. Remove anti-Ptyr antibody, wash. Transfer freshly diluted BIOSOURCE antibody to ELISA plate (1:8000 in TBST, 100 ul per well).
20. Incubate, with shaking, at room temperature for 30 min.
21. Remove BIOSOURCE antibody, wash. Transfer freshly prepared ABTS/$H_2O_2$ solution to ELISA plate, 100 ul per well.
22. Incubate, with shaking, for 5–10 minutes. Remove any bubbles.
23. Stop reaction with the addition of 100 ul of 0.2M HCl per well.
24. Read assay on Dynatech MR7000 ELISA reader with test filter set at 410 nM and reference filter at 630 nM.

CDK2/Cyclin A Assay

This assay is used to measure the in vitro serine/threonine kinase activity of human cdk2/cyclin A in a Scintillation Proximity Assay (SPA).

Materials and Reagents.
1. Wallac 96-well polyethylene terephthalate (flexi) plates (Wallac Catalog #1450-401).
2. Amersham Redivue [$\gamma^{33}$P]ATP (Amersham catalog #AH 9968).
3. Amersham streptavidin coated polyvinyltoluene SPA beads (Amersham catalog #RPNQ0007). The beads should be reconstituted in PBS without magnesium or calcium, at 20 mg/ml.
4. Activated cdk2/cyclin A enzyme complex purified from Sf9 cells (SUGEN, Inc.).
5. Biotinylated peptide substrate (Debtide). Peptide biotin-X-PKTPKKAKKL is dissolved in d$H_2$O at a concentration of 5 mg/ml.
6. Peptide/ATP Mixture: for 10 ml, mix 9.979 ml d$H_2$O, 0.00125 ml "cold" ATP, 0.010 ml Debtide and 0.010 ml $\gamma^{33}$P ATP. The ultimate concentration per well will be 0.5 µM "cold" ATP, 0.1 µg Debtide and 0.2 µCi $\gamma^{33}$P ATP.
7. Kinase buffer: for 10 ml, mix 8.85 ml d$H_2$O, 0.625 ml TRIS (pH 7.4), 0.25 ml 1M $MgCl_2$, 0.25 ml 10% NP40 and 0.025 ml 1M DTT, added fresh just prior to use.
8. 10 mM ATP in d$H_2$O.
9. 1M Tris, pH adjusted to 7.4 with HCl.
10. 1M $MgCl_2$.
11. 1M DTT.
12. PBS (Gibco Catalog #14190-144).
13. 0.5M EDTA.
14. Stop solution: For 10 ml, mix 9.25 ml PBS, 0.005 ml 100 mM ATP, 0.1 ml 0.5 M EDTA, 0.1 ml 10% Triton X-100 and 1.25 ml of 20 mg/ml SPA beads.

Procedure:
1. Prepare solutions of test compounds at 5× the desired final concentration in 5% DMSO. Add 10 ul to each well. For negative controls, use 10 ul 5% DMSO alone in wells.
2. Dilute 5 µl of cdk2/cyclin A solution with 2.1 ml 2×kinase buffer.
3. Add 20 ul enzyme to each well.
4. Add 10 µL of 0.5 M EDTA to the negative control wells.
5. To start kinase reaction, add 20 µL of peptide/ATP mixture to each well. Incubate for 1 hr. without shaking.
6. Add 200 µl stop solution to each well.
7. Hold at least 10 min.
8. Spin plate at approx. 2300 rpm for 3–5 min.
9. Count plate using Trilux or similar reader.

MET Transphosphorylation Assay

This assay is used to measure phosphotyrosine levels on a poly(glutamic acid:tyrosine (4:1)) substrate as a means for identifying agonists/antagonists of met transphosphorylation of the substrate.

Materials and Reagents:
1. Corning 96-well Elisa plates, Corning Catalog #25805-96.
2. Poly(glu, tyr) 4:1, Sigma, Cat. No; P 0275.
3. PBS, Gibco Catalog #450-1300EB
4. 50 mM HEPES
5. Blocking Buffer: Dissolve 25 g Bovine Serum Albumin, Sigma Cat. No A-7888, in 500 ml PBS, filter through a 4 μm filter.
6. Purified GST fusion protein containing the Met kinase domain, Sugen, Inc.
7. TBST Buffer.
8. 10% aqueous (MilliQue $H_2O$) DMSO.
9. 10 mM aqueous ($dH_2O$) Adenosine-5'-triphosphate, Sigma Cat. No. A-5394.
10. 2× Kinase Dilution Buffer: for 100 ml, mix 10 mL 1M HEPES at pH 7.5 with 0.4 mL 5% BSA/PBS, 0.2 mL 0.1 M sodium orthovanadate and 1 mL 5M sodium chloride in 88.4 mL $dH_2O$.
11. 4×ATP Reaction Mixture: for 10 mL, mix 0.4 mL 1 M manganese chloride and 0.02 mL 0.1 M ATP in 9.56 mL $dH_2O$.
12. 4× Negative Controls Mixture: for 10 mL, mix 0.4 mL 1 M manganese chloride in 9.6 mL $dH_2O$.
13. NUNC 96-well V bottom polypropylene plates, Applied Scientific Catalog #S-72092
14. 500 mM EDTA.
15. Antibody Dilution Buffer: for 100 mL, mix 10 mL 5% BSA/PBS, 0.5 mL 5% Carnation Instant Milk® in PBS and 0.1 mL 0.1 M sodium orthovanadate in 88.4 mL TBST.
16. Rabbit polyclonal antophosphotyrosine antibody, Sugen, Inc.
17. Goat anti-rabbit horseradish peroxidase conjugated antibody, Biosource, Inc.
18. ABTS Solution: for 1 L, mix 19.21 g citric acid, 35.49 g $Na_2HPO_4$ and 500 mg ABTS with sufficient $dH_2O$ to make 1 L.
19. ABTS/$H_2O_2$: mix 15 mL ABST solution with 2 μL $H_2O_2$ five minutes before use.
20. 0.2 M HCl Procedure:
1. Coat ELISA plates with 2 μg Poly(Glu-Tyr) in 100 μL PBS, store overnight at 4° C.
2. Block plate with 150 μL of 5% BSA/PBS for 60 min.
3. Wash plate twice with PBS, once with 50 mM Hepes buffer pH 7.4.
4. Add 50 μl of the diluted kinase to all wells. (Purified kinase is diluted with Kinase Dilution Buffer. Final concentration should be 10 ng/well.)
5. Add 25 μL of the test compound (in 4% DMSO) or DMSO alone (4% in $dH_2O$) for controls to plate.
6. Incubate the kinase/compound mixture for 15 minutes.
7. Add 25 μL of 40 mM $MnCl_2$ to the negative control wells.
8. Add 25 μL ATP/ $MnCl_2$ mixture to the all other wells (except the negative controls). Incubate for 5 min.
9. Add 25 μL 500 mM EDTA to stop reaction.
10. Wash plate 3× with TBST.
11. Add 100 μL rabbit polyclonal anti-Ptyr diluted 1:10,000 in Antibody Dilution Buffer to each well. Incubate, with shaking, at room temperature for one hour.
12. Wash plate 3× with TBST.
13. Dilute Biosource HRP conjugated anti-rabbit antibody 1:6,000 in Antibody Dilution buffer. Add 100 μL per well and incubate at room temperature, with shaking, for one hour.
14. Wash plate 1× with PBS.
15. Add 100 μl of ABTS/$H_2O_2$ solution to each well.
16. If necessary, stop the development reaction with the addition of 100 μl of 0.2M HCl per well.
17. Read plate on Dynatech MR7000 elisa reader with the test filter at 410 nM and the reference filter at 630 nM.

IGF-1 Transphosphorylation Assay

This assay is used to measure the phosphotyrosine level in poly(glutamic acid:tyrosine)(4:1) for the identification of agonists/antagonists of gst-IGF-1 transphosphorylation of a substrate.

Materials and Reagents:
1. Corning 96-well Elisa plates.
2. Poly (Glu-tyr) (4:1), Sigma Cat. No. P 0275.
3. PBS, Gibco Catalog #450-1300EB.
4. 50 mM HEPES
5. TBB Blocking Buffer: for 1 L, mix 100 g BSA, 12.1 gTRIS (pH 7.5), 58.44 g sodium chloride and 10 mL 1% TWEEN-20.
6. Purified GST fusion protein containing the IGF-1 kinase domain (Sugen, Inc.)
7. TBST Buffer: for 1 L, mix 6.057 g Tris, 8.766 g sodium chloride and 0.5 ml TWEEN-20 with enough $dH_2O$ to make 1 liter.
8. 4% DMSO in Milli-Q $H_2O$.
9. 10 mM ATP in $dH_2O$.
10. 2× Kinase Dilution Buffer: for 100 mL, mix 10 mL 1 M HEPES (pH 7.5), 0.4 mL 5% BSA in $dH_2O$, 0.2 mL 0.1 M sodium orthovanadate and 1 mL 5 M sodium chloride with enough $dH_2O$ to make 100 mL.
11. 4×ATP Reaction Mixture: for 10 mL, mix 0.4 mL 1 M $MnCl_2$ and 0.008 mL 0.01 M ATP and 9.56 mL $dH_2O$.
12. 4× Negative Controls Mixture: mix 0.4 mL 1 M manganese chloride in 9.60 mL $dH_2O$.
13. NUNC 96-well V bottom polypropylene plates.
14. 500 mM EDTA in $dH_2O$.
15. Antibody Dilution Buffer: for 100 mL, mix 10 mL 5% BSA in PBS, 0.5 mL 5% Carnation Instant Non-fat Milk® in PBS and 0.1 mL 0.1 M sodium orthovanadate in 88.4 mL TBST.
16. Rabbit Polyclonal antiphosphotyrosine antibody, Sugen, Inc.
17. Goat anti-rabbit HRP conjugated antibody, Biosource.
18. ABTS Solution.
20. ABTS/$H_2O_2$: mix 15 mL ABTS with 2 μL $H_2O_2$ 5 minutes before using.
21. 0.2 M HCl in $dH_2O$.

Procedure:
1. Coat ELISA plate with 2.0 μg/well Poly(Glu, Tyr) 4:1 (Sigma P0275) in 100 μl PBS. Store plate overnight at 4° C.
2. ash plate once with PBS.
3. Add 100 μl of TBB Blocking Buffer to each well. Incubate plate for 1 hour with shaking at room temperature.
4. Wash plate once with PBS, then twice with 50 mM Hepes buffer pH 7.5.
5. Add 25 μL of test compound in 4% DMSO (obtained by diluting a stock solution of 10 mM test compound in 100% DMSO with $dH_2O$) to plate.

6. Add 10.0 ng of gst-IGF-1 kinase in 50 µl Kinase Dilution Buffer) to all wells.
7. Start kinase reaction by adding 25 µl 4×ATP Reaction Mixture to all test wells and positive control wells. Add 25 µl 4× Negative Controls Mixture to all negative control wells. Incubates for 10 minutes with shaking at room temperature.
8. Add 25 µl 0.5M EDTA (pH 8.0) to all wells.
9. Wash plate 4× with TBST Buffer.
10. Add rabbit polyclonal anti-phosphotyrosine antisera at a dilution of 1:10,000 in 100 µl Antibody Dilution Buffer to all wells. Incubate, with shaking, at room temperature for 1 hour.
11. Wash plate as in step 9.
12. Add 100 µL Biosource anti-rabbit HRP at a dilution of 1:10,000 in Antibody dilution buffer to all wells. Incubate, with shaking, at room temperature for 1 hour.
13. Wash plate as in step 9, follow with one wash with PBS to reduce bubbles and excess Tween-20.
14. Develop by adding 100 µl/well ABTS/$H_2O_2$ to each well
15. After about 5 minutes, read on ELISA reader with test filter at 410 nm and referenced filter at 630 nm.

BRDU Incorporation Assays

The following assays use cells engineered to express a selected receptor and then evaluate the effect of a compound of interest on the activity of ligand-induced DNA synthesis by determining BrdU incorporation into the DNA.

The following materials, reagents and procedure are general to each of the following BrdU incorporation assays. Variances in specific assays are noted.

Materials and Reagents:
1. The appropriate ligand.
2. The appropriate engineered cells.
3. BrdU Labeling Reagent: 10 mM, in PBS (pH 7.4) (Boehringer Mannheim, Germany).
4. FixDenat: fixation solution (ready to use) (Boehringer Mannheim, Germany).
5. Anti-BrdU-POD: mouse monoclonal antibody conjugated with peroxidase (Boehringer Mannheim, Germany).
6. TMB Substrate Solution: tetramethylbenzidine (TMB, Boehringer Mannheim, Germany).
7. PBS Washing Solution : 1×PBS, pH 7.4.
8. Albumin, Bovine (BSA), fraction V powder (Sigma Chemical Co., USA).

General Procedure:
1. Cells are seeded at 8000 cells/well in 10% CS, 2 mM Gln in DMEM, in a 96 well plate. Cells are incubated overnight at 37° C. in 5% $CO_2$.
2. After 24 hours, the cells are washed with PBS, and then are serum-starved in serum free medium (0% CS DMEM with 0.1% BSA) for 24 hours.
3. On day 3, the appropriate ligand and the test compound are added to the cells simultaneously. The negative control wells receive serum free DMEM with 0.1% BSA only; the positive control cells receive the ligand but no test compound. Test compounds are prepared in serum free DMEM with ligand in a 96 well plate, and serially diluted for 7 test concentrations.
4. After 18 hours of ligand activation, diluted BrdU labeling reagent (1:100 in DMEM, 0.1% BSA) is added and the cells are incubated with BrdU (final concentration=10 µM) for 1.5 hours.
5. After incubation with labeling reagent, the medium is removed by decanting and tapping the inverted plate on a paper towel. FixDenat solution is added (50 µl/well) and the plates are incubated at room temperature for 45 minutes on a plate shaker.
6. The FixDenat solution is thoroughly removed by decanting and tapping the inverted plate on a paper towel. Milk is added (5% dehydrated milk in PBS, 200 µl/well) as a blocking solution and the plate is incubated for 30 minutes at room temperature on a plate shaker.
7. The blocking solution is removed by decanting and the wells are washed once with PBS. Anti-BrdU-POD solution (1:200 dilution in PBS, 1% BSA) is added (50 µl/well) and the plate is incubated for 90 minutes at room temperature on a plate shaker.
8. The antibody conjugate is thoroughly removed by decanting and rinsing the wells 5 times with PBS, and the plate is dried by inverting and tapping on a paper towel.
9. TMB substrate solution is added (100 µl/well) and incubated for 20 minutes at room temperature on a plate shaker until color development is sufficient for photometric detection.
10. The absorbance of the samples are measured at 410 nm (in "dual wavelength" mode with a filter reading at 490 nm, as a reference wavelength) on a Dynatech ELISA plate reader.

EGF-Induced BrdU Incorporation Assay

Materials and Reagents:
1. Mouse EGF, 201 (Toyobo Co., Ltd., Japan).
2. 3T3/EGFRc7.

EGF-Induced Her-2-driven BrdU Incorporation Assay

Materials and Reagents:
1. Mouse EGF, 201 (Toyobo Co., Ltd., Japan).
2. 3T3/EGFr/Her2/EGFr (EGFr with a Her-2 kinase domain).

EGF-Induced Her-4-driven BrdU Incorporation Assay

Materials and Reagents:
1. Mouse EGF, 201 (Toyobo Co., Ltd., Japan).
2. 3T3/EGFr/Her4/EGFr (EGFr with a Her-4 kinase domain).

PDGF-Induced BrdU Incorporation Assay

Materials and Reagents:
1. Human PDGF B/B (Boehringer Mannheim, Germany).
2. 3T3/EGFRc7.

FGF-Induced BrdU Incorporation Assay

Materials and Reagents:
1. Human FGF2/bFGF (Gibco BRL, USA).
2. 3T3c7/EGFr

IGF1-Induced BrdU Incorporation Assay

Materials and Reagents:
1. Human, recombinant (G511, Promega Corp., USA)
2. 3T3/IGF1r.

Insulin-Induced BrdU Incorporation Assay

Materials and Reagents:
1. Insulin, crystalline, bovine, Zinc (13007, Gibco BRL, USA).
2. 3T3/H25.

HGF-Induced BrdU Incorporation Assay

Materials and Reagents:
1. Recombinant human HGF (Cat. No. 249-HG, R&D Systems, Inc. USA).
2. BxPC-3 cells (ATCC CRL-1687).

Procedure:
1. Cells are seeded at 9000 cells/well in RPMI 10% FBS in a 96 well plate. Cells are incubated overnight at 37° C. in 5% $CO_2$.
2. After 24 hours, the cells are washed with PBS, and then are serum starved in 100 µl serum-free medium (RPMI with 0.1% BSA) for 24 hours.
3. On day 3, 25 µl containing ligand (prepared at 1 µg/ml in RPMI with 0.1% BSA; final HGF conc. is 200 ng/ml) and test compounds are added to the cells. The negative control wells receive 25 µl serum-free RPMI with 0.1% BSA only; the positive control cells receive the ligand (HGF) but no test compound. Test compounds are prepared at 5 times their final concentration in serum-free RPMI with ligand in a 96 well plate, and serially diluted to give 7 test concentrations. Typically, the highest final concentration of test compound is 100 µM, and 1:3 dilutions are used (i.e. final test compound concentration range is 0.137–100 µM).
4. After 18 hours of ligand activation, 12.5 µl of diluted BrdU labeling reagent (1:100 in RPMI, 0.1% BSA) is added to each well and the cells are incubated with BrdU (final concentration is 10 µM) for 1 hour.
5. Same as General Procedure.
6. Same as General Procedure.
7. The blocking solution is removed by decanting and the wells are washed once with PBS. Anti-BrdU-POD solution (1:100 dilution in PBS, 1% BSA) is added (100 µl/well) and the plate is incubated for 90 minutes at room temperature on a plate shaker.
8. Same as General Procedure.
9. Same as General Procedure.
10. Same as General Procedure.

HUV-EC-C Assay

This assay is used to measure a compound's activity against PDGF-R, FGF-R, VEGF, aFGF or Flk-1/KDR, all of which are naturally expressed by HUV-EC cells.

Day 0
1. Wash and trypsinize HUV-EC-C cells (human umbilical vein endothelial cells, (American Type Culture Collection, catalogue no. 1730 CRL). Wash with Dulbecco's phosphate-buffered saline (D-PBS, obtained from Gibco BRL, catalogue no. 14190-029) 2 times at about 1 ml/10 cm² of tissue culture flask. Trypsinize with 0.05% trypsin-EDTA in non-enzymatic cell dissociation solution (Sigma Chemical Company, catalogue no. C-1544). The 0.05% trypsin is made by diluting 0.25% trypsin/1 mM EDTA (Gibco, catalogue no. 25200-049) in the cell dissociation solution. Trypsinize with about 1 ml/25–30 cm² of tissue culture flask for about 5 minutes at 37° C. After cells have detached from the flask, add an equal volume of assay medium and transfer to a 50 ml sterile centrifuge tube (Fisher Scientific, catalogue no. 05-539-6).
2. Wash the cells with about 35 ml assay medium in the 50 ml sterile centrifuge tube by adding the assay medium, centrifuge for 10 minutes at approximately 200×g, aspirate the supernatant, and resuspend with 35 ml D-PBS. Repeat the wash two more times with D-PBS, resuspend the cells in about 1 ml assay medium/15 cm² of tissue culture flask. Assay medium consists of F12K medium (Gibco BRL, catalogue no. 21127-014) and 0.5% heat-inactivated fetal bovine serum. Count the cells with a Coulter Counter® (Coulter Electronics, Inc.) and add assay medium to the cells to obtain a concentration of $0.8-1.0 \times 10^5$ cells/ml.
3. Add cells to 96-well flat-bottom plates at 100 µl/well or $0.8-1.0 \times 10^4$ cells/well, incubate ~24 h at 37° C., 5% $CO_2$.

Day 1
1. Make up two-fold test compound titrations in separate 96-well plates, generally 50 µM on down to 0 µM. Use the same assay medium as mentioned in day 0, step 2 above. Titrations are made by adding 90 µl/well of test compound at 200 µM (4× the final well concentration) to the top well of a particular plate column. Since the stock test compound is usually 20 mM in DMSO, the 200 µM drug concentration contains 2% DMSO.

A diluent made up to 2% DMSO in assay medium (F12K+0.5% fetal bovine serum) is used as diluent for the test compound titrations in order to dilute the test compound but keep the DMSO concentration constant. Add this diluent to the remaining wells in the column at 60 µl/well. Take 60 µl from the 120 µl of 200 µM test compound dilution in the top well of the column and mix with the 60 µl in the second well of the column. Take 60 µl from this well and mix with the 60 µl in the third well of the column, and so on until two-fold titrations are completed. When the next-to-the-last well is mixed, take 60 µl of the 120 µl in this well and discard it. Leave the last well with 60 µl of DMSO/media diluent as a non-test compound-containing control. Make 9 columns of titrated test compound, enough for triplicate wells each for: (1) VEGF (obtained from Pepro Tech Inc., catalogue no. 100-200, (2) endothelial cell growth factor (ECGF) (also known as acidic fibroblast growth factor, or aFGF) (obtained from Boehringer Mannheim Biochemica, catalogue no. 1439 600), or, (3) human PDGF B/B (1276-956, Boehringer Mannheim, Germany) and assay media control. ECGF comes as a preparation with sodium heparin.

2. Transfer 50 µl/well of the test compound dilutions to the 96-well assay plates containing the $8-1.0 \times 10^4$ cells/100 µl/well of the HUV-EC-C cells from day 0 and incubate ~2 h at 37° C., 5% $CO_2$.

3. In triplicate, add 50 µl/well of 80 µg/ml VEGF, 20 ng/ml ECGF, or media control to each test compound condition. As with the test compounds, the growth factor concentrations are 4× the desired final concentration. Use the assay media from day 0 step 2 to make the concentrations of growth factors. Incubate approximately 24 hours at 37° C., 5% $CO_2$. Each well will have 50 µl test compound dilution, 50 µl growth factor or media, and 100 µl cells, which calculates to 200 µl/well total. Thus the 4× concentrations of test compound and growth factors become 1× once everything has been added to the wells.

Day 2
1. Add $^3$H-thymidine (Amersham, catalogue no. TRK-686) at 1 µCi/well (10 µl/well of 100 µCi/ml solution made up in RPMI media+10% heat-inactivated fetal bovine serum) and incubate ~24 h at 37° C., 5% $CO_2$. RPMI is obtained from Gibco BRL, catalogue no. 11875-051.

Day 3
1. Freeze plates overnight at −20° C.

Day 4

Thaw plates and harvest with a 96-well plate harvester (Tomtec Harvester 96®) onto filter mats (Wallac, catalogue no. 1205-401), read counts on a Wallac Betaplate™ liquid scintillation counter.

In Vivo Animal Models

Xenograft Animals Models

The ability of human tumors to grow as xenografts in athymic mice (e.g., Balb/c, nu/nu) provides a useful in vivo model for studying the biological response to therapies for human tumors. Since the first successful xenotransplantation of human tumors into athymic mice, (Rygaard and Povlsen, 1969, *Acta Pathol. Microbial. Scand.* 77:758–760), many different human tumor cell lines (e.g., mammary, lung, genitourinary, gastro-intestinal, head and neck, glioblastoma, bone, and malignant melanomas) have been transplanted and successfully grown in nude mice. The following assays may be used to determine the level of activity, specificity and effect of the different compounds of the present invention. Three general types of assays are useful for evaluating compounds: cellular/catalytic, cellular/biological and in vivo. The object of the cellular/catalytic assays is to determine the effect of a compound on the ability of a TK to phosphorylate tyrosines on a known substrate in a cell. The object of the cellular/biological assays is to determine the effect of a compound on the biological response stimulated by a TK in a cell. The object of the in vivo assays is to determine the effect of a compound in an animal model of a particular disorder such as cancer.

Suitable cell lines for subcutaneous xenograft experiments include C6 cells (glioma, ATCC #CCL 107), A375 cells (melanoma, ATCC #CRL 1619), A431 cells (epidermoid carcinoma, ATCC #CRL 1555), Calu 6 cells (lung, ATCC #HTB 56), PC3 cells (prostate, ATCC #CRL 1435), SKOV3TP5 cells and NIH 3T3 fibroblasts genetically engineered to overexpress EGFR, PDGFR, IGF-1R or any other test kinase. The following protocol can be used to perform xenograft experiments:

Female athymic mice (BALB/c, nu/nu) are obtained from Simonsen Laboratories (Gilroy, Calif.). All animals are maintained under clean-room conditions in Micro-isolator cages with Alpha-dri bedding. They receive sterile rodent chow and water ad libitum.

Cell lines are grown in appropriate medium (for example, MEM, DMEM, Ham's F10, or Ham's F12 plus 5%–10% fetal bovine serum (FBS) and 2 mM glutamine (GLN)). All cell culture media, glutamine, and fetal bovine serum are purchased from Gibco Life Technologies (Grand Island, N.Y.) unless otherwise specified. All cells are grown in a humid atmosphere of 90–95% air and 5–10% $CO_2$ at 37° C. All cell lines are routinely subcultured twice a week and are negative for mycoplasma as determined by the Mycotect method (Gibco).

Cells are harvested at or near confluency with 0.05% Trypsin-EDTA and pelleted at 450×g for 10 min. Pellets are resuspended in sterile PBS-or media (without FBS) to a particular concentration and the cells are implanted into the hindflank of the mice (8–10 mice per group, $2–10\times10^6$ cells/animal). Tumor growth is measured over 3 to 6 weeks using venier calipers. Tumor volumes are calculated as a product of length×width×height unless otherwise indicated. P values are calculated using the Students t-test. Test compounds in 50–100 μL excipient (DMSO, or VPD:D5W) can be delivered by IP injection at different concentrations generally starting at day one after implantation.

Tumor Invasion Model

The following tumor invasion model has been developed and may be used for the evaluation of therapeutic value and efficacy of the compounds identified to selectively inhibit KDR/FLK-1 receptor.

Procedure 8 week old nude mice (female) (Simonsen Inc.) are used as experimental animals. Implantation of tumor cells can be performed in a laminar flow hood. For anesthesia, Xylazine/Ketamine Cocktail (100 mg/kg ketamine and 5 mg/kg Xylazine) are administered intraperitoneally. A midline incision is done to expose the abdominal cavity (approximately 1.5 cm in length) to inject $10^7$ tumor cells in a volume of 100 μl medium. The cells are injected either into the duodenal lobe of the pancreas or under the serosa of the colon. The peritoneum and muscles are closed with a 6-0 silk continuous suture and the skin is closed by using wound clips. Animals are observed daily.

Analysis

After 2–6 weeks, depending on gross observations of the animals, the mice are sacrificed, and the local tumor metastases to various organs (lung, liver, brain, stomach, spleen, heart, muscle) are excised and analyzed (measurement of tumor size, grade of invasion, immunochemistry, in situ hybridization determination, etc.).

C-Kit Assay

This assay is used to detect the level of c-kit tyrosine phosphorylation.

MO7E (human acute myeloid leukemia) cells are serum starved overnight in 0.1% serum. Cells are pre-treated with the compound (concurrent with serum starvation), prior to ligand stimulation. Cells are stimulated with 250 ng/ml rh-SCF for 15 minutes. Following stimulation, cells were lysed and immunoprecipitated with an anti-c-kit antibody. Phosphotyrosine and protein levels were determined by Western blotting.

MTT Proliferation Assay

MO7E cells are serum starved and pre-treated with compound as described for the phosphorylation experiments. Cells are plated @ $4\times10^5$ cells/well in a 96 well dish, in 100 μl RPMI+10% serum. rh-SCF (100 ng/mL) is added and the plate is incubated for 48 hours. After 48 hours, 10 μl of 5 mg/ml MTT [3-(4,5-dimethythiazol-2-yl)-2,5-diphenyl tetrazolium bromide) is added and allowed to incubate for 4 hours. Acid isopropanol (100 μl of 0.04N HCl in isopropanol) is added and the optical density was measured at a wavelength of 550 nm.

Apoptosis Assay

MO7E cells are incubated +/−SCF and +/−compound in 10% FBS with rh-GM-CSF(10 ng/mL) and rh-IL-3 (10 ng/mL). Samples are assayed at 24 and 48 hours. To measure activated caspase-3, samples are washed with PBS and permeabilized with ice-cold 70% ethanol. The cells are then stained with PE-conjugated polyclonal rabbit anti-active caspase-3 and analyzed by FACS. To measure cleaved PARP, samples are lysed and analyzed by western blotting with an anti-PARP antibody.

Additional Assays

Additional assays which may be used to evaluate the compounds of this invention include, without limitation, a bio-flk-1 assay, an EGF receptor-HER2 chimeric receptor assay in whole cells, a bio-src assay, a bio-lck assay and an assay measuring the phosphorylation function of raf. The protocols for each of these assays may be found in U.S. application Ser. No. 09/099,842, which is incorporated by reference, including any drawings, herein.

Measurement of Cell Toxicity

Therapeutic compounds should be more potent in inhibiting receptor tyrosine kinase activity than in exerting a cytotoxic effect. A measure of the effectiveness and cell toxicity of a compound can be obtained by determining the therapeutic index, i.e., $IC_{50}/LD_{50}$. $IC_{50}$, the dose required to achieve 50% inhibition, can be measured using standard techniques such as those described herein. $LD_{50}$, the dosage which results in 50% toxicity, can also be measured by standard techniques as well (Mossman, 1983, *J. Immunol. Methods*, 65:55–63), by measuring the amount of LDH released (Korzeniewski and Callewaert, 1983, *J. Immunol. Methods*, 64:313, Decker and Lohmann-Matthes, 1988, *J. Immunol. Methods*, 115:61), or by measuring the lethal dose in animal models. Compounds with a large therapeutic index are preferred. The therapeutic index should be greater than 2, preferably at least 10, more preferably at least 50.

Plasma Stability Test:

The plasma stability of prodrug of Formula (I) was conducted by spiking (I) in blank plasma at 37° C. The prodrug concentration was approximately 1 µg/mL or 10 µg/mL. 100 µl of plasma sample was taken at different time points and immediately added to acidified acetonitrile, followed by filtration and dilution in a mixture containing 0.7% formic acid in 50% acetonitrile in water. The amount of remaining prodrug and the generation of compound (II) was analyzed by LC/MS/MS.

One skilled in the art would also readily appreciate that the present invention is well adapted to carry out the objects and obtain the ends and advantages mentioned, as well as those inherent herein. The molecular complexes and the methods, procedures, treatments, molecules, specific compounds described herein are presently representative of preferred embodiments, are exemplary, and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

What is claimed is:

1. A compound of Formula (I):

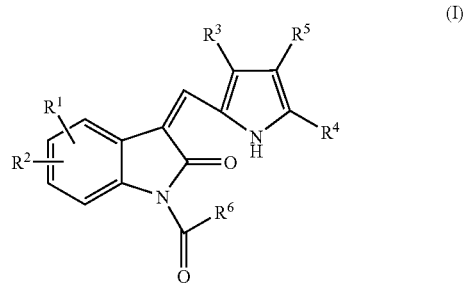

wherein:
  $R^1$ and $R^2$ are independently selected from the group consisting of hydrogen, halo, alkyl, alkylthio, nitro, trihalomethyl, hydroxy, hydroxyalkyl, alkoxy, cyano, aryl, —C(O)$R^7$ (where $R^7$ is selected from the group consisting of alkyl, amino, hydroxy, alkoxy, aryl, aryloxy, and aminoalkylamino), —NR$^8$R$^9$, —NR$^8$C(O)R$^9$, —SO$_2$R$^8$, and —S(O)$_2$NR$^8$R$^9$ (where $R^8$ and $R^9$ are independently selected from the group consisting of hydrogen, alkyl and aryl);
  $R^3$ is selected from the group consisting of hydrogen, alkyl, hydroxyalkyl, aminoalkyl, —C(O)$R^7$, where $R^7$ is as defined above, and aryl;
  $R^4$ is selected from the group consisting of hydrogen, alkyl, —C(O)$R^7$, where $R^7$ is as defined above, and aryl;
  $R^5$ is 3-amino-2-hydroxypropylaminocarbonyl, N-(2-dimethylaminoethyl)-aminocarbonyl, N-(2-diethylaminoethyl)-N-methylaminocarbonyl, N-(3-dimethylaminopropyl)aminocarbonyl, N-(2-diethylaminoethyl)-aminocarbonyl, N-(3-ethylaminopropyl)aminocarbonyl, N-(3-ethylamino-2-hydroxypropyl)aminocarbonyl, N-(3-diethylamino-propyl)aminocarbonyl, 3-amino-2-hydroxypropylaminocarbonyl, 3-dimethylamino-2-hydroxypropylaminocarbonyl, 3-diethylamino-2-hydroxypropylaminocarbonyl, N-(3-diethylamino-2-hydroxy-propyl)aminocarbonyl, N-(2-diethylaminoethyl)-aminocarbonyl or N-(ethylaminoethyl)aminocarbonyl;
  $R^6$ is:
  (a) —OR$^{13}$ wherein $R^{13}$ is alkyl, trifluoromethyl, carboxyalkyl, aminoalkyl, phosphonooxyalkyl, sulfooxyalkyl, hydroxyalkyl, alkoxyalkyl, aryl, pyrrole, pyrrolidone, imidazole, thiophene, furan, tetrahydropyranyl and monosaccharides wherein the alkyl chain in carboxyalkyl, aminoalkyl, phosphonooxyalkyl, sulfooxyalkyl, hydroxyalkyl, or alkoxyalkyl is optionally substituted with one or two hydroxy group(s) and further wherein one or two carbon atoms in said alkyl chain are optionally replaced by oxygen, —NR$^{14}$— (where $R^{14}$ is hydrogen or alkyl), —S—, or —SO$_2$—; or
  (b) —NR$^{15}$R$^{16}$ where are $R^{15}$ and $R^{16}$ are independently selected from the group consisting of hydrogen, alkyl, carboxyalkyl, alkoxyalkyl, aminoalkyl, phosphonooxyalkyl, sulfooxyalkyl, hydroxyalkyl, pyrrole, pyrrolidone, imidazole, thiophene, furan, tetrahydropyranyl and aryl; wherein the alkyl chain in carboxyalkyl, aminoalkyl, phosphonooxyalkyl, hydroxyalkyl, or alkoxyalkyl is optionally substituted with one or two hydroxy group(s) and further wherein one or two carbon atoms in the alkyl chain are optionally replaced by oxygen, —$NR^{17}$—, where $R^{17}$ is hydrogen or alkyl, —S—, or —$SO_2$—; or $R^{15}$ and $R^{16}$ together with the nitrogen atom to which they are attached form a heterocycloamino, wherein the heterocycloamino is pyrrole, pyrrolidone, imidazole, thiophere or furan or a pharmaceutically acceptable salt thereof.

2. A pharmaceutical composition, comprising a compound or salt of claim 1 and a pharmaceutically acceptable carrier or excipient.

3. The compound of claim 1, wherein $R^5$ is N-(2-diethylaminoethyl)aminocarbonyl.

4. The compound of claim 3, wherein $R^3$ and $R^4$ are lower alkyl having 1 to 4 carbon atoms.

5. The compound of claim 4, wherein $R^3$ and $R^4$ are methyl.

6. The compound of claim 5, wherein $R^1$ is hydrogen and $R^2$ is fluoro.

7. The compound of claim 6, wherein $R^2$ is a fluoro at the 5 position of the indolinone moeity.

8. A pharmaceutical composition comprising the compound of claim 7 and a pharmaceutically acceptable carrier or excipient.

* * * * *